United States Patent [19]
Heidt et al.

[11] Patent Number: 5,336,467
[45] Date of Patent: Aug. 9, 1994

[54] CHEMICAL ANALYZER

[75] Inventors: Thomas Heidt, Long Valley; Henry Will, Dover; Greydon Rhodes, Chester; Armand Plasensia, Hopatcong, all of N.J.; Roger Clampitt, Hemel Hempstead, United Kingdom

[73] Assignee: VetTest S.A., Neuchatel, Switzerland

[21] Appl. No.: 87,180

[22] Filed: Jul. 2, 1993

Related U.S. Application Data

[60] Division of Ser. No. 806,071, Dec. 6, 1991, Pat. No. 5,250,262, which is a continuation of Ser. No. 441,451, Nov. 22, 1989, Pat. No. 5,089,229.

[51] Int. Cl.⁵ .................................... G01N 21/00
[52] U.S. Cl. ................................ 422/64; 422/63; 422/82.05; 422/100; 436/46; 436/54; 73/863.01; 73/864.18; 222/390; 364/555; 364/167.01
[58] Field of Search ............... 422/64, 63, 82.05, 100; 436/46, 54; 73/1 H, 863.01, 864.18; 222/390; 425/145; 364/167, 555

[56] References Cited

U.S. PATENT DOCUMENTS

| | | | |
|---|---|---|---|
| 282,203 | 1/1886 | Leonard et al. | 57/66.5 |
| 2,058,516 | 10/1936 | Schaaff | 141/24 |
| 2,204,471 | 6/1940 | Campbell, Jr. et al. | 141/29 |
| 2,363,474 | 11/1944 | Schlesinger | 222/179.5 |
| 2,586,513 | 2/1952 | Butler | 210/94 |
| 2,598,869 | 6/1952 | White | 141/113 |
| 2,665,825 | 1/1954 | Poitras et al. | 222/209 |
| 2,692,820 | 10/1954 | Alway et al. | 210/659 |
| 2,721,008 | 10/1955 | Morgan, Jr. | 222/334 |
| 2,797,149 | 6/1957 | Skeggs | 436/53 |
| 2,802,605 | 8/1957 | Parker | 222/215 |
| 3,036,893 | 5/1962 | Natelson | 436/170 |
| 3,106,845 | 10/1963 | Dimmick | 73/164.11 |
| 3,164,304 | 1/1965 | Jager et al. | 222/192 |
| 3,190,731 | 6/1965 | Weiskopf | 422/102 |
| 3,300,099 | 1/1967 | Marona | 222/207 |
| 3,323,689 | 6/1967 | Elmore | 222/385 |
| 3,341,087 | 9/1967 | Rosin et al. | 422/422 |
| 3,367,746 | 2/1968 | Maurukas | 422/100 |
| 3,449,081 | 6/1969 | Hughes | 422/61 |
| 3,460,529 | 8/1969 | Leucci | 128/767 |
| 3,526,480 | 9/1970 | Findl et al. | 422/66 |
| 3,533,744 | 10/1970 | Unger | 436/63 |
| 3,572,400 | 3/1971 | Casner et al. | 141/1 |
| 3,574,064 | 4/1971 | Binnings et al. | 435/293 |
| 3,615,240 | 10/1971 | Sanz | 73/864.13 |
| 3,616,264 | 10/1971 | Ray et al. | 435/290 |
| 3,618,829 | 11/1971 | Elmore et al. | 222/209 |
| 3,645,423 | 2/1972 | DeGraw | 222/207 |
| 3,650,437 | 3/1972 | Binnings et al. | 222/136 |
| 3,659,934 | 5/1972 | Costanza et al. | 353/103 |
| 3,675,488 | 7/1972 | Viktora et al. | 73/863.12 |
| 3,748,044 | 7/1973 | Liston | 356/409 |
| 3,754,866 | 8/1973 | Ritchie et al. | 422/73 |
| 3,756,920 | 9/1973 | Kelbaugh et al. | 435/291 |
| 3,758,274 | 9/1973 | Ritchie et al. | 422/50 |
| 3,788,816 | 1/1974 | Rohrbaugh et al. | 422/64 |
| 3,790,346 | 2/1974 | Ritchie | 422/64 |
| 3,810,779 | 5/1974 | Pickett et al. | 427/256 |
| 3,832,135 | 8/1974 | Drozdowski et al. | 422/64 |
| 3,855,867 | 12/1974 | Roach | 73/864.18 X |
| 3,856,470 | 12/1974 | Cullis et al. | 422/64 |
| 3,873,273 | 3/1975 | Moran et al. | 422/64 |
| 3,883,308 | 5/1975 | Matte | 422/64 |
| 3,904,372 | 9/1975 | Lightner | 422/63 |
| 3,915,651 | 10/1975 | Nishi | 73/864.16 |

(List continued on next page.)

Primary Examiner—James C. Housel
Assistant Examiner—Harold Y. Pyon
Attorney, Agent, or Firm—Hoffmann & Baron

[57] ABSTRACT

A chemical analyzer includes a transport mechanism having a rotatable turntable adapted to hold a plurality of reagent test slides, a sample metering device, an incubator or temperature controller, a reflectometer and associated electronics and software. The rotatable turntable preferably holds up to twelve slides about its circumference, which slides are loaded onto the turntable by an inserter mechanism. The turntable positions the reagent test slides under the metering device, which device deposits a predetermined amount of sample onto each slide. The turntable also carries the slides above a reflectometer. After testing has been completed, an ejector mechanism automatically removes the reagent slides from the turntable.

1 Claim, 70 Drawing Sheets

U.S. PATENT DOCUMENTS

| | | | |
|---|---|---|---|
| 3,918,913 | 11/1975 | Stevenson et al. | 73/863.72 |
| 3,926,514 | 12/1975 | Costanza et al. | 353/113 |
| 3,942,952 | 3/1976 | Atwood | 73/864.91 |
| 4,041,995 | 8/1977 | Columbus | 141/275 |
| 4,043,756 | 8/1977 | Sommervold | 436/43 |
| 4,052,161 | 10/1977 | Atwood et al. | 436/34 |
| 4,059,405 | 11/1977 | Sodickson et al. | 436/44 |
| 4,061,469 | 12/1977 | Dubose | 422/64 |
| 4,067,694 | 1/1978 | Blakely et al. | 422/63 |
| 4,090,791 | 5/1978 | Siddiqi et al. | 356/414 |
| 4,119,381 | 10/1978 | Muka et al. | 356/244 |
| 4,142,656 | 3/1979 | Smith et al. | 222/325 |
| 4,152,390 | 5/1979 | Nosco et al. | 422/63 |
| 4,160,646 | 7/1979 | Furutani et al. | 436/169 |
| 4,161,508 | 7/1979 | Janchen | 422/100 |
| 4,198,483 | 4/1980 | Sogi et al. | 435/286 |
| 4,198,485 | 4/1980 | Stark, Jr. | 521/55 |
| 4,210,724 | 7/1980 | Sogi et al. | 435/292 |
| 4,219,529 | 8/1980 | Tersteeg et al. | 422/65 |
| 4,224,032 | 9/1980 | Glover et al. | 436/46 |
| 4,234,538 | 11/1980 | Ginsberg et al. | 422/64 |
| 4,234,539 | 11/1980 | Ginsberg et al. | 422/64 |
| 4,236,894 | 12/1980 | Sommervold | 436/43 |
| 4,264,560 | 4/1981 | Natelson | 422/58 |
| 4,271,123 | 6/1981 | Curry et al. | 422/64 |
| 4,272,482 | 6/1981 | Jessop et al. | 422/65 |
| 4,277,440 | 7/1981 | Jessop et al. | 422/100 |
| 4,287,155 | 9/1981 | Tersteeg et al. | 422/64 |
| 4,296,069 | 10/1981 | Smith et al. | 422/64 |
| 4,296,070 | 10/1981 | Montalto et al. | 422/65 |
| 4,298,571 | 11/1981 | DiFulvio et al. | 422/65 |
| 4,298,575 | 11/1981 | Berglund | 73/864.13 |
| 4,302,420 | 11/1981 | Jakubowicz et al. | 422/63 |
| 4,303,611 | 12/1981 | Jessop | 422/65 |
| 4,308,231 | 12/1981 | Kolber et al. | 422/64 |
| 4,321,122 | 3/1982 | Whitcomb et al. | 204/400 |
| 4,325,909 | 4/1982 | Coulter et al. | 422/63 |
| 4,335,620 | 6/1982 | Adams | 73/863.11 |
| 4,340,390 | 7/1982 | Collins et al. | 436/54 |
| 4,347,750 | 9/1982 | Tersteeg et al. | 73/864.31 |
| 4,351,799 | 9/1982 | Gross et al. | 422/63 |
| 4,359,447 | 11/1982 | Welch | 422/63 |
| 4,392,195 | 7/1983 | Inoue | 364/167 |
| 4,399,711 | 8/1983 | Klein | 73/864.16 |
| 4,420,566 | 12/1983 | Jessop et al. | 436/46 |
| 4,424,191 | 1/1984 | Jakubowicz | 422/65 |
| 4,429,373 | 1/1984 | Fletcher et al. | 422/55 |
| 4,430,299 | 2/1984 | Horne | 422/64 |
| 4,441,532 | 4/1984 | Hrubesh | 141/1 |
| 4,451,433 | 5/1984 | Yamashita et al. | 422/63 |
| 4,452,899 | 6/1984 | Alston | 436/46 |
| 4,455,280 | 6/1984 | Shinohara et al. | 422/63 |
| 4,475,666 | 10/1984 | Bilbrey et al. | 222/14 |
| 4,488,810 | 12/1984 | Hatanaka et al. | 356/244 |
| 4,503,011 | 3/1985 | Hubeau | 422/73 |
| 4,512,952 | 4/1985 | Blanding et al. | 422/63 |
| 4,522,971 | 6/1985 | Ogawa | 524/547 |
| 4,539,855 | 9/1985 | Jacobs | 73/864.25 |
| 4,540,549 | 9/1985 | Manabe | 422/64 |
| 4,549,809 | 10/1985 | Minekane et al. | 356/436 |
| 4,568,519 | 2/1986 | Hamilton et al. | 422/64 |
| 4,584,275 | 4/1986 | Okano et al. | 435/290 |
| 4,599,219 | 7/1986 | Cooper et al. | 422/61 |
| 4,615,360 | 10/1986 | Jacobs | 141/18 |
| 4,629,703 | 12/1986 | Uffenheimer | 436/45 |
| 4,644,807 | 2/1987 | Mar | 73/864.62 |
| 4,647,431 | 3/1987 | Sekine et al. | 422/63 |
| 4,656,006 | 4/1987 | Assmann et al. | 422/63 |
| 4,656,007 | 4/1987 | Douchy et al. | 422/64 |
| 4,670,219 | 6/1987 | Nelson et al. | 422/63 |
| 4,675,301 | 6/1987 | Charneski et al. | 436/180 |
| 4,678,755 | 7/1987 | Shinohara et al. | 436/43 |
| 4,680,164 | 7/1987 | Kelln | 422/72 |
| 4,681,741 | 7/1987 | Hanaway | 422/100 |
| 4,695,430 | 9/1987 | Coville et al. | 422/65 |
| 4,706,207 | 11/1987 | Hennessy et al. | 364/555 |
| 4,710,352 | 12/1987 | Slater et al. | 422/63 |
| 4,713,974 | 12/1987 | Stone | 73/864.23 |
| 4,731,058 | 3/1988 | Doan | 222/390 X |
| 4,737,344 | 4/1988 | Koizumi et al. | 422/100 |
| 4,738,826 | 4/1988 | Harris | 422/100 |
| 4,757,449 | 6/1988 | Jackson et al. | 422/73 |
| 4,761,268 | 8/1988 | Andersen et al. | 422/72 |
| 4,769,009 | 9/1988 | Dykstra | 222/390 X |
| 4,770,053 | 9/1988 | Broderick et al. | 73/866.5 |
| 4,774,055 | 9/1988 | Wakatake et al. | 422/64 |
| 4,785,407 | 11/1988 | Sakagami | 364/497 |
| 4,794,085 | 12/1988 | Jessop et al. | 436/54 |
| 4,798,705 | 1/1989 | Jakubowicz et al. | 422/63 |
| 4,808,380 | 2/1989 | Minekane | 422/64 |
| 4,814,279 | 3/1989 | Sugaya | 435/289 |
| 4,821,586 | 4/1989 | Scordato et al. | 73/864.18 |
| 4,823,992 | 4/1989 | Fiorentini | 222/333 |
| 4,826,659 | 5/1989 | Akisada | 422/63 |
| 4,837,159 | 6/1989 | Yamada | 436/45 |
| 4,841,208 | 6/1989 | Itoh | 425/145 X |
| 4,855,109 | 8/1989 | Muraishi et al. | 422/63 |
| 4,863,695 | 9/1989 | Fullemann | 422/100 |
| 4,943,415 | 7/1990 | Przybylowicz et al. | 422/56 |
| 5,034,191 | 7/1991 | Porte | 422/64 |
| 5,037,613 | 8/1991 | Shaw et al. | 422/64 |
| 5,102,624 | 4/1992 | Muraishi | 422/64 |

FOREIGN PATENT DOCUMENTS

| | | |
|---|---|---|
| 0042337 | 12/1981 | European Pat. Off. . |
| 0042340 | 12/1981 | European Pat. Off. . |

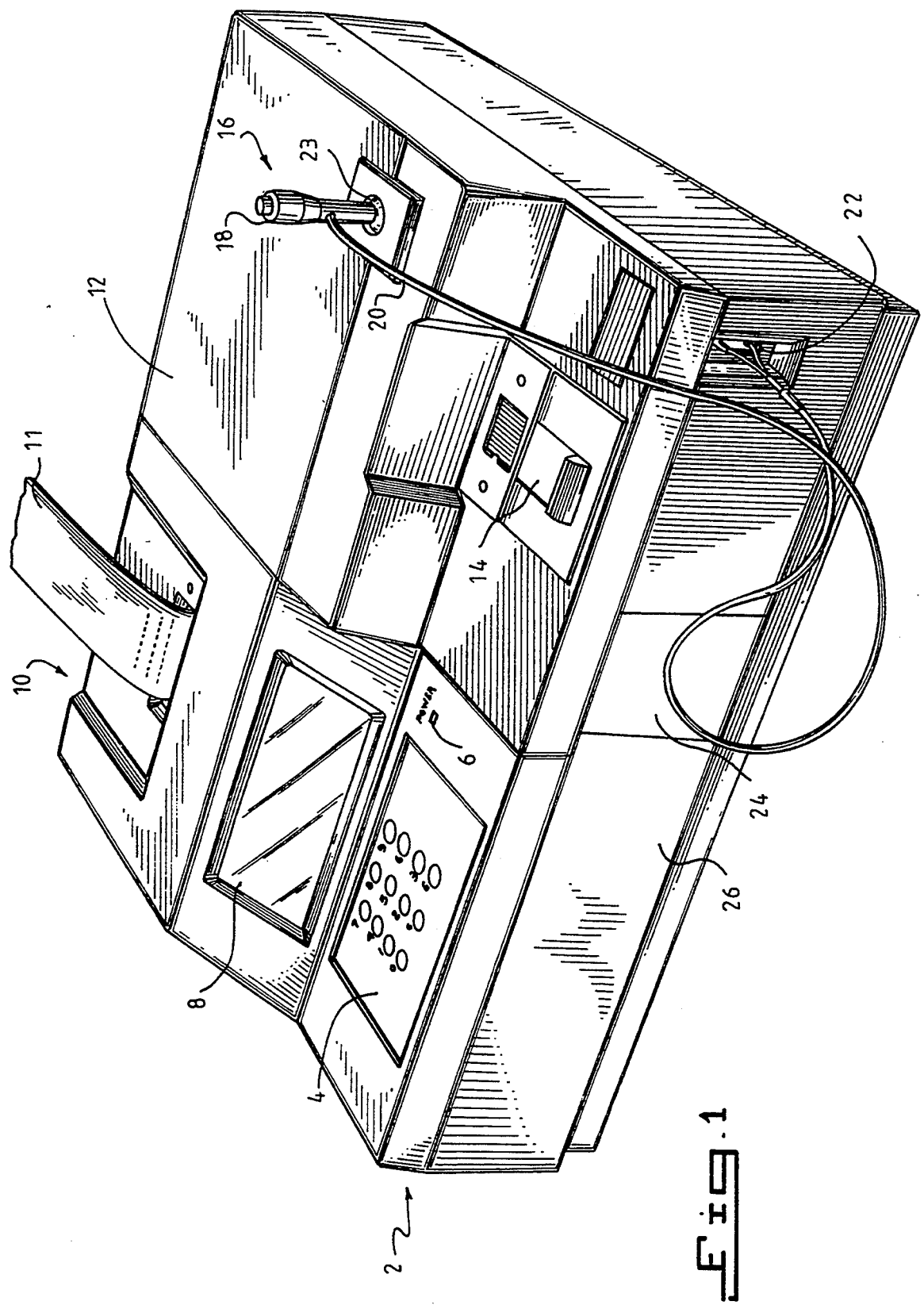

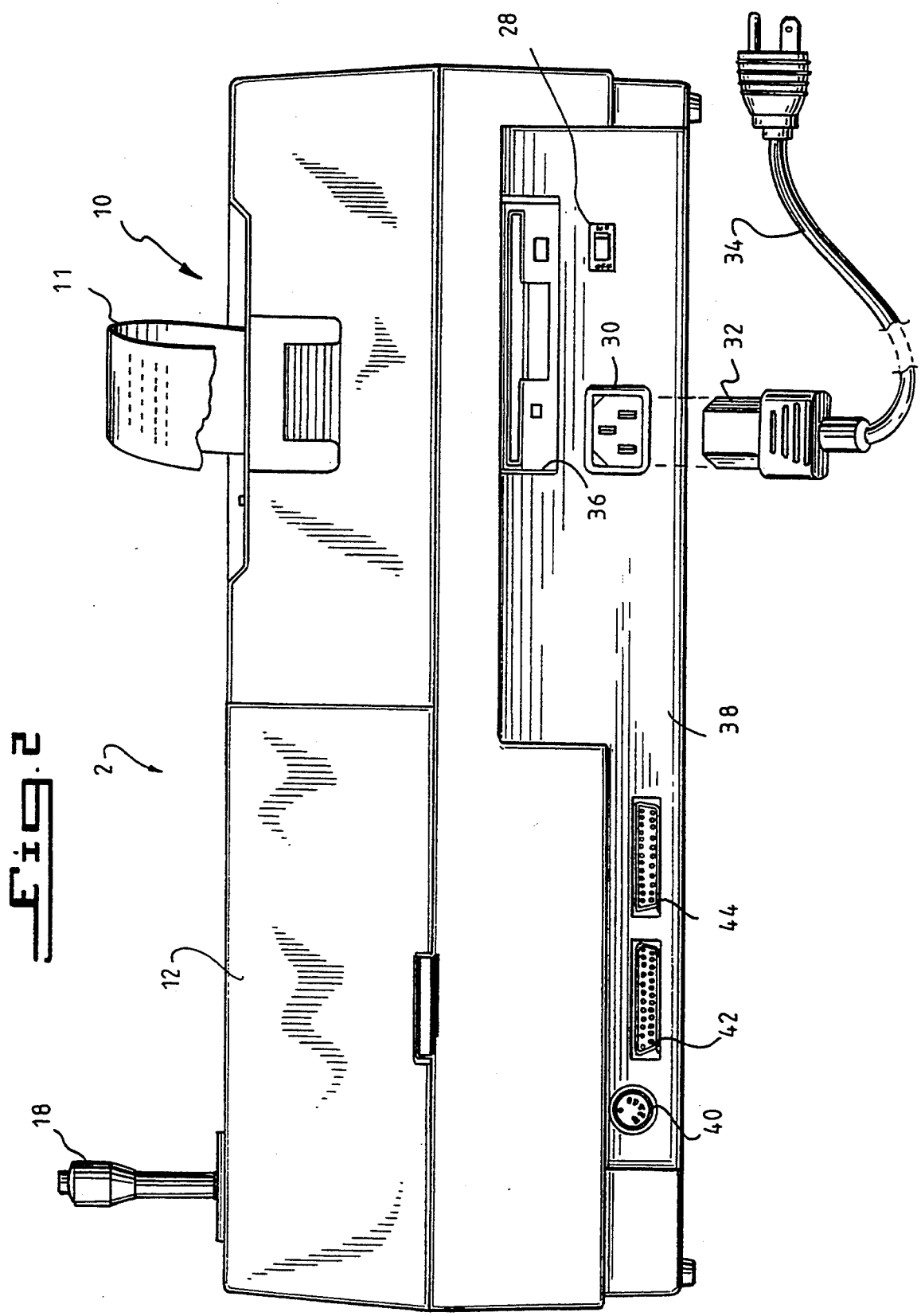

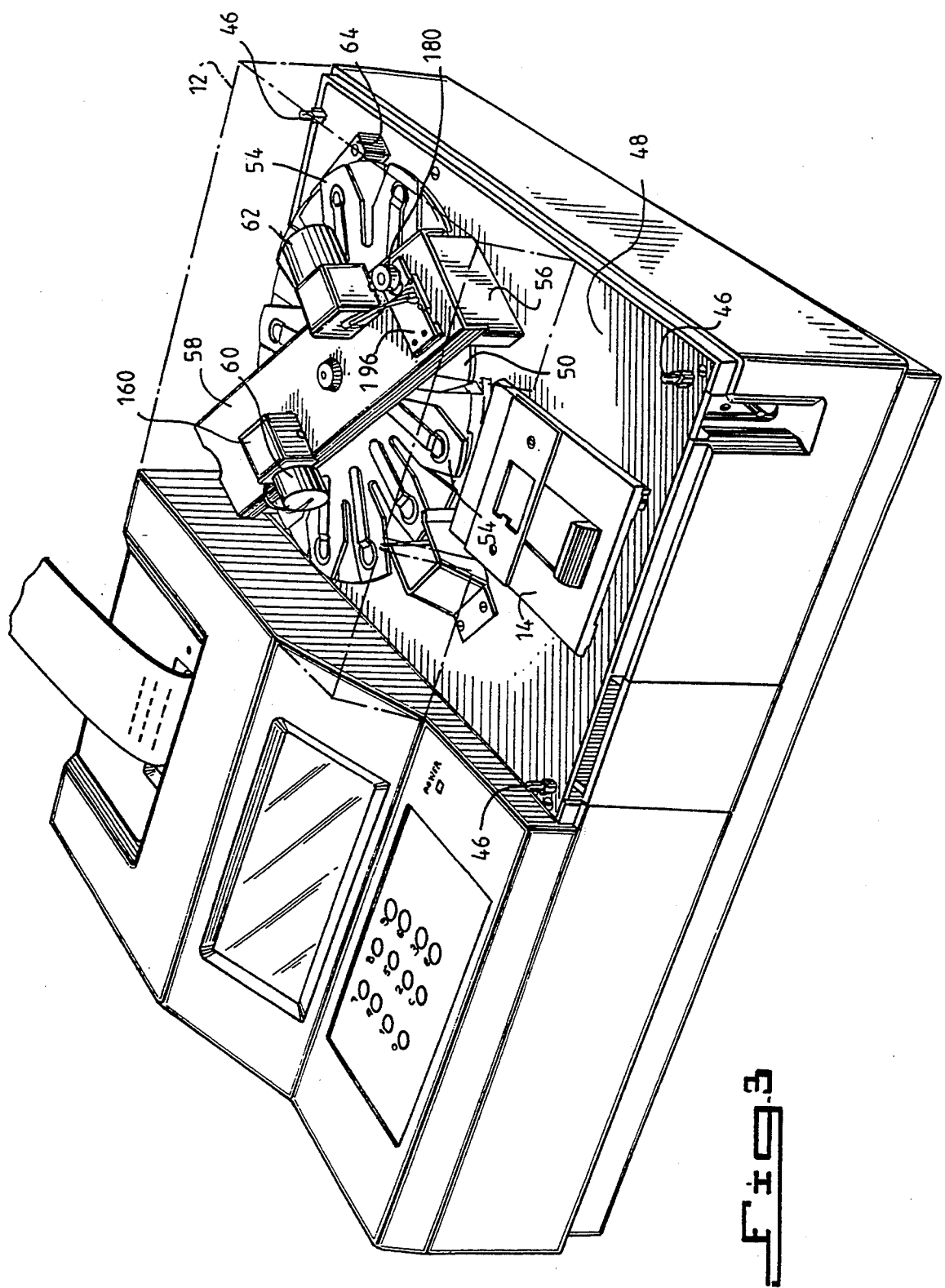

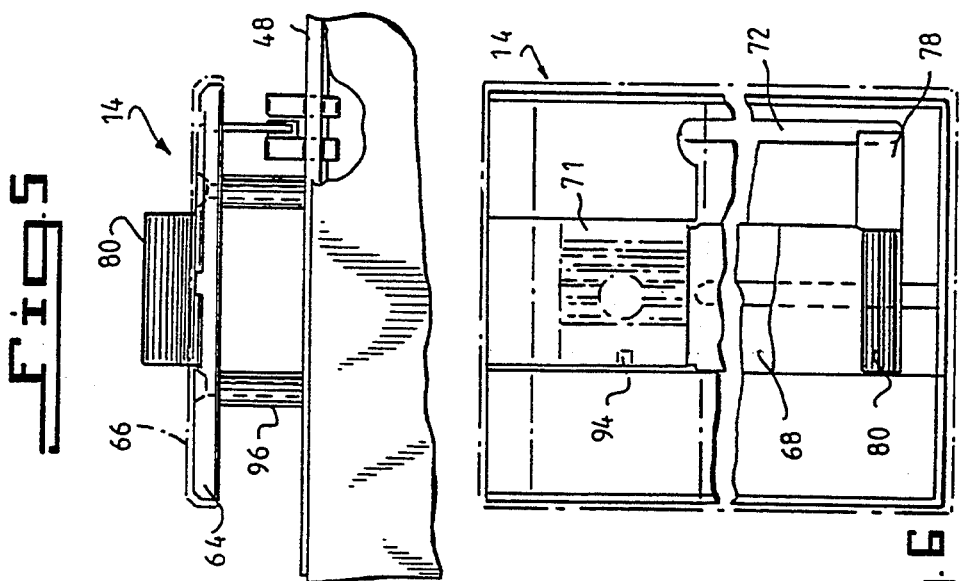
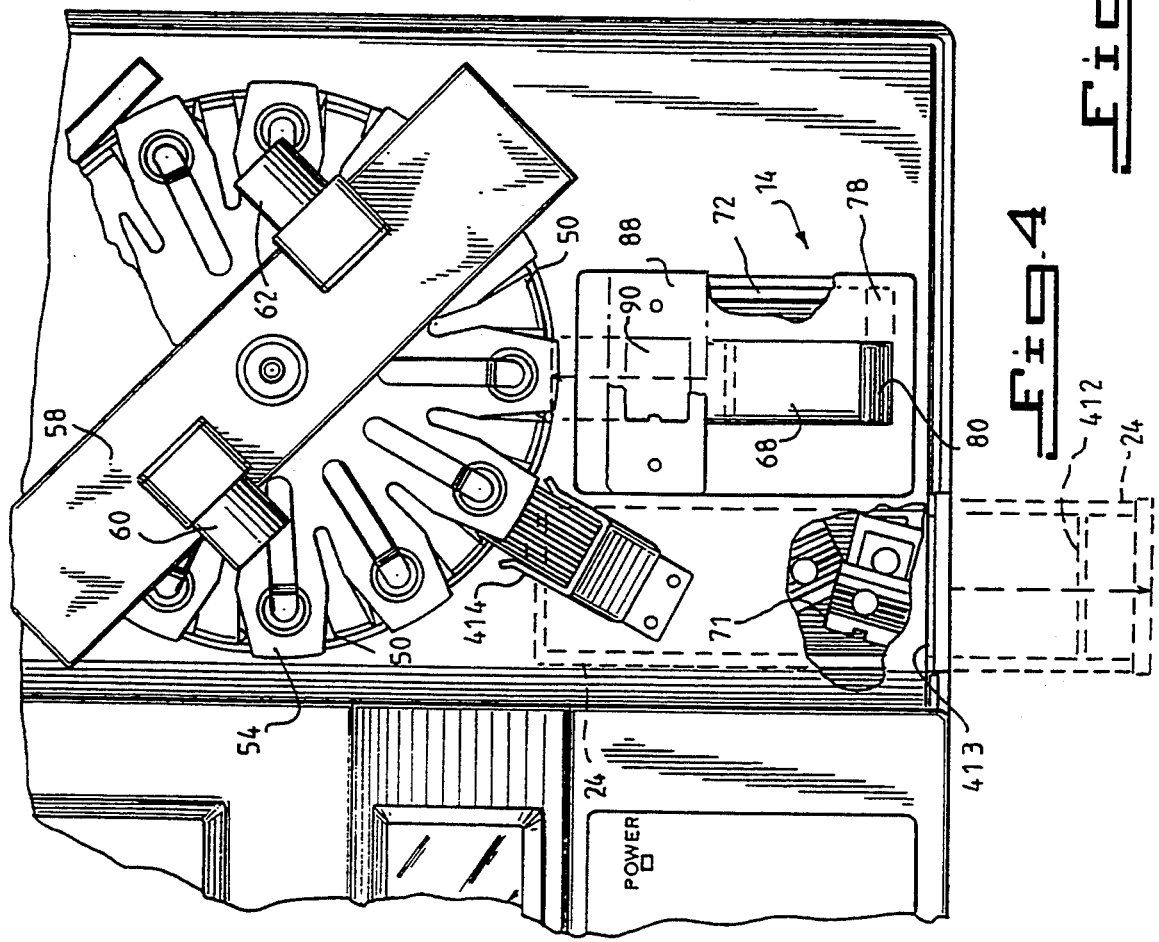

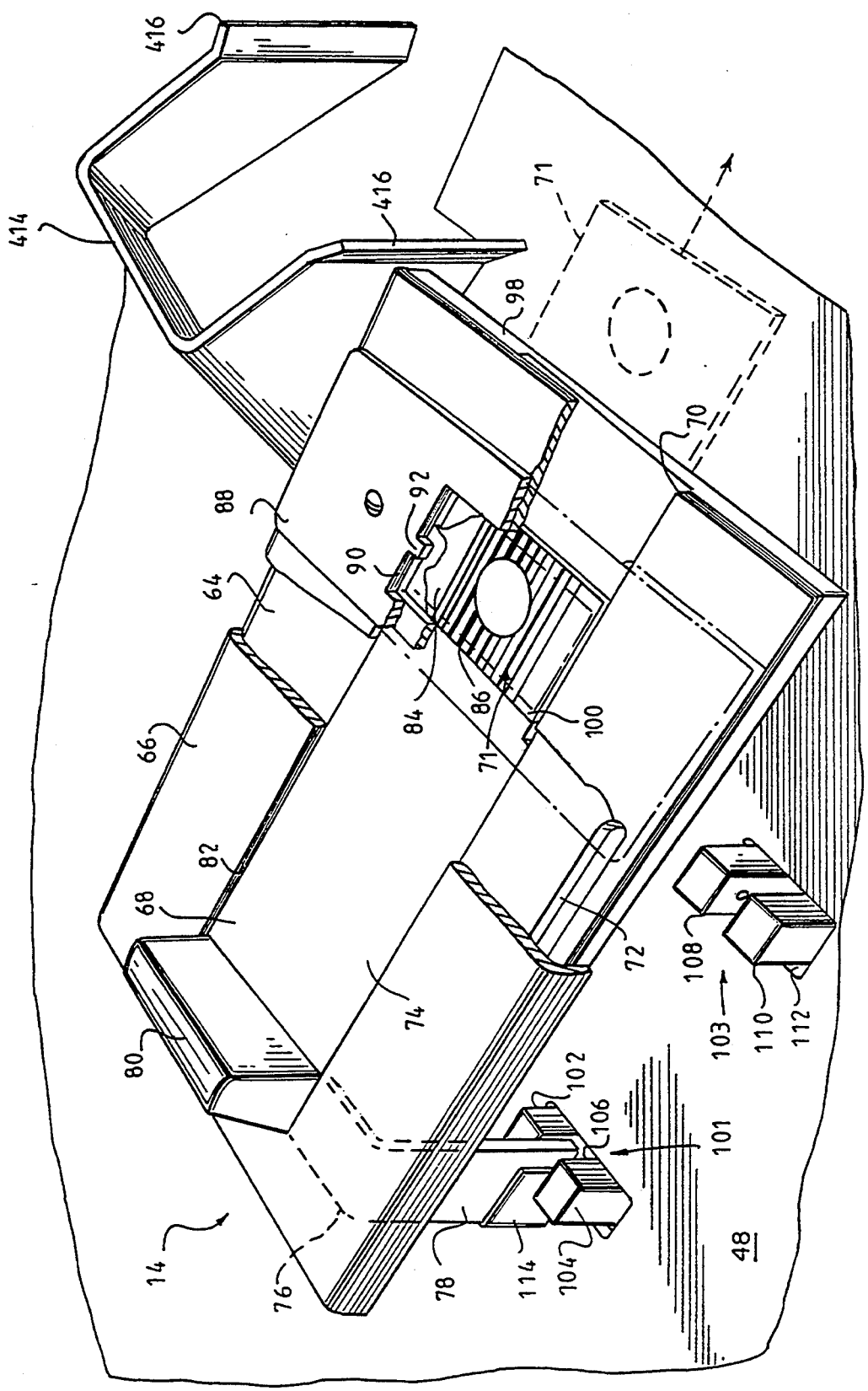

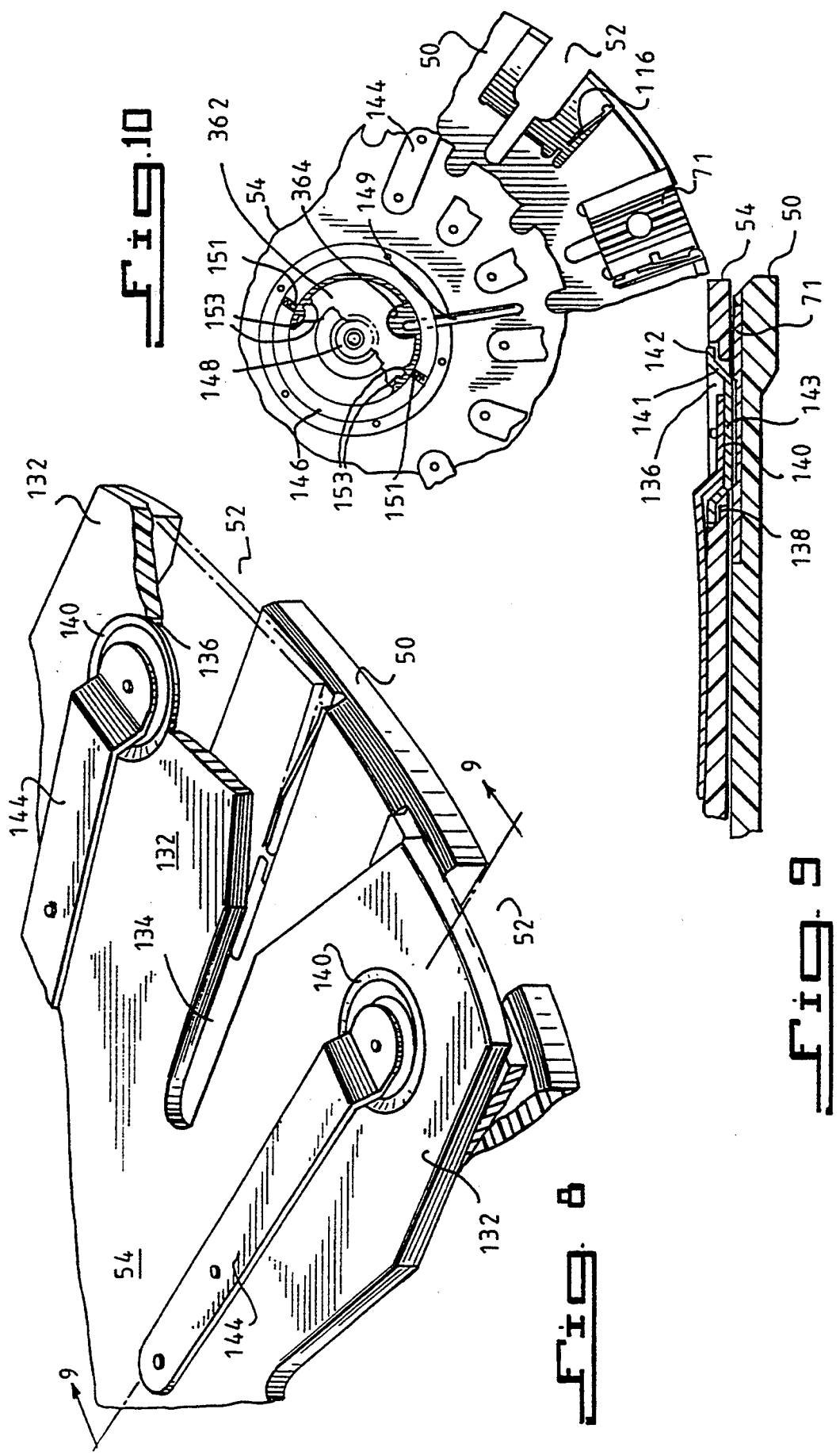

FIG. 8A
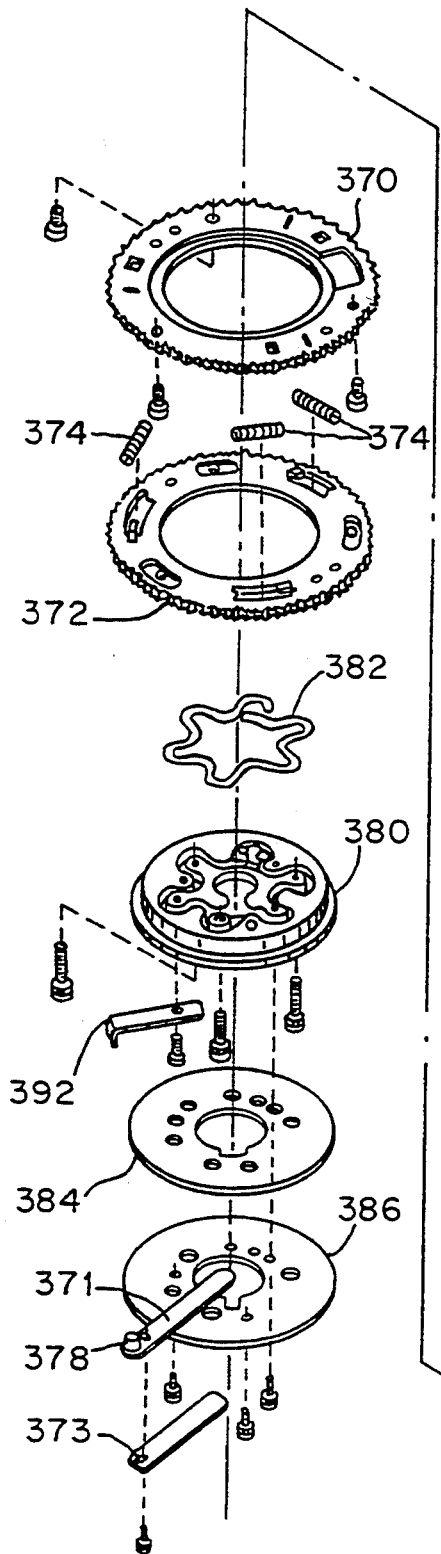
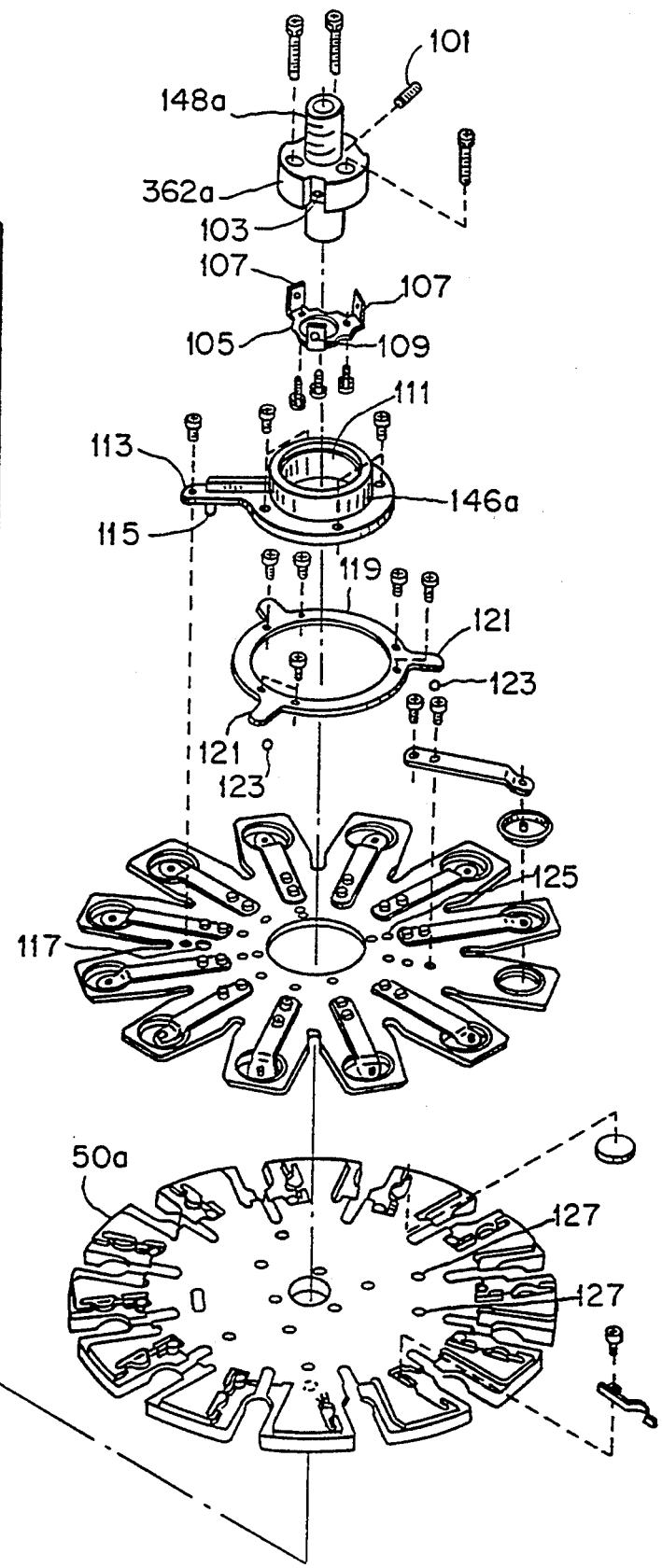

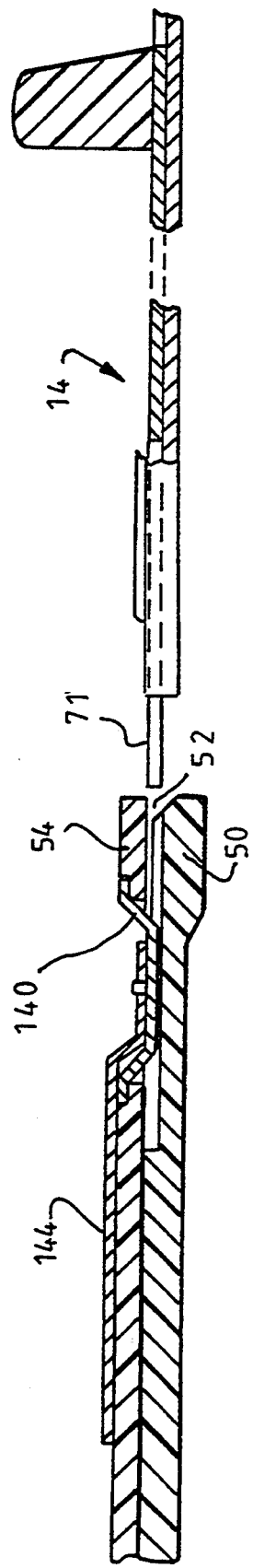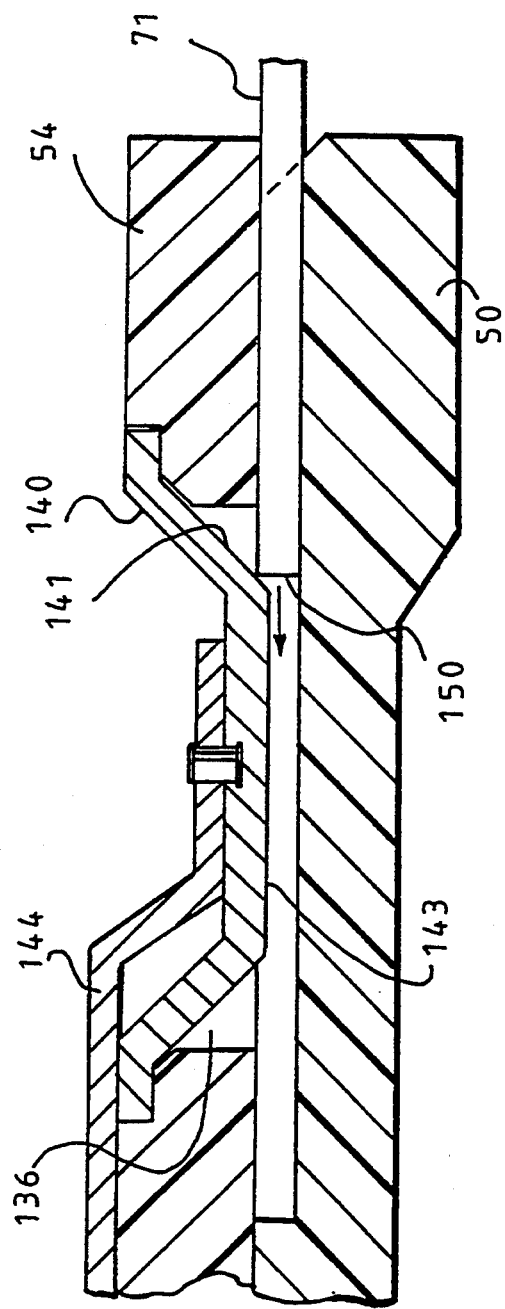

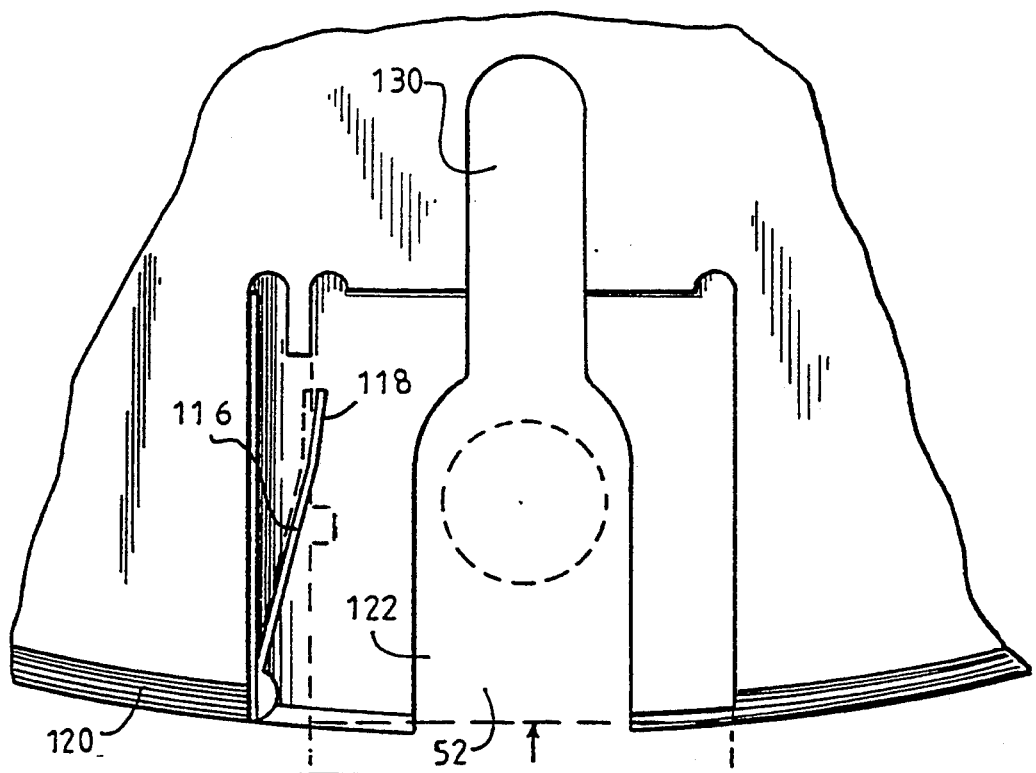
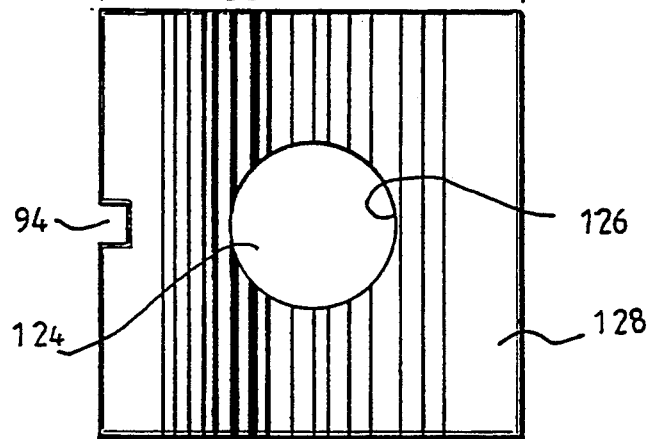
Fig. 10A
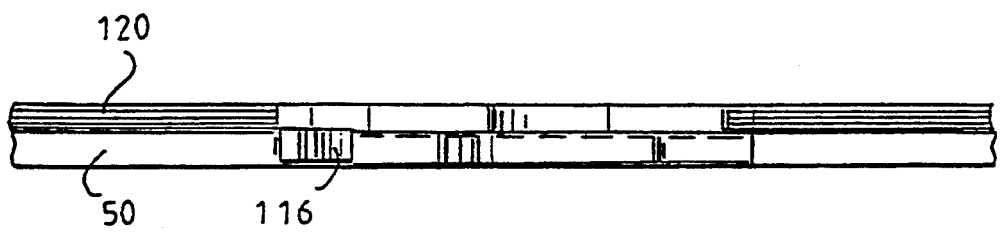
Fig. 10B

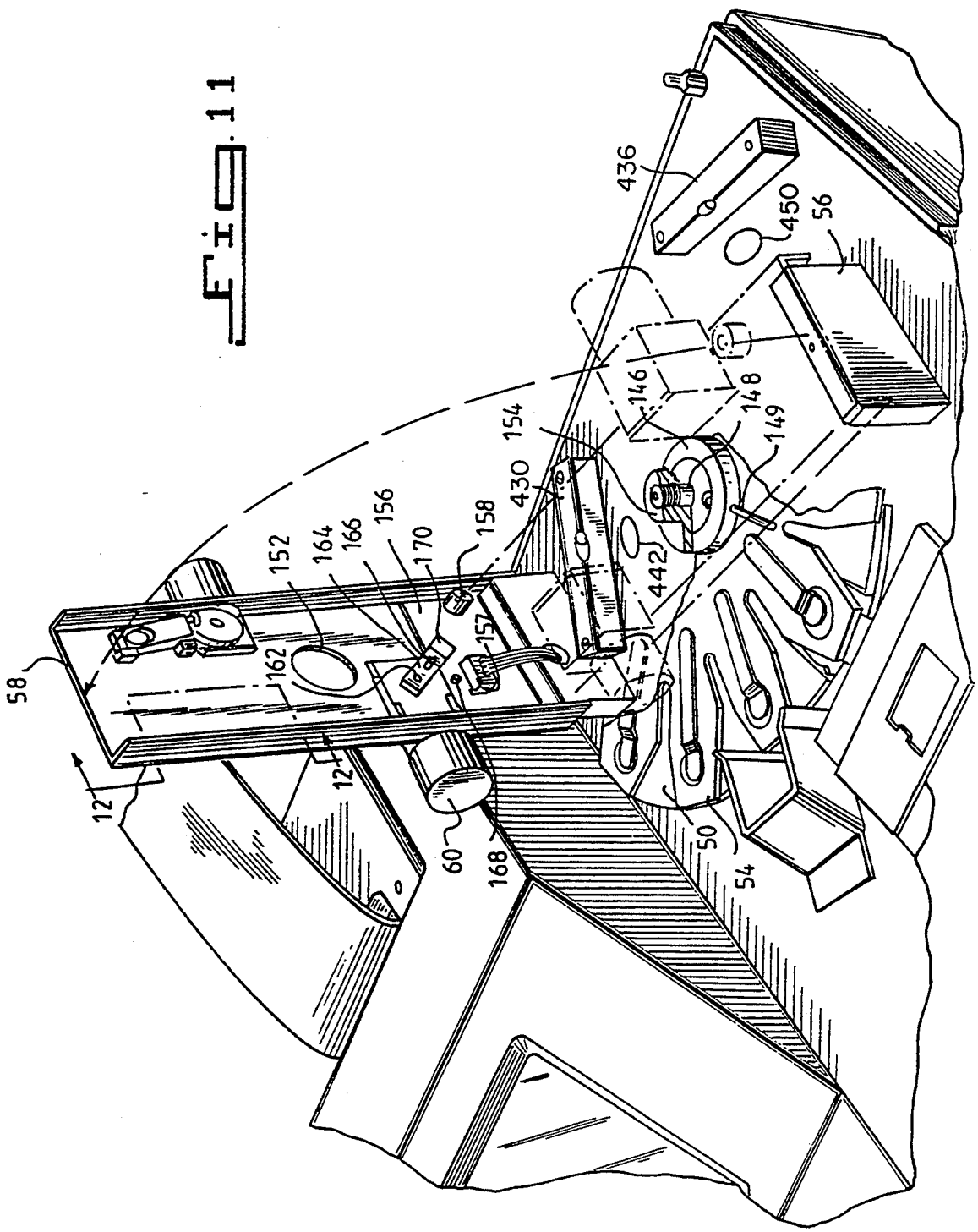

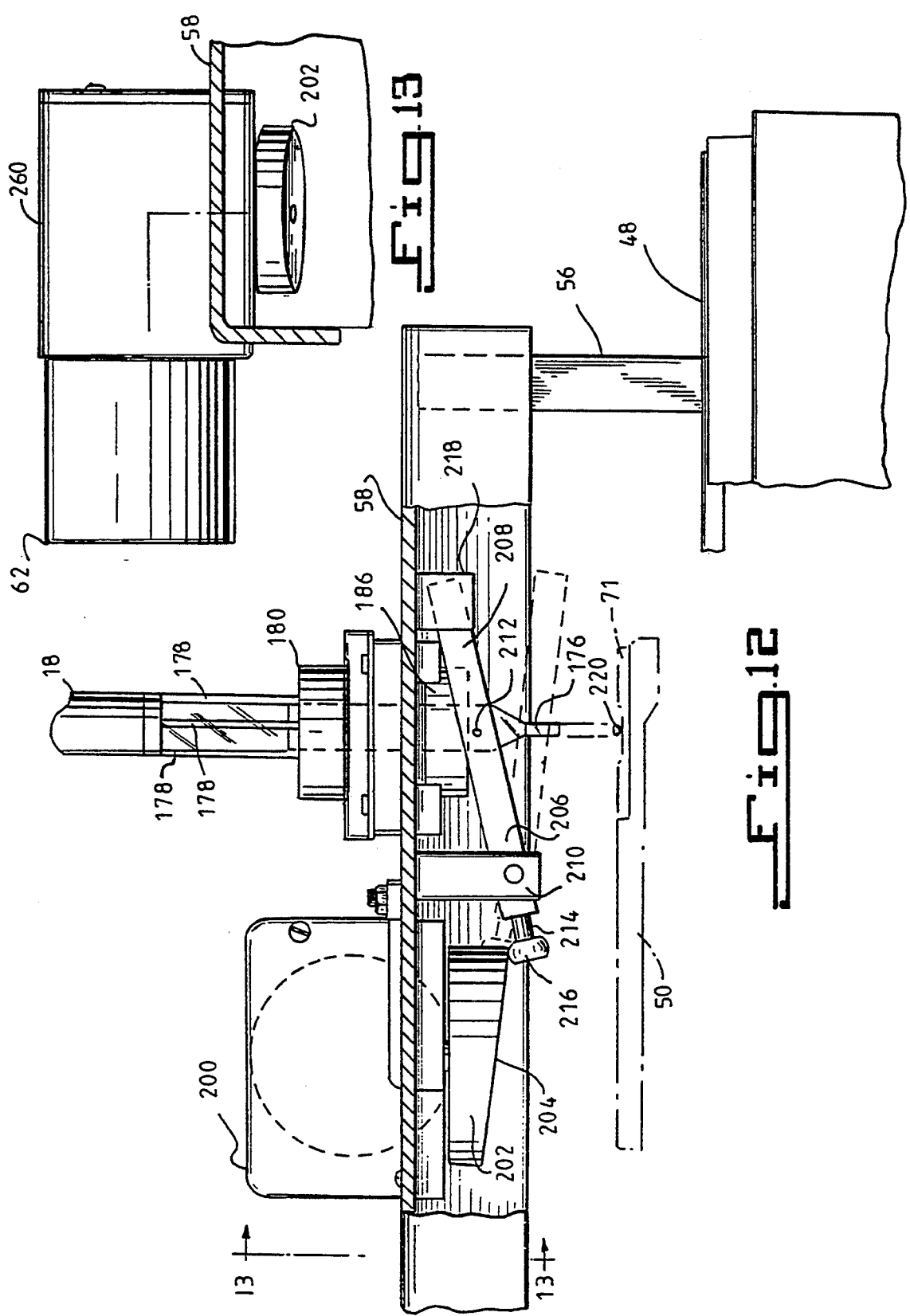

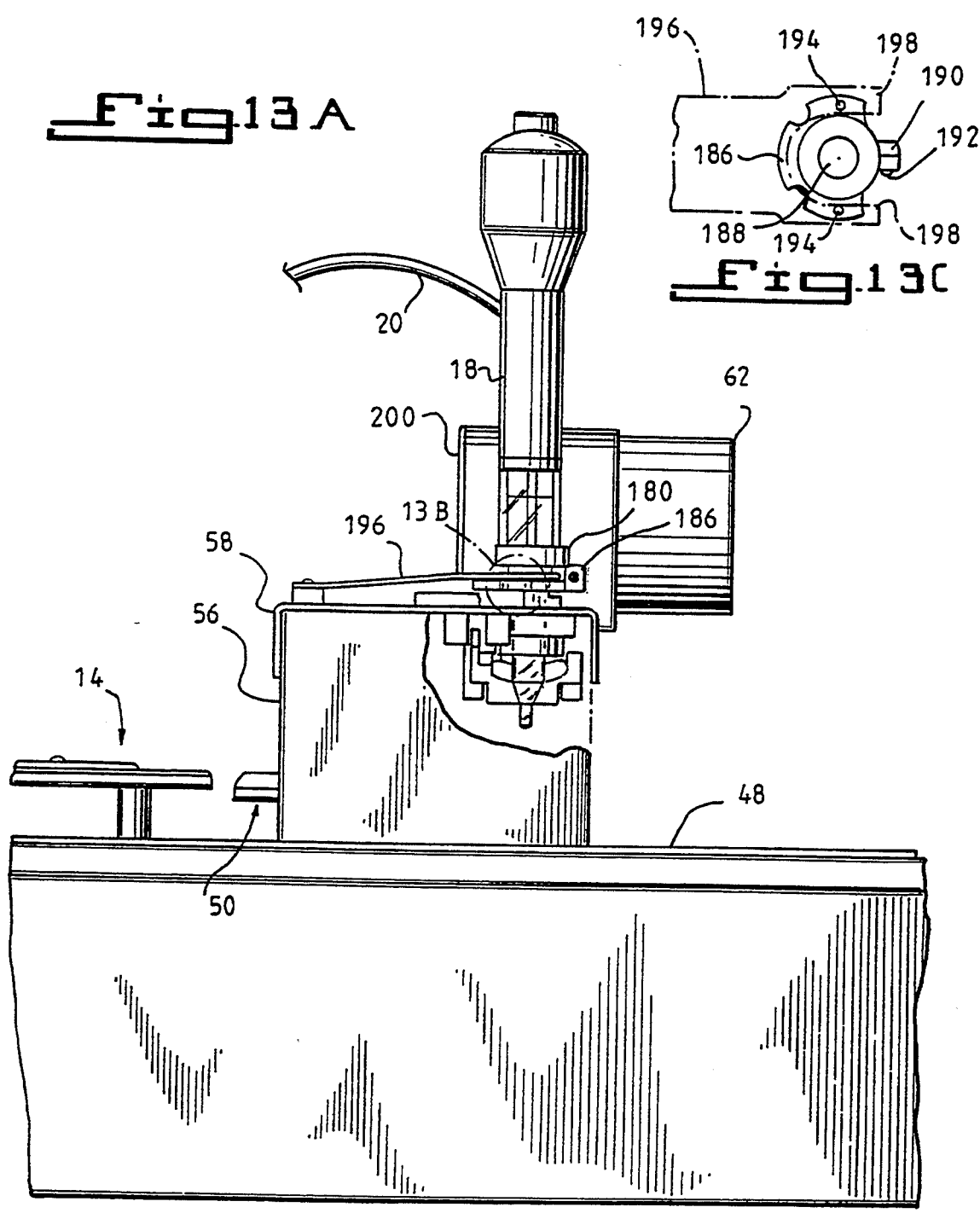
Fig.13A
Fig.13C
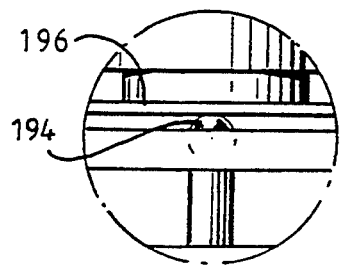
Fig.13B

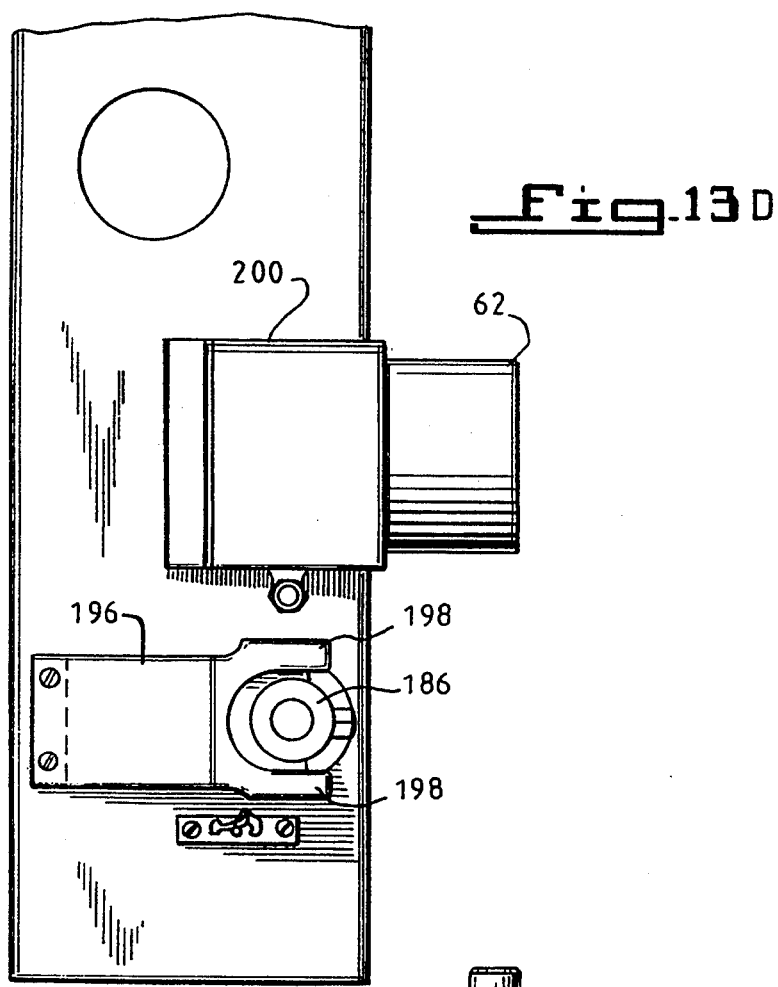
Fig.13D
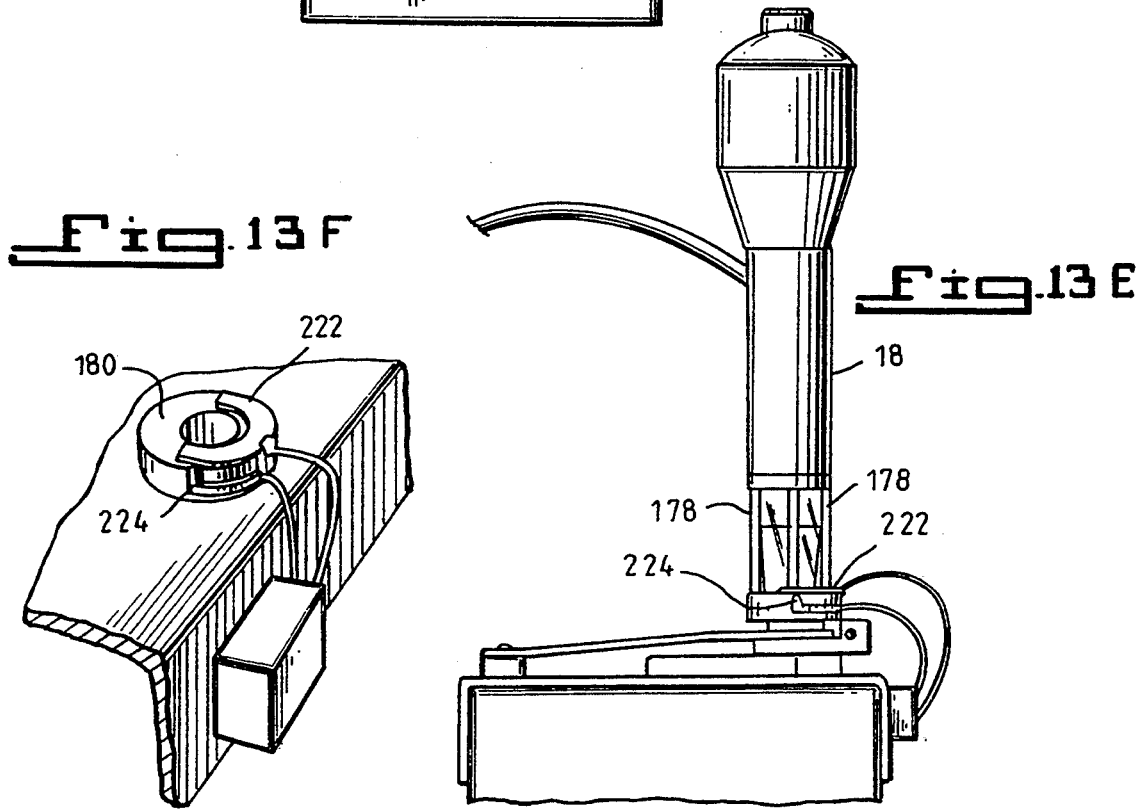
Fig.13F
Fig.13E

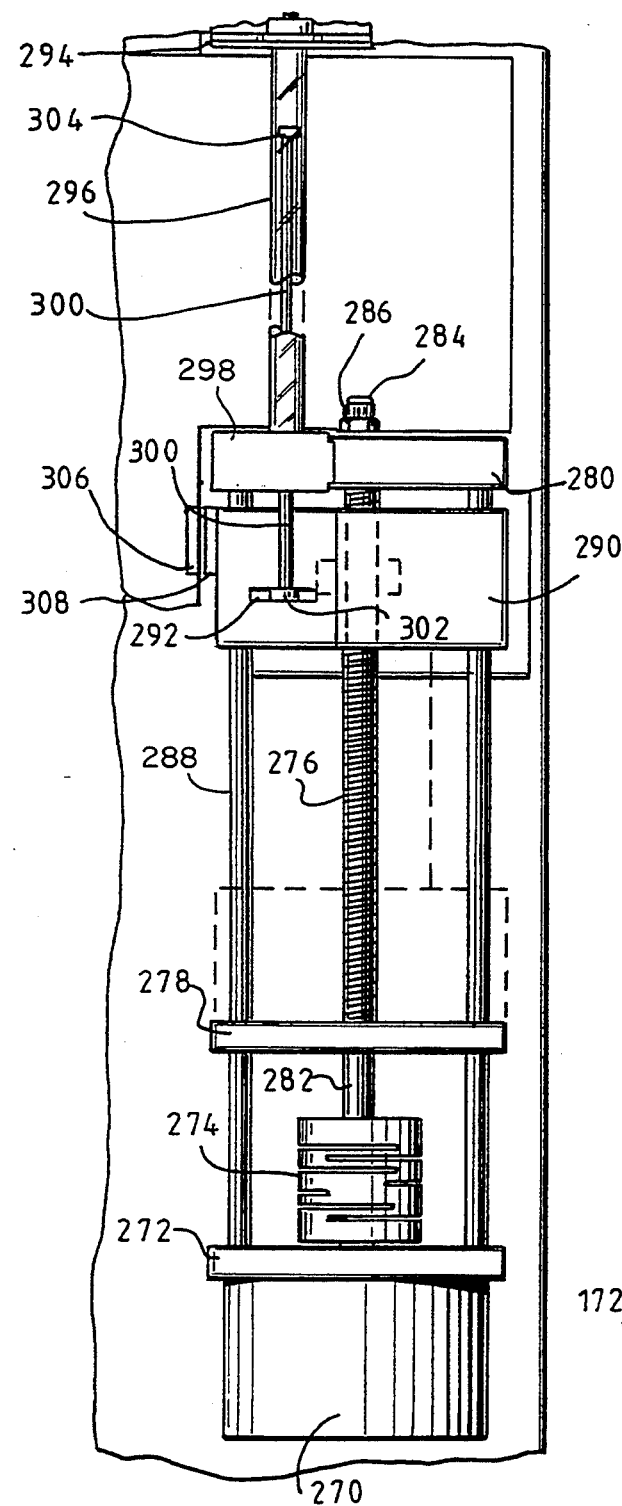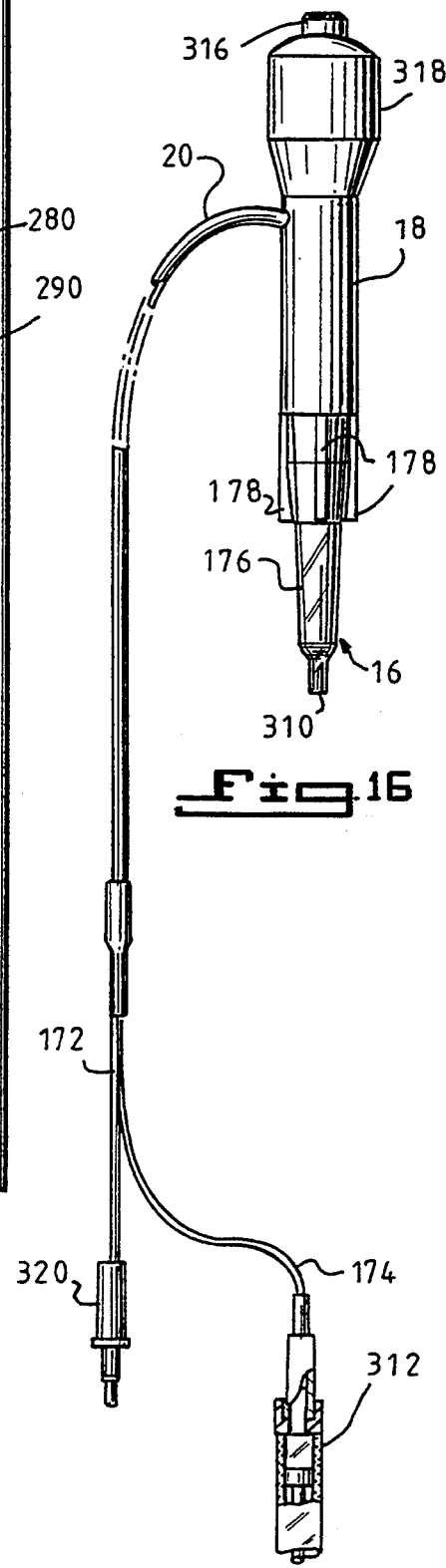

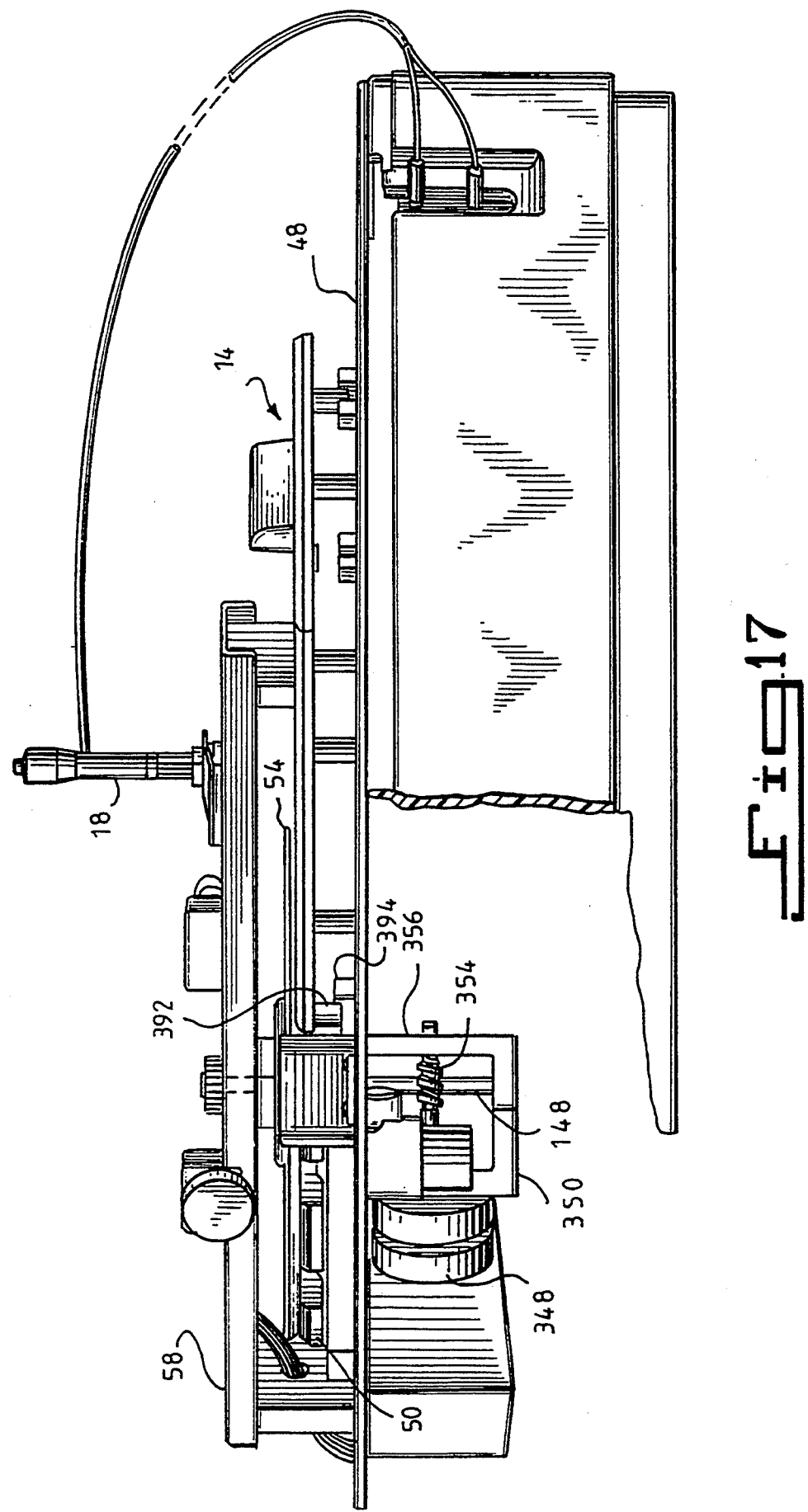

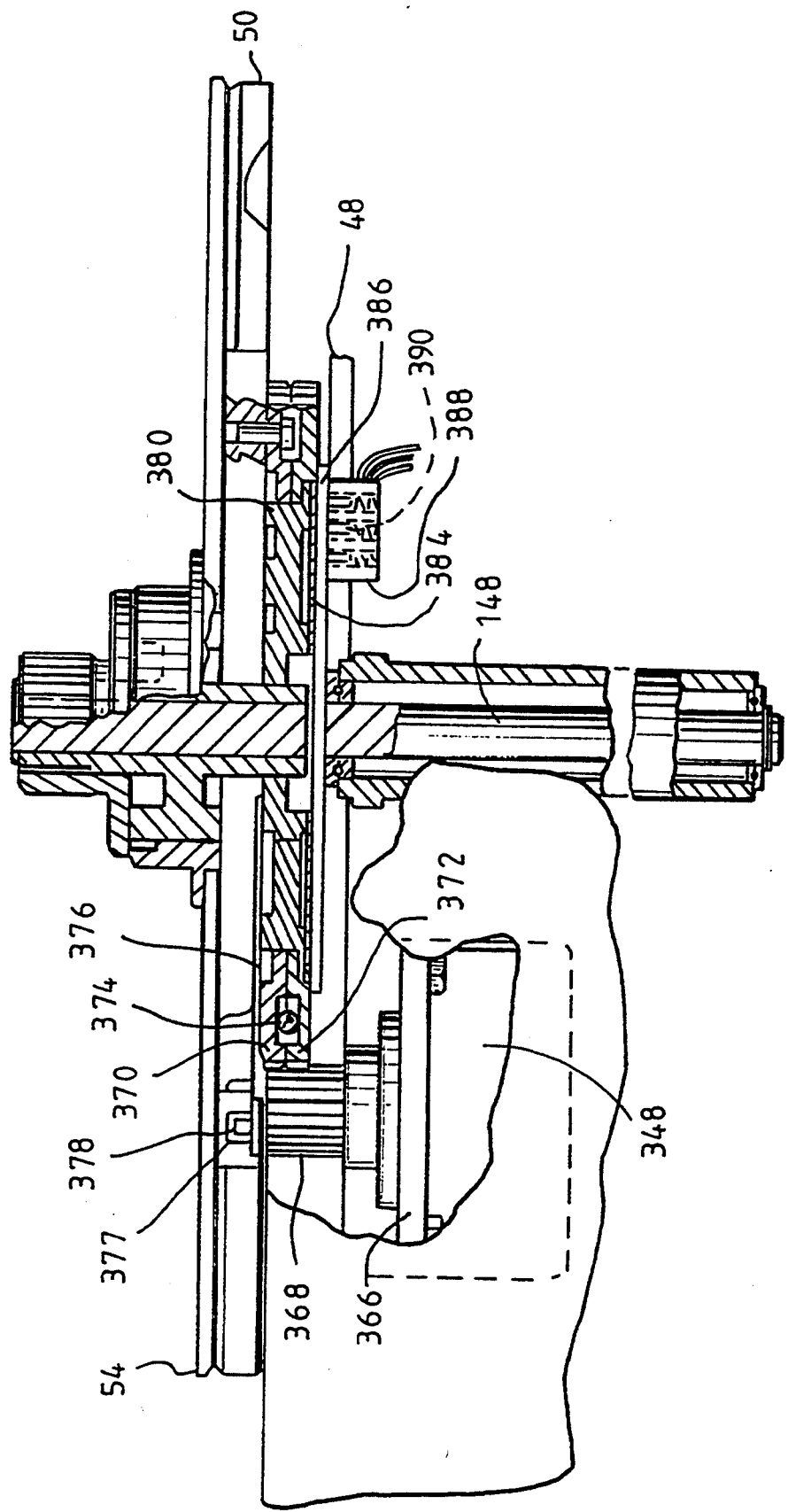

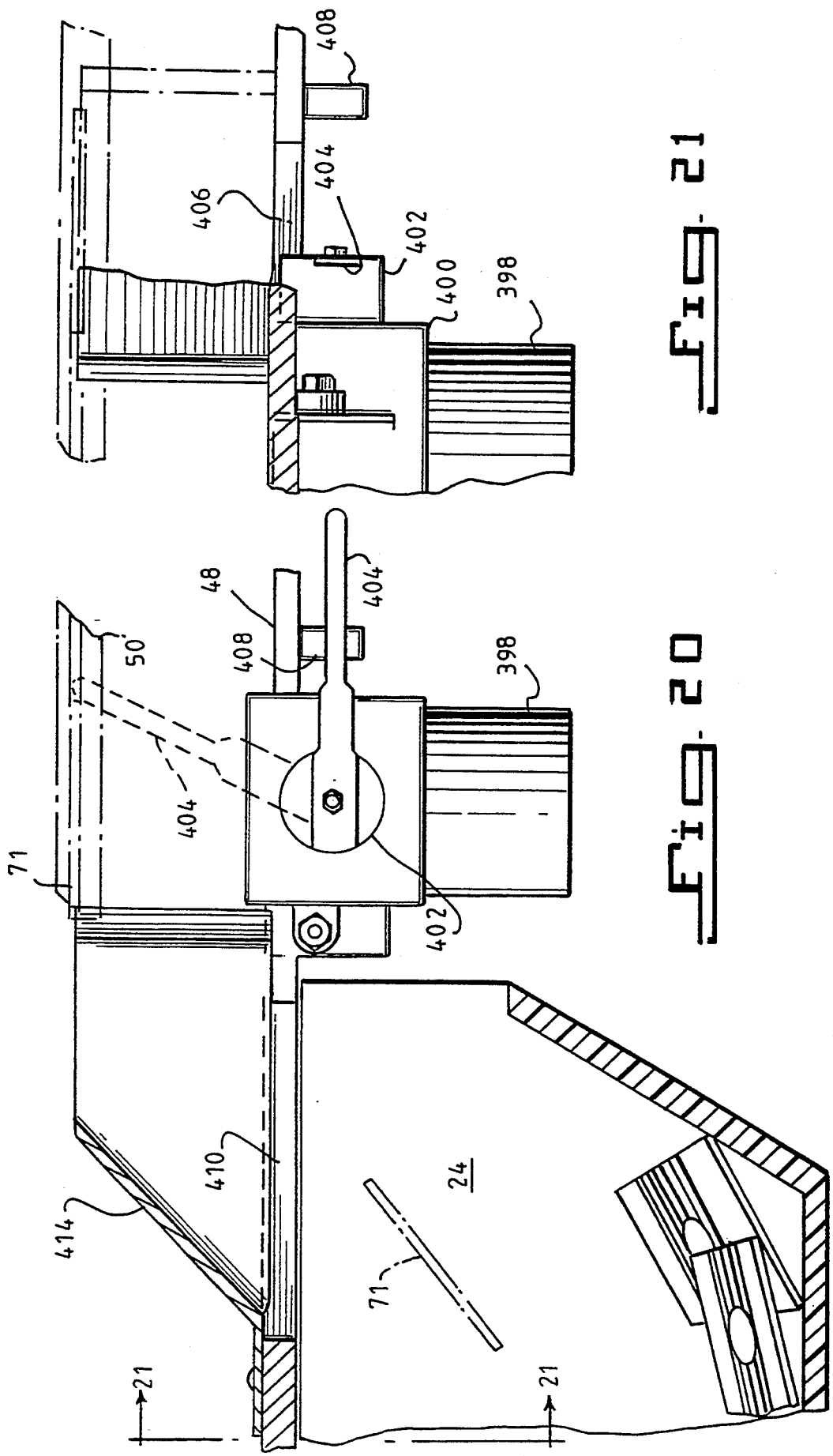

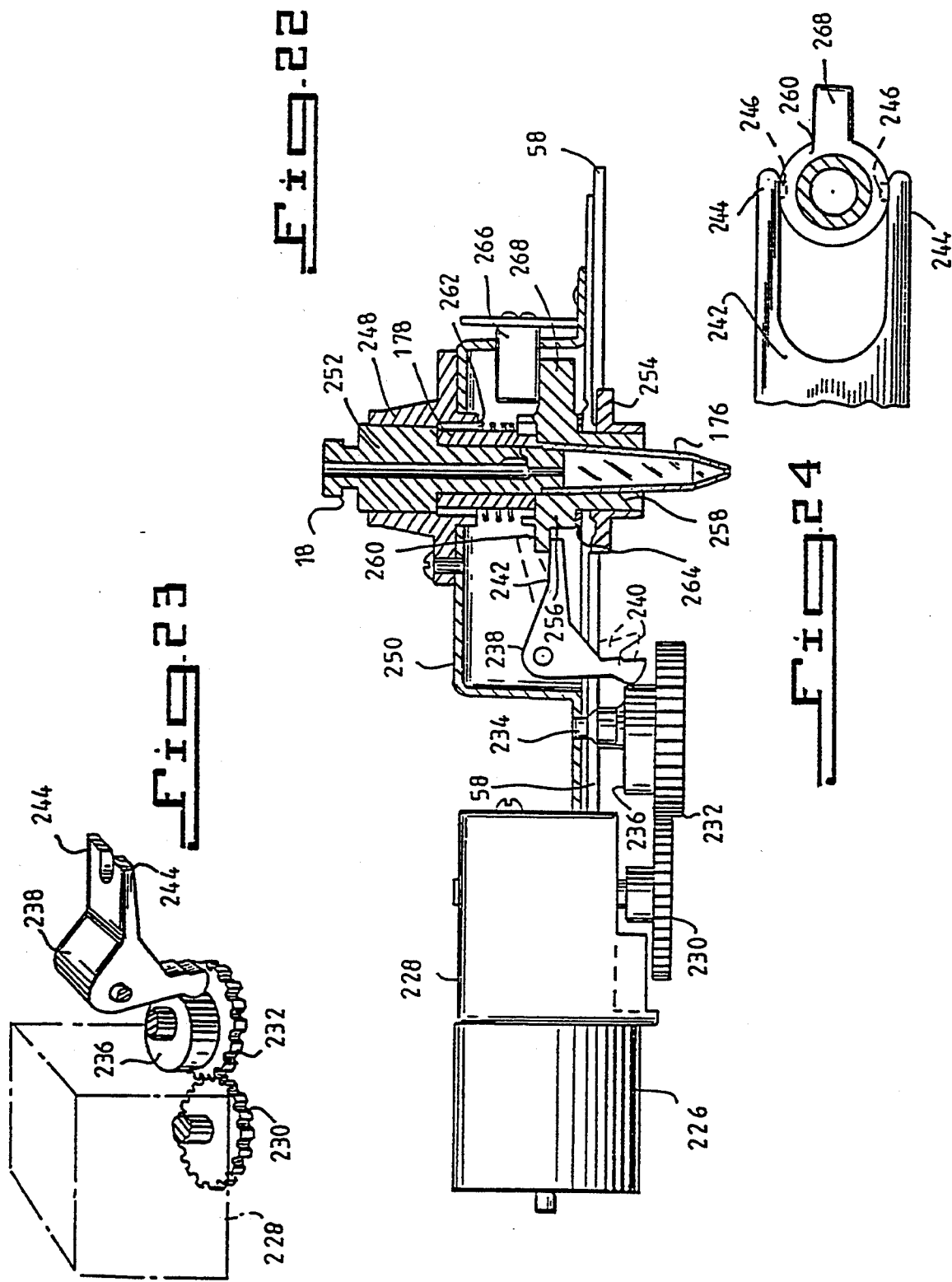

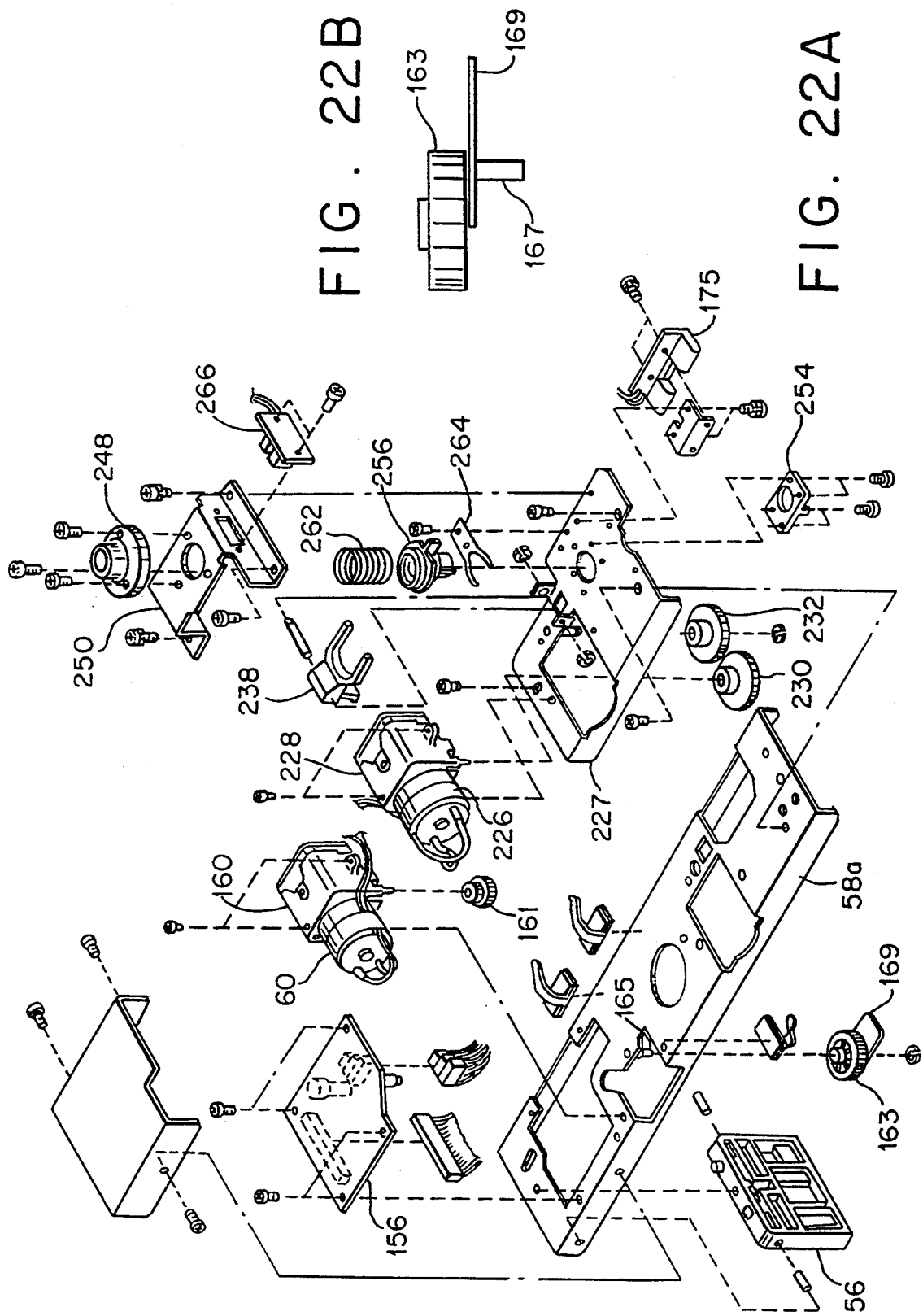

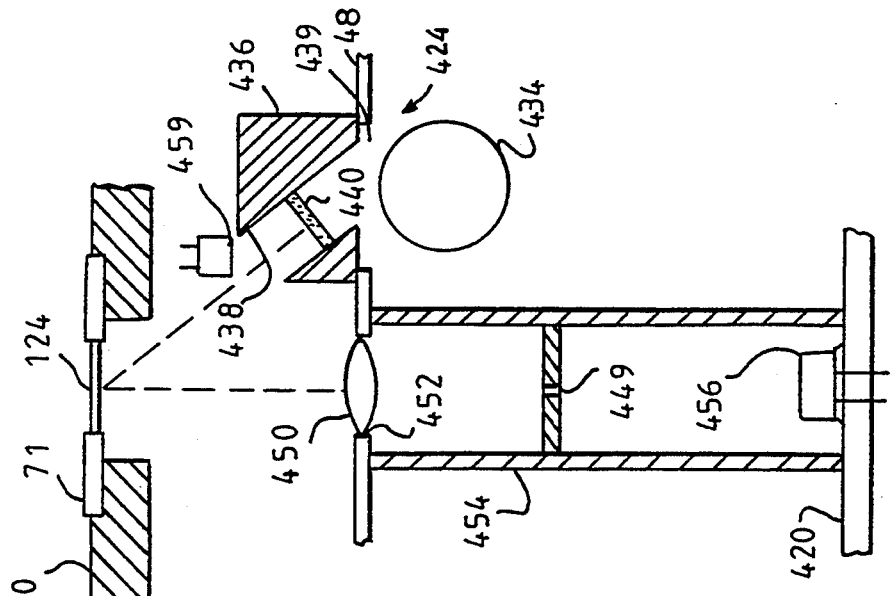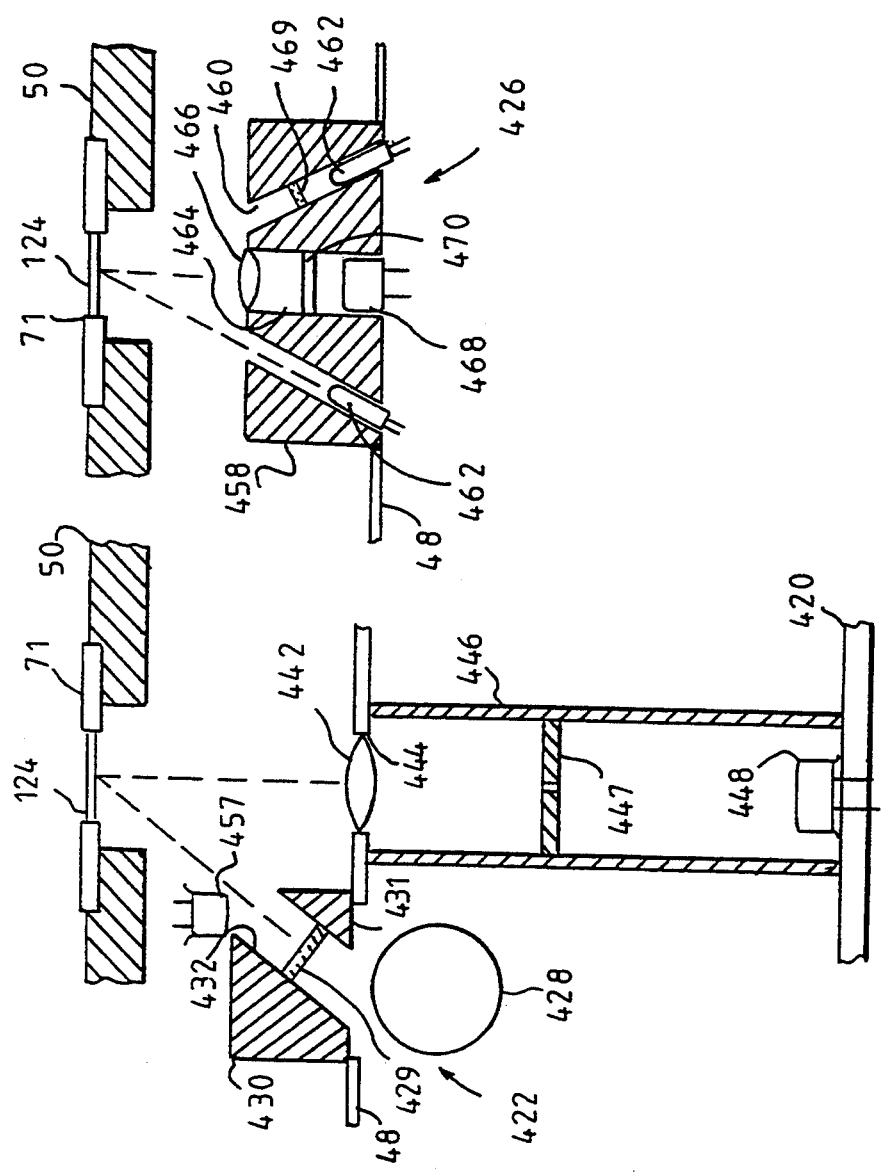

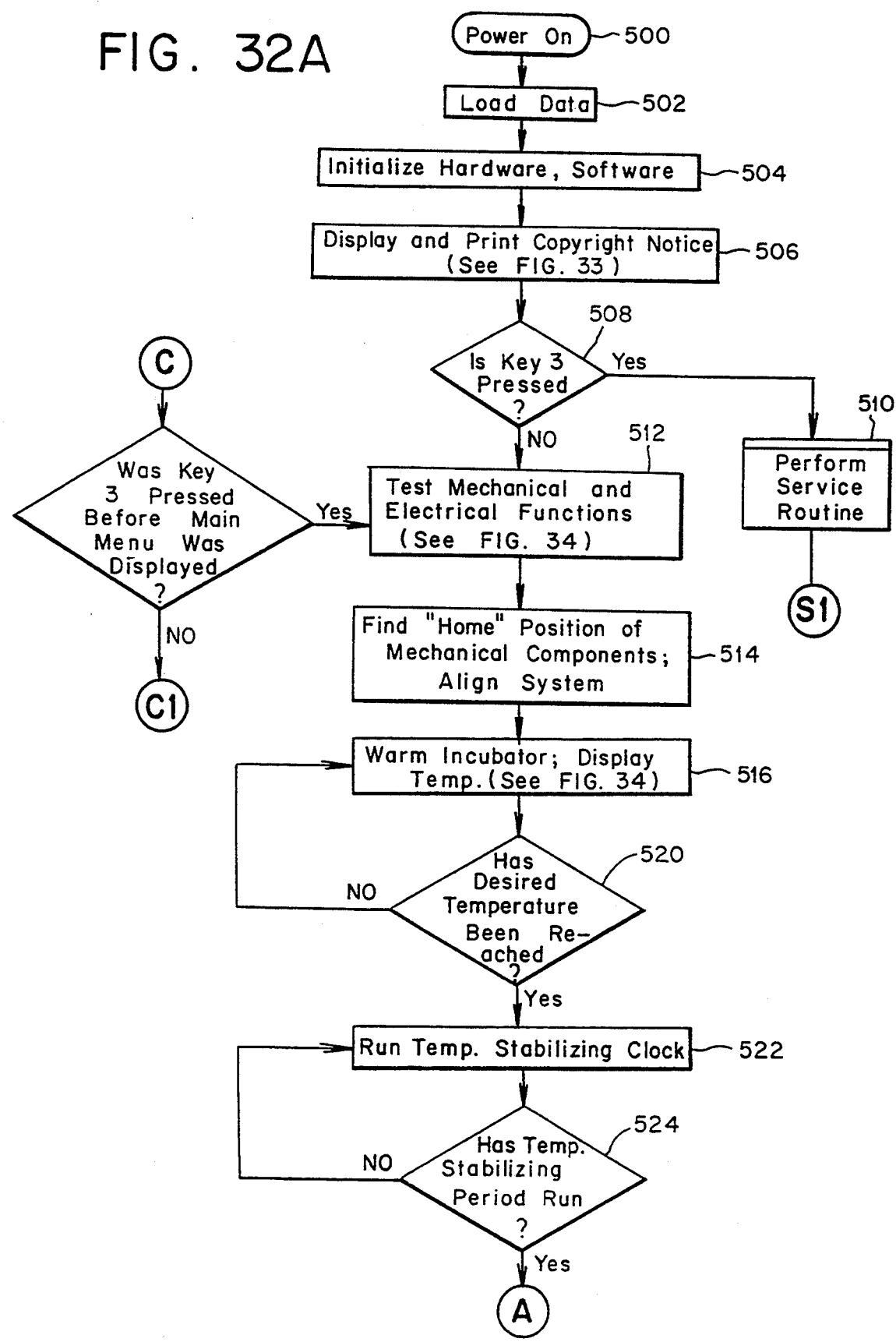

```
Fri        14 Jul 1989    12:56 PM
PAT:       -----------    SPE:-------
************09      Feb  89   13:05

VetTest 8008 -
   Chemistry Analyzer

Copyright Vettest 1989
All rights reserved,
        1989

```
Fri        14 Jul 1989    12:57 PM
PAT:       -----------    SPE:-------

Incubator Warming
Self-test in progress.

-----OPERATING INSTRUCTIONS-----

Please wait.

```
Fri        14 Jul 1989      2:02 PM
PAT:       -----------    SPE:-------
Incubator ready.
Self-test is complete.

----OPERATING INSTRUCTIONS---- press the ENTER key to use
     the analyzer.
```

FIG 35

```
Fri        14 Jul 1989      2:32 PM
PAT:       -----------    SPE:-------

Vet Test Chemistry Analyzer

Main Menu:

1.  Normal operation
   2.  Lot number selection
   3.  Service menu
   4.  Skip analysis operation
   5.  Verbose operation
   6.  Life-test
   7.  Verbose with sub-prespot Enter selection and ENTER:
(use CLEAR to correct entries)
```

FIG 36

```
Fri      14 Jul 1989      3:32 PM
PAT:     -----------      SPE:-------
                press   1   for   DOG
                press   2   for   CAT
                press   3   for   CATTLE
                press   4   for   PIG
                press   5   for   HORSE
                press   6   for   SHEEP
                press   0   for   OTHER

----  OPERATING INSTRUCTIONS  ----

Press CLEAR key to return to
     main menu OR
Press number corresponding to
     species.  If MISTAKE is made,
     press the CLEAR key.
     press the ENTER key.
```

FIG 37

```
Fri   14 Jul 1989          3:51 PM
PAT: 012                SPE: DOG

Insert slides in analyzer.
     (use CLEAR if you wish to
     eject slides and start over)

----  OPERATING INSTRUCTIONS  ----

Put slide in slot.  Push slide
all the way in and pull slide
all the way out.

Repeat this for all slides
     desired.

When all slides are inserted,
     Press the ENTER key.
```

FIG 38

```
SAT  15 Jul 1989          8:48 PM
PAT: 012                  SPE: DOG

Slides being counted
 and previewed
 (Please wait)
If any error, press CLEAR key
 to reload slides.
       ---- OPERATING INSTRUCTIONS ----
incubator diagram
```

| GLU | CA | NH3 | CA | CA | CA |
|-----|----|----|----|----|----|
| CA  | CA | CA |    |    |    |

FIG 39

```
Sat      15 Jul 1989     9:10 AM
PAT:     012             SPE:DOG

Slides counted.

Insert new tip on pipetter.

-----OPERATING INSTRUCTIONS-----

Remove pipetter from analyzer.
Firmly push on unused tip.
Press ENTER key.
```

FIG 40

```
Sat        15 Jul 1989    9:18 AM
PAT:       012            SPE:DOG

Load pipette with sample.

-----OPERATING INSTRUCTIONS-----

Place pipette tip just below
   fluid level of sample.
Then press pipetter button to
   start loading process.
```

FIG 41

```
Sat        15 Jul 1989    9:52 AM
PAT:       012            SPE:DOG

Updrawing serum...

-----OPERATING INSTRUCTIONS-----

Place pipette tip just below
   fluid level of sample.
Then press pipetter button to
   start loading process.
```

FIG 42

```
Sat      15 Jul 1989    9:53 AM
PAT:     012            SPE:DOG

Please lift tip out of serum.

-----OPERATING INSTRUCTIONS-----

Place pipette tip just below
   fluid level of sample.
Then press pipetter button to
   start loading process.
```

FIG 43

```
Sat      15 Jul 1989    10:45 AM
PAT:     012            SPE:DOG

Wipe tip of pipetter and
 replace pipetter to analyzer.
Then press the ENTER key to
 start pipetting and analysis.

-----OPERATING INSTRUCTIONS-----

If any problems with serum
   aspiration, press CLEAR to
   begin again.
```

FIG 44

```
Mon        15 Jul 1989    10:23 AM
PAT:       012            SPE:DOG

Remove and discard pipette tip,
  then press ENTER

-----OPERATING INSTRUCTIONS-----

Remove pipette tip from
  pipetter.
Discard pipette tip.
Replace pipetter in
  analyzer.
Press ENTER key.
```

FIG 47

```
Mon        17 Jul 1989    10:29 AM
PAT:       012            SPE:DOG

Analysis Results:

CA     <      1.4     mg/dl LO      <0.2918>
CA     <      1.4     mg/dl LO      <0.2890>
GLU    <      16      mg/dl LO      <0.0963>
NH3    <      11      umol/l        <0.2440>
CA     <      1.4     mg/dl LO      <0.2510>
CA     <      1.4     mg/dl LO      <0.2796>
CA     <      1.4     mg/dl LO      <0.3229>
CA     <      1.4     mg/dl LO      <0.3427>
CA     <      1.4     mg/dl LO      <0.3424>
```

FIG 48

```
Mon        17 Jul 1989     10:33 AM
PAT:       012             SPE:DOG

Results of this profile
are likely to occur in
following conditions:
01  Hypoparathroidism
02  Chelating Agents (EDTA)
03  Lactation
04  Starvation
05  Pregnancy
06  (Recent prolonged)
 Exercise
07  Insulin Overdose Press ENTER to continue
CLEAR to end, 1 to print
```

FIG 49

```
Mon        17 Jul 1989     10:40 AM
PAT:       -----------     SPE:------

09ALB     6328    67GGT    7356
65ALKP    2005    00GLU    5422
62ALT     2761    63LDH    6430
47AMYL    6415    59LIPA   3750
48AST     6019    32Mg     5555
01BUN     5555    10NA3    7368
03CA      5555    12PHOS   3739
08CHOL    4970    14TBIL   2928
64CK      5523    06TP     5284
18CRSC    7191    07TRIG   3662

111  Print this menu
   100  Return to Main menu
Type selection and ENTER
```

FIG 50

```
Mon        17 Jul 1989     10:48 AM
PAT:       -----------     SPE:-------

Service Menu:
   1.  Set clock
   2.  Instrument Calibration
   3.  Pipetter-only test
   4.  Pipetter life test
   5.  Disk test menu
   6.  Prod. support menu
   7.  LED control
   8.  Service diagnostics
   9.  Return to main menu Enter selection and ENTER:
(use CLEAR to correct entries)
```

FIG 51

```
Mon        17 Jul 1989     1:10 PM
PAT:       -----------     SPE:-------

Service mode:
 Lamp selection:
   1.  Turn on red
   2.  Turn on green
   3.  Turn on yellow
   4.  Turn on deep red
   5.  Turn off all LEDs
   6.  Return to service menu Enter selection and ENTER:
```

FIG 52

```
Mon        17 Jul 1989      1:21 PM
PAT:       ----------       SPE:-------

ONLY PIPETTE TEST please enter number of
spots to updraw
for:
```

FIG 53

```
Mon        17 Jul 1989      1:26 PM
PAT:       ----------       SPE:-------

Slides counted.

Insert new tip on pipetter.

----OPERATING INSTRUCTIONS----

Remove pipetter from analyzer.
Firmly push on unused tip.
Press ENTER key.
```

FIG 54

```
Mon          17 Jul 1989      2:12 PM
PAT:         -----------      SPE:-------

Load pipette and sample.

----OPERATING INSTRUCTIONS----

Place pipette tip just below
    fluid level of sample.
Then press pipetter button to
    start loading process.
```

FIG 55

```
Mon          17 Jul 1989      4:09 PM
PAT:         -----------      SPE:-------

ONLY PIPETTE TEST press pipette button
  for each spot
```

FIG 56

```
Tue        18 Jul 1989      12:54 PM

Set clock:
The current date and time
 are above.

1.  Change day of month
   2.  Change month
   3.  Change year
   4.  Change hours
   5.  Change minutes
   6.  Return to service menu Enter selection and ENTER:
(use CLEAR to correct entries)
```

FIG 57

```
Tue        18 Jul 1989      1:13 PM
PAT:       ----------       SPE:------

Service Diagnostics Menu:
   1.  Cycle articulated pipette
   2.  Turn UV bulbs on
   3.  Turn UV bulbs off
   4.  View/Modify EEPROM
   5.  Dump INSTRUMENT CAL
   6.  Initialize EEPROM
   7.  Set Serial number
   8.
   9.  Return to service menu Enter selection and ENTER:
(use CLEAR to correct entries)
```

FIG 58

```
Tue        18 Jul 1989    1:23 PM
PAT:       -----------    SPE:-------

PIPETTE LIFE TEST

Mark current position.
Press any key to begin.
```

FIG 59

```
Tue        18 Jul 1989    1:34 PM
PAT:       -----------    SPE:-------

PIPETTE LIFE TEST press any key to end
at begin position.
```

FIG 60

```
Tue        18 Jul 1989    1:47 PM
PAT:       -----------    SPE:-------

Slide-disk Diagnostics:
   1.  Set disk home
   2.  Continuous CW
   3.  Continuous CCW
   4.  Disk life test
   5.  Cover open
   6.  Cover close
   7.  Eject at current location
   8.  Move slide disk
   9.  Return to service menu Enter selection and ENTER:
(use CLEAR to correct entries)
```

FIG 61

```
Tue        18 Jul 1989    1:56 PM
PAT:       -----------    SPE:-------

Production diagnostics:
   1.  Read A/D channels
   2.  Load slides
   3.  R.D. test
   4.  Eject all slides
   5.  Table home sense change
   6.  Keypad change
   7.  Cover home sense change
   8.
   9.  Return to service menu Enter selection and ENTER:
(use CLEAR to correct entries)
```

FIG 62

```
Tue         18 Jul 1989    2:02 PM
PAT:        -----------    SPE:-------

Instrument calibration menu:
  1.  Read visible white slides
  2.  Read visible black slides
  3.  Read UV white slides
  4.  Read UV black slides
  5.  Enter visible reflectances
  6.  Enter UV reflectances
  7.  Calc black and white refs
  8.  Save refs and return
  9.  Exit without saving refs Enter selection and ENTER:
(use CLEAR to correct entries)
```

FIG 63

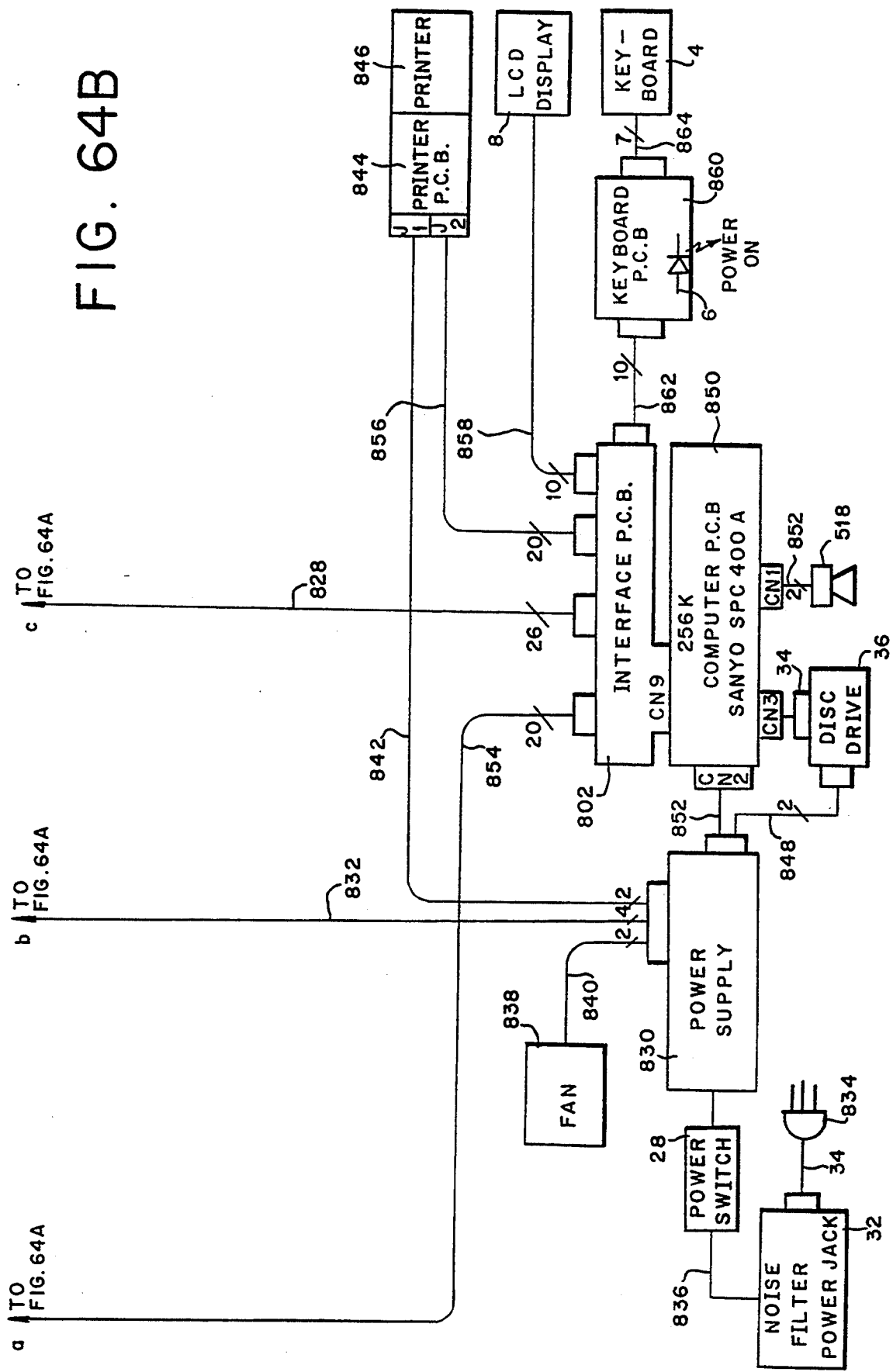

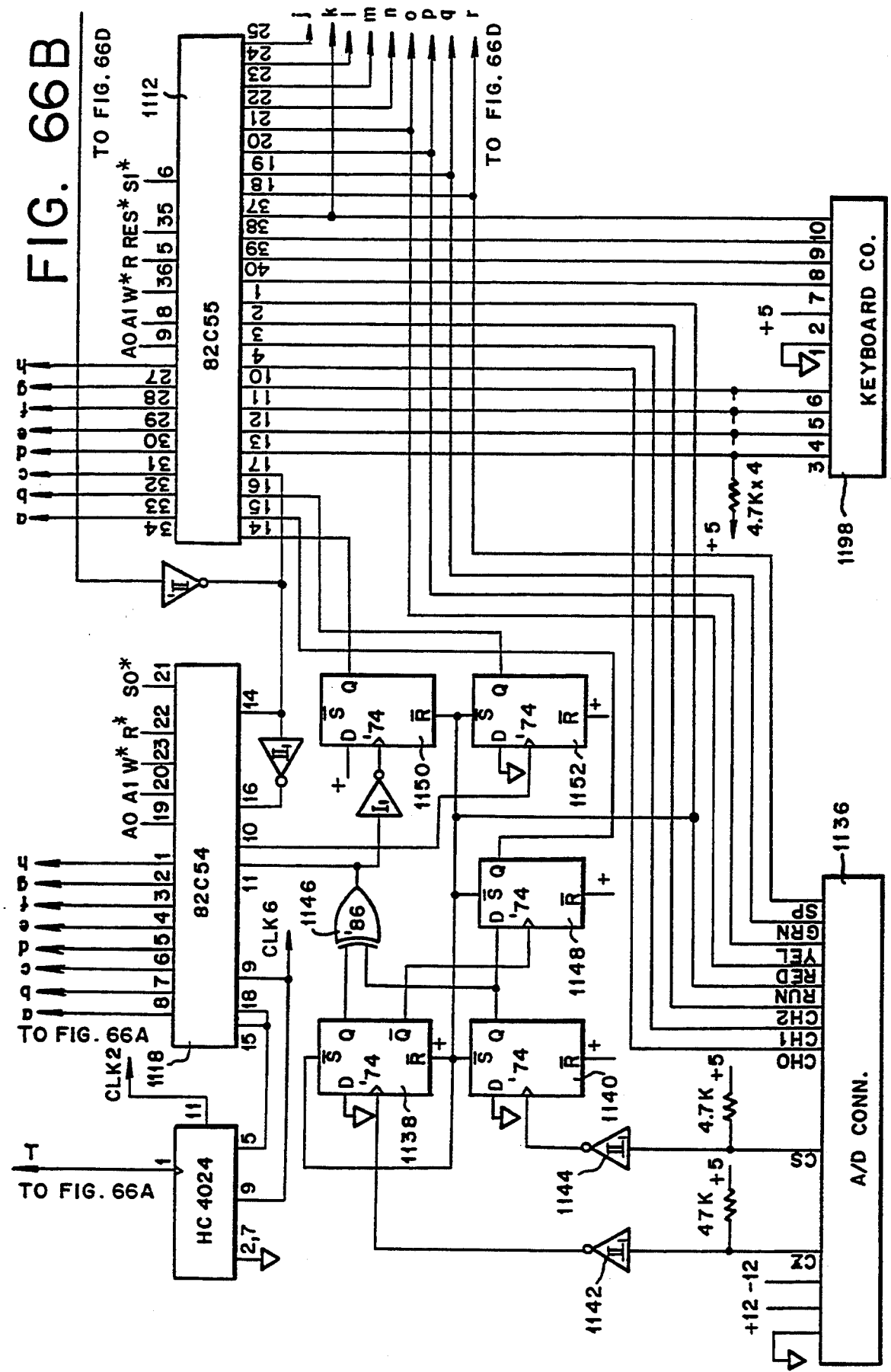

CHEMICAL ANALYZER

This application is a division of U.S. application Ser. No. 07/806,071, filed Dec. 6, 1991, now U.S. Pat. No. 5,250,262, which is a continuation of U.S. application Ser. No. 07/441,451, filed Nov. 22, 1989, now U.S. Pat. No. 5,089,229.

BACKGROUND OF THE INVENTION

1. Field of the Invention

This invention relates to the chemical analysis of substances, and more particularly relates to apparatus for the automatic analysis of biological fluids. Even more specifically, this invention relates to medical testing devices particularly adapted for veterinary testing purposes wherein a change in an optical characteristic of a sample is sensed and analyzed automatically by the device.

Increasingly, the population has relied upon competent medical assistance to solve individual medical problems to a greater and greater extent. This factor, coupled with the ever growing wealth of medical knowledge, has resulted in a vast upsurge in the number of tests of various types performed as part of the diagnosis or health monitoring process. As a result, there is an increasing need for apparatus for performing such tests in an inexpensive fashion, which apparatus can be operated by relatively unskilled personnel and which will eliminate most opportunities for unreliability of results due to human error.

2. Description of the Prior Art

In recent years, a number of automated systems have been developed for carrying out quantitative chemical analysis of fluid samples. Many of the commercially available systems utilize liquid reagents and require analyzer equipment having intricate solution handling and transport capabilities. Such equipment can be referred to as "wet chemistry" analyzers. For example, U.S. Pat. No. 3,788,816, which issued to D. G. Rohrbaugh et al., discloses a liquid analysis system in which a turntable carries a plurality of receptacles containing samples to be analyzed and a plurality of tube modules which are adapted to receive preset volumes of sample and reagent. Coaxially disposed relative to the turntable is a vertically movable rotary element comprising a probe tip which serves to dispense reagents and to transfer sample to a spectrophotometer.

Wet chemistry analyzers, such as described above, are usually complex and expensive, require skilled operators and necessitate a considerable expenditure of time and effort in repetitive cleaning operations.

As an alternative to liquid analysis systems, various analyzers have been developed for automated test procedures involving essentially dry, analytical elements, which elements offer substantial storage and handling conveniences when compared to "wet chemistry" instruments.

The "dry" analytical elements are preferably in the form of test slides. The test slides are formed as a multi-layer element containing the necessary reagents for reaction with components of a biological fluid, such as blood serum, deposited thereon. Certain reactions colorimetrically produce a change in optical density which is sensed by a reflectometer or other device, the amount of light reflected from the element varying in accordance with the reaction and being indicative of the amount of a particular component present in the fluid.

In a typical chemical analyzer, such as described in U.S. Pat. No. 4,296,070, which issued to Michael S. Montalto et al., the slides, which are essentially planar and contain reagents in dry form, are loaded into a cartridge and fed from the cartridge into a metering station where a predetermined amount of sample fluid is deposited on the analysis slide.

After an appropriate incubation period, the slide is moved to an analysis station where a change in the slide is sensed, the amount of change being proportional to a particular analyte in the sample fluid. The slide is used only once and is discarded after the reading is taken.

OBJECTS AND SUMMARY OF THE INVENTION

It is an object of the present invention to provide a chemical analyzer in the form of a small, desktop unit.

It is another object of the present invention to provide a chemical analyzer which can run a series of tests simultaneously in a relatively short period of time. It is still another object of the present invention to provide a chemical analyzer which is relatively inexpensive to manufacture and has a relatively low operating cost.

It is a further object of the present invention to provide a chemical analyzer which may be easily partially disassembled to facilitate cleaning.

It is yet a further object of the present invention to provide a chemical analyzer whose components are tolerant of considerable variation in slide thickness.

It is yet another object of the present invention to provide a chemical analyzer with a relatively simplified optical head for spectrophotometric analysis of slides.

It is still a further object of the present invention to provide a chemical analyzer with a simplified turntable mechanism for transporting analytical test slides as well as a turntable cover for controlling evaporation.

It is still a further object of the present invention to provide a chemical analyzer which includes an incubator having an analog heater control providing an accurate control of the temperature of the slides.

It is still a further object of the present invention to provide a chemical analyzer which includes a spectrophotometer incorporating small size, relatively low cost, high production components.

It is another object of the present invention to provide a chemical analyzer having a slide analysis portion which provides high resolution and good short-term stability.

It is a further object of the present invention to provide a chemical analyzer which provides real time information to the user as the tests are being run.

It is yet another object of the present invention to provide a chemical analyzer which includes a metering device which can dispense fluids with high accuracy and is relatively inexpensive to manufacture.

It is yet a further object of the present invention to provide a chemical analyzer having a metering device which can provide accurate drop volumes despite varying test slide thicknesses.

It is still a further object of the present invention to provide a chemical analyzer in which test results are analyzed according to species and out of normal bounds are flagged.

It is another object of the present invention to provide a chemical analyzer which automatically analyzes the results of tests conducted by the analyzer, indicates potential problems to the user and provides guidance as to the possible diseases or ailments which may have caused abnormal readings.

It is still a further object of the present invention to provide a method of analyzing an analytical test slide, of metering a predetermined volume of sample onto the test slide, of maintaining the test slide at a constant temperature, and of transporting the test slide through an analyzer apparatus.

It is yet a further object of the present invention to provide a method of metering relatively small volumes of sample onto an analytical test slide.

In accordance with one form of the present invention, the chemical analyzer comprises a transport mechanism which includes a rotating turntable adapted to hold a plurality of reagent test slides, a sample metering device, an incubator or temperature controller, a reflectometer (or spectrophotometer) and associated electronics and software.

The rotating turntable preferably holds up to twelve slides about its circumference, which slides are loaded onto the turntable by an inserter mechanism. The turntable positions the reagent test slides under the metering device, which device deposits a predetermined amount of sample onto each slide. The turntable also carries the slides above a reflectometer. After testing has been completed, an ejector mechanism automatically removes the reagent slides from the turntable.

The sample metering device includes a pipette assembly which holds a certain amount of sample in its tip. A pump provides air pressure to the pipette to force a predetermined amount of sample from the tip. The pipette assembly is adapted to move vertically downwardly to approach the slide and deposit a quantity of sample on each slide.

The incubator or heat controller of the analyzer includes a heating device, as well as a temperature sensor coupled to the rotating turntable. The turntable and the slides mounted on the turntable are maintained at a specific temperature prior to and during the analysis process. A cover is mounted on the turntable and covers the slides in order to minimize evaporation.

The reflectometer incorporates light emitting diodes (LEDs) and ultraviolet fluorescent tubes as the light sources, which sources may be individually operated, depending upon the type of test being performed. A sensor (for example, a photodiode) receives the light reflected by the reagent slide, which sensor provides a voltage to the electronic circuitry of the analyzer.

The electronic circuitry includes a computer, an analog-to-digital (A/D) converter and interface circuits. A keyboard is provided for inputting information and for controlling the operation of the analyzer. A display provides test results and operational instructions to the user.

These and other objects, features and advantages of the present invention will be apparent from the following detailed description of illustrative embodiments thereof, which is to read in connection with the accompanying drawings.

BRIEF DESCRIPTION OF THE DRAWINGS

FIG. 1 is a front perspective view of a chemical analyzer formed in accordance with one form of the present invention.

FIG. 2 is a rear perspective view of the chemical analyzer shown in FIG. 1.

FIG. 3 is a front perspective view of the chemical analyzer shown with the cover removed.

FIG. 4 is a top view of a portion of the chemical analyzer, showing a slide inserter mechanism.

FIG. 5 is a front view of the slide inserter mechanism shown in FIG. 4.

FIG. 6 is a top view of the slide inserter mechanism shown in FIG. 4 illustrating the inserter mechanism carrying a test slide.

FIG. 7 is a perspective view of the inserter mechanism.

FIG. 8 is a partial perspective view of the turntable and cover of the chemical analyzer.

FIG. 8A is an exploded view, in perspective, of an alternative form of the turntable and cover.

FIG. 9 is a sectional view of the turntable and cover taken along line 9—9 of FIG. 8.

FIG. 9A is a sectional view of the turntable and cover and inserter mechanism, prior to a slide being received by the turntable.

FIG. 9B is a sectional view of the turntable and cover, illustrating the test slide being received by the turntable.

FIG. 10 is a top view partially broken away of the turntable and cover illustrating how the test slides are received by the turntable.

FIG. 10A is a top view partially broken away of the cover and turntable illustrating the position of the test slide before and after it is received by the turntable.

FIG. 10B is a front view of the turntable and cover and test slide shown in FIG. 10A.

FIG. 11 is a perspective view of a portion of the analyzer in a raised and unraised position.

FIG. 12 is a partial sectional view of a portion of the analyzer illustrated by FIG. 11, taken along line 12—12 of FIG. 11.

FIG. 13 is a sectional view of a portion of the analyzer shown in FIG. 12, taken along line 13—13 of FIG. 12.

FIG. 13A is a front view of one form of a metering device used in the chemical analyzer of the present invention.

FIG. 13B is an enlarged view of a portion of the metering device shown in circle 13B of FIG. 13A.

FIG. 13C is a top view of the metering device shown in FIG. 13A.

FIG. 13D is a top view of the metering device shown in FIG. 13A.

FIG. 13E is a front view of the metering device, formed in accordance with a second embodiment of the present invention.

FIG. 13F is a perspective view of a portion of the metering device illustrated by FIG. 13E.

FIG. 15 is a bottom view of the metering assembly of the chemical analyzer.

FIG. 16 is a perspective view of a portion of the metering assembly.

FIG. 17 is a front perspective view partially broken away illustrating the drive assembly for the turntable of the chemical analyzer.

FIG. 19 is a perspective view of an alternate form of the turntable drive mechanism.

FIG. 20 is a side view of a slide ejector mechanism used in the chemical analyzer of the present invention.

FIG. 21 is a front view of the ejector mechanism shown in FIG. 20.

FIG. 22 is a side elevational view, partially in section, of an alternative embodiment of a metering device used in the analyzer of the present invention.

FIG. 22A is an exploded view, in perspective, of an alternative embodiment of a cover opening mechanism and of the metering device shown in FIG. 22.

FIG. 22B is a side view of a portion of the cover opening mechanism.

FIG. 23 is a perspective view of a portion of the metering device of FIG. 22.

FIG. 24 is a top elevational view of a portion of the metering device of FIG. 22.

FIG. 31A is a cross-sectional view of a first portion of the reflectometer assembly of the present invention.

FIG. 31B is a cross-sectional view of a second portion of the reflectometer assembly of the present invention.

FIG. 31C is a cross-sectional view of a third portion of the reflectometer assembly of the present invention.

FIG. 32A-M is a flowchart of the operation of the analyzer of the present invention.

FIG. 33 is a front view of the display of the analyzer and information displayed thereon.

FIG. 34 is a front view of the display of the analyzer and information displayed thereon.

FIG. 35 is a front view of the display of the analyzer and information displayed thereon.

FIG. 36 is a front view of the display of the analyzer and information displayed thereon.

FIG. 37 is a front view of the display of the analyzer and information displayed thereon.

FIG. 38 is a front view of the display of the analyzer and information displayed thereon.

FIG. 39 is a front view of the display of the analyzer and information displayed thereon.

FIG. 40 is a front view of the display of the analyzer and information displayed thereon.

FIG. 41 is a front view of the display of the analyzer and information displayed thereon.

FIG. 42 is a front view of the display of the analyzer and information displayed thereon.

FIG. 43 is a front view of the display of the analyzer and information displayed thereon.

FIG. 44 is a front view of the display of the analyzer and information displayed thereon.

FIG. 47 is a front view of the display of the analyzer and information displayed thereon.

FIG. 48 is a front view of the display of the analyzer and information displayed thereon.

FIG. 49 is a front view of the display of the analyzer and information displayed thereon.

FIG. 50 is a front view of the display of the analyzer and information displayed thereon.

FIG. 51 is a front view of the display of the analyzer and information displayed thereon.

FIG. 52 is a front view of the display of the analyzer and information displayed thereon.

FIG. 53 is a front view of the display of the analyzer and information displayed thereon.

FIG. 54 is a front view of the display of the analyzer and information displayed thereon.

FIG. 55 is a front view of the display of the analyzer and information displayed thereon.

FIG. 56 is a front view of the display of the analyzer and information displayed thereon.

FIG. 57 is a front view of the display of the analyzer and information displayed thereon.

FIG. 58 is a front view of the display of the analyzer and information displayed thereon.

FIG. 59 is a front view of the display of the analyzer and information displayed thereon.

FIG. 60 is a front view of the display of the analyzer and information displayed thereon.

FIG. 61 is a front view of the display of the analyzer and information displayed thereon.

FIG. 62 is a front view of the display of the analyzer and information displayed thereon.

FIG. 63 is a front view of the display of the analyzer and information displayed thereon.

FIG. 64A-B is a block diagram of the associated electronic circuitry of the analyzer

FIG. 66A-D is a schematic diagram of a second portion of the electronic circuitry of the analyzer.

DETAILED DESCRIPTION OF THE PREFERRED EMBODIMENTS

Figure 7A:
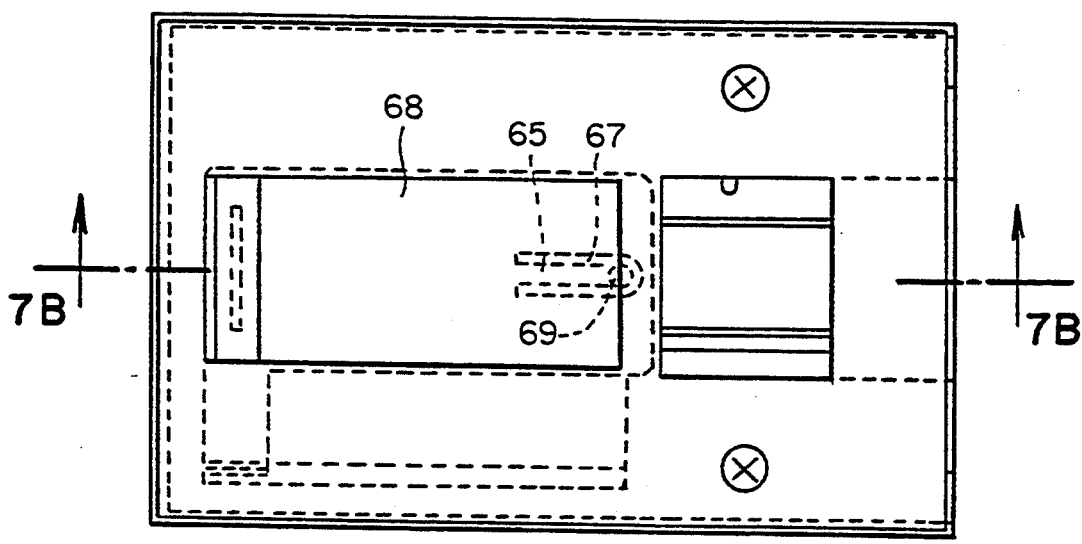
FIG. 7A is a top planar view of another embodiment of the slide inserter.

Referring initially to FIG. 1 of the drawings, it will be seen that a chemical analyzer 2 formed in accordance with the present invention is a compact, desktop unit which weighs about thirty pounds. The overall dimensions of the chemical analyzer are approximately 7" in height 19" in width, and 14" in depth Because the unit is relatively small and lightweight, it is quite portable and may be set up conveniently on a desk or table, requiring very little space.

As can be seen from FIG. 1, the chemical analyzer 2 preferably includes a keyboard 4 for entering information and instructions to the analyzer. The keyboard 4 is preferably flush-mounted on the analyzer body, and is completely sealed and water impermeable to allow the analyzer to be easily cleaned and to prevent any malfunctions in the event that a liquid is inadvertently spilled on the keyboard.

The chemical analyzer includes a Power On indicator 6, and a display 8, which is preferably a liquid crystal display. The display 8 provides the user with diagnostic information as well as with instructions relating to the operation of the analyzer.

The chemical analyzer further includes a printer 10 so that diagnostic information and test results may be displayed in hard copy on the printer paper 11.

The chemical analyzer further includes a cover 12 which is removable to allow access to the internal mechanisms of the analyzer. As will be seen, the cover 12 protects the analyzer from dust and other contaminants which may affect the operation of the analyzer and from external light which may affect the chemical analysis.

The chemical analyzer is particularly adapted to accept test slides containing a dry analyte. Such test slides are well known in the art and are described in U.S. Pat. No. 4,647,431, which issued to Takasi, Sekine, et al.

The chemical analyzer 2 includes a slide inserter 14 which, as its name implies, is used to insert clean test slides into the analyzer. After the slides are inserted into the analyzer, a predetermined amount of serum to be analyzed will be deposited onto the test slide.

Accordingly, the chemical analyzer further includes a metering device which is shown in FIG. 1 as including a pipette assembly 16. The pipette assembly 16 includes a pipette 18 and a pipette tube 20 which interconnects the pipette to the rest of the analyzer through a connector 22. The pipette 18 is received in an opening 23 formed in the top of the cover 12 and extends partially into the analyzer.

After the chemical analyzer has completed its test of the slides, they are ejected by the analyzer into a slide tray 24. The slide tray 24 is mounted flush with the front side wall 26 of the analyzer and is slidable so that the test slides may be removed and discarded. The operation of all of the components described above in relation to FIG. 1 will again be described in greater detail.

FIG. 2 shows the back of the analyzer 2 in its preferred form. As can be seen from FIG. 2, the chemical analyzer includes an On/Off switch 28 which controls power to the analyzer, a standard male receptacle 30 which receives the mating female connector 32 of a grounded power line cord 34, and a disk drive assembly and reader 36 for receiving a 3½ inch computer floppy disk. The floppy disk has stored on it not only software information which controls the operation of the analyzer but also management information, such as data logging, the number of slides which have been used by the machine leasing information (if the chemical analyzer is leased), etc.

As shown in FIG. 2, there are preferably three connectors located on the rear wall 38 of the chemical analyzer housing. The first connector 40 is a KBD type connector. It allows the chemical analyzer to interface with an external alphanumeric keyboard so that additional information in the form of alphanumeric characters may be provided to the analyzer and printed out by the printer 10 for record keeping purposes. As can be seen from FIG. 1, the keyboard 4 provided on the analyzer is rather simple and uncomplicated; however, this keyboard may be substituted with a more versatile alphanumeric keyboard, such as the one which is envisioned to be used externally and interfaced with the first connector 40.

The second connector 44 is a typical serial computer interface connector. This connector is provided for expansion purposes, for example, if the chemical analyzer is to be connected to a modem so that information may be transmitted to a central monitoring station.

The third connector 42 which is provided on the back of the chemical analyzer is adapted to plug into an external printer.

FIG. 3 illustrates the chemical analyzer 2 with its housing cover 12 removed (but shown in phantom), which cover is normally secured to the analyzer by a plurality of posts 46 mounted on an internal base plate 48, which posts engage resilient clips (not shown) mounted on the inside surfaces of the housing cover.

As can be seen from FIG. 3, under the cover is mounted a rotatable turntable 50. The turntable 50 includes a plurality of recesses or receiving slots 52 (shown in FIG. 10A) formed in its upper surface which are adapted to receive test slides. As will be explained in greater detail, the slide inserter 14 is aligned radially with the receiving slots 52 of the rotatable turntable so that the inserter can push a test slide into a corresponding receiving slot on the rotatable turntable 50.

A cover 54 is also provided to minimize evaporation of a serum or other liquid which is deposited onto the test slide for analysis. The cover 54 is mounted on the rotatable turntable 50 and is adapted to reciprocatingly slide clockwise and counter-clockwise over the rotatable turntable to cover and uncover portions of the test slides carried by the turntable.

Two upright supports 56 are mounted on the base plate 48 on diametrically opposite sides of the rotatable turntable 50. A bridge bracket 58 is mounted on the two upright supports 56 and extends across the top of the rotatable turntable 50 and cover 54. The bridge bracket 58 supports a drive motor 60 which is provided for opening and closing the cover 54 (i.e., rotating the cover counter-clockwise and clockwise with respect to the rotatable turntable) 50, as well as another drive motor 62 which, as will be described in greater detail, provides a reciprocating vertical movement to the pipette 18 during the metering operation.

The rotatable turntable 50 transports the test slides which are spotted with a serum to be analyzed past a spectrophotometer a portion 64 of which is shown in FIG. 3

FIGS. 1-3 and the foregoing explanation provide a general description of the chemical analyzer of the present invention. The structure and operation of the analyzer will now be described in greater detail.

THE SLIDE INSERTER MECHANISM

FIGS. 4-7 show the preferred structure of the slide inserter mechanism 14 and its relative position with respect to the rotatable turntable 50.

As mentioned previously, the test slides are manually fed to the rotatable turntable by use of the slide inserter 14. The slide inserter 14 basically includes three components: a guide plate 64, a cover plate 66 secured to the guide plate 64 and superposed on the guide plate, and a slide inserter plate 68. The slide inserter plate 68 is interposed between the cover plate 66 and the guide plate 64.

More specifically, a portion of the upper surface of the guide plate 64 is recessed to define a track 70 which extends generally longitudinally in the guide plate. The track 70 has a width which is slightly greater than that of a test slide so that a test slide may be received in the track for loading into the turntable 50. In addition, the guide plate 64 includes a slot 72 which is formed through its thickness, which slot extends in a parallel direction to the track 70 formed in the surface of the guide plate.

The inserter plate 68 has a main body portion 74 which is dimensioned to be received by the track 70 formed in the guide plate 64, and an arm 76 which extends from a side of the main body portion 74 The arm 76 is L-shaped, that is it includes a leg portion 78 which extends downwardly out of the plane in which the inserter plate primarily resides. This downward leg 78 of the arm extends through the slot 72 formed in the guide plate 64.

The inserter plate 68 further includes a grip 80 which extends upwardly from the top surface of the inserter plate and is mounted at the end of the main body 78 of inserter plate which is the most distant end from the rotatable turntable 50 when the slide inserter is properly positioned in the analyzer. The grip 80 allows a user to slide the inserter plate 68 reciprocatingly within the track 70 formed in the guide plate, in order to insert a slide in the rotatable turntable 50, as will be described.

The cover plate 66 is mounted over the guide plate 64 and secures the inserter plate 68 in place between the two and in its proper position within the track 70 formed in the guide plate. The cover plate 66 includes an elongated slot 82 formed through its thickness. The grip 80 of the inserter plate extends upwardly through this slot 82, and the slot is dimensioned to allow the grip 80 of the inserter plate to move longitudinally in the slot 82.

The cover plate 66 further includes a rectangular cutout 84 again formed through its thickness. The cutout 84 is dimensioned to be slightly larger than the peripheral dimensions of a test slide 71 so that a test slide may be inserted through the cutout and into the track 70 formed in the guide plate 64.

As shown in FIG. 7, the test slide 71 which is envisioned to be used with the chemical analyzer of the present invention includes a bar code 86 printed on one surface. The bar code 86 includes information concerning what type of analyte is contained on the test slide. The bar code 86 is read by the chemical analyzer, which uses this information in analyzing the test results.

The test slide 71 must be placed in a predetermined position so that the bar code 86 may be read by the analyzer and so that it may be properly received by the rotatable turntable 50. Accordingly, the slide inserter 14 may further include a slide orientation plate 88 mounted on the cover plate 66. The slide orientation plate 88 includes a slot 90 formed through its thickness having substantially the same dimensions and being aligned with the cutout 84 formed in the cover plate.

However, the slide orientation plate 88 further includes a tab 92 which extends into the slot 90 from one side. The tab 92 is adapted to align with a notch 94 (see FIG. 6) formed in a side of the conventional test slide 71. Accordingly, the user will know that the test slide 71 is properly placed in the slide inserter 14 when the notch 94 of the slide is aligned with the tab 92 on the slide orientation plate 88. Alternatively, the slot 90 and tab 92 may be formed directly in the cover plate 66 and the slide orientation plate 88 may be omitted.

As shown in FIGS. 4 and 5, the slide inserter 14 is supported above the base plate 48 of the analyzer by a plurality of stand-offs 96. The height of the slide inserter 14 is chosen to be comparable to that of the receiving slots 52 formed in the rotatable turntable 50. In this manner, slides 71 may be transferred from the slide inserter 14 to a corresponding receiving slot formed in the rotatable turntable, this action occurring in a single plane. The longitudinal axis of the slide inserter 14 is radially aligned with the rotatable turntable 50, and in particular with each corresponding receiving slot 52, of the turntable as the turntable rotates, to position a receiving slot adjacent to the end 98 of the slide inserter which is proximate to the turntable 50.

In its most fully retracted position, the inserter plate 68 allows a test slide 71 to be placed on the track 70 formed in the guide plate through the cutout 84 formed in the cover plate 66. The free end 100 of the main body of the inserter plate 68 will engage an edge of the test slide 71 when the inserter plate is moved to a forward position (i.e., towards the turntable) with respect to the guide plate 64. The inserter plate 68 will push the test slide out of the proximate end 98 of the slide inserter and into a corresponding receiving slot 52 positioned in alignment with the slide inserter 14.

Two optical sensors 101, 103 are associated with the slide inserter 14. The first optical sensor 101 includes a first pair of an LED light source 102 and a photodetector (ex., phototransistor) 104 spaced apart from each other and extending upwardly through an opening 106 formed through the thickness of the base plate 48. Similarly, the second optical sensor 103 includes a second pair of a light source 108 and photodetector 110, also spaced apart from each other, which extend upwardly through a second opening 112 formed in the base plate. The first and second pairs are separated from each other by a predetermined distance.

The first pair of light source and photodetector 102, 104 is positioned with respect to the slide inserter 14 such that the downwardly projecting leg 78 of the inserter plate is interposed between the light source 102 and the photodetector 104 of the first pair when the inserter plate 68 is in its fully retracted position (i.e., away from the turntable). The second pair of light source and photodetector 108, 110 is positioned with respect to the slide inserter 14 such that the downwardly projecting leg 78 of the inserter plate is interposed between the light source and photodetector of the second pair when the inserter plate 68 is in its fully forward position.

The light sources 102, 108 of each pair provide a light beam which extend between the light source and photodetector 104, 110 of each pair. The downwardly extending leg 78 breaks the light beam of the first pair when the inserter plate 68 is fully retracted, and breaks the light beam of the second pair when the inserter plate 68 is in its fully forward position.

The first and second pairs of light sources and photodetectors are used to signal the computer of the analyzer that the inserter plate 68 of the slide inserter 14 is in the fully retracted position, indicating that the slide inserter is ready to accept a new test slide 71 for loading, or in its fully forward position, indicating that a slide has now been fully inserted into the receiving slot 52 of the rotatable turntable by the slide inserter.

Accordingly, the procedure for loading test slides into the rotatable turntable is as follows: grasp the grip 80 of the inserter plate and pull the inserter plate backwards until it is in its fully retracted position; orient a new test slide 71 so that its notch 94 is aligned with the tab 92 formed in the slide orientation plate, and place the test slide through the slide orientation plate and the cutout 84 formed in the cover plate, so that the test slide will drop into the track 70 formed in the guide plate; and push the inserter plate 68 by using the grip to its most forward position. The main body 74 of the inserter plate will slide in the track 70 of the guide plate and push the test slide into a receiving slot 52 which is aligned with the proximate end 98 of the slide inserter 14. The computer associated with the analyzer will know that the test slide 71 has been loaded into the receiving slot 52 when the downwardly projecting leg 78 of the inserter plate breaks the light beam of the second pair of light source and photodetector 108, 110.

When the inserter plate 68 is again fully retracted, the leg 78 will break the light beam of the first pair of light source and photodetector 102, 104. The associated computer will sense the disturbance in the light beam as an indication that the slide inserter is again ready for loading, and it will signal the drive mechanism associated with the turntable 50 to rotate the turntable so that the next adjacent slide receiving slot 52 formed in the turntable is positioned in alignment with the proximate end 98 of the slide inserter 14.

Although it is shown in FIGS. 5 and 7 that separate light sources 102, 108 and photodetectors 106, 110 are used to sense the position of the inserter plate 68 with respect to the rest of the slide inserter 14, it is envisioned that the light source and photodetector of each pair may be formed as a single unit on one side of the downwardly extending leg 78 and positioned on the base plate 48 in the same position as the first and second pairs of light sources and photodetectors shown in the drawings. This is a reflective type of optical sensor, such as Part No. GP2L02 manufactured by Sharp Electric Company. The light beam produced by the light source of such a sensor is reflected from the downwardly projecting leg 78 back to the photodetector integrally formed with the light source in order to indicate the position of the inserter plate 68. If such a reflective type of sensor is used, a light reflective foil or covering 114 may be placed on the downwardly extending leg 78 to enhance the reflectivity of the leg.

Figure 7B:
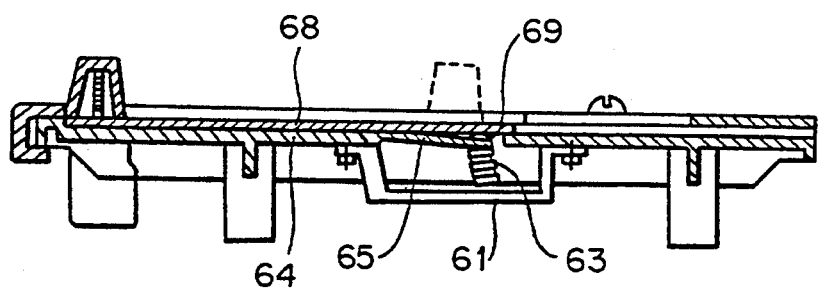
FIG. 7B is a sectional view of the slide inserter shown in FIG. 7A taken along line 7B—7B of FIG. 7A.

An alternative embodiment of the slide inserter mechanism is shown in FIGS. 7A and 7B. To prevent the inserter plate 68 from inadvertent movement due to vibration of the analyzer, the guide plate 64 may include a resilient U-shaped leaf 65 and a cutout 67 partially surrounding the leaf. The free end of the resilient leaf 65 includes a protuberance or button 69. A coil spring 63 may be positioned between the leaf and a bracket 61 suspended from and mounted to the underside of the guide plate 64. The spring 63 is compressed between the leaf 65 and the bracket 61 and thus exerts a force on the leaf. The leaf button 69 engages the underside of the inserter plate 68. This provides sufficient friction between the guide plate 64 and the inserter plate 68 to maintain the inserter plate 64 in its desired position.

THE ROTATABLE TURNTABLE AND SLIDE COVER

FIGS. 8–10 show in greater detail the rotatable turntable 50 and slide cover 54 of the chemical analyzer in their preferred form, and illustrate how a test slide is received by the rotatable turntable and held in place.

Portions of the top surface of the rotatable turntable are recessed to define a plurality of slide receiving slots 52. Each slot 52 is dimensioned to be just slightly larger than the dimensions of a test slide 71.

A leaf spring 116 is mounted on one side of each receiving slot and, in its unbiased state, has its free end 118 extending slightly into the area of the receiving slot 52 into which the test slide is inserted. Accordingly, the leaf spring 116 exerts pressure on one edge of a test slide received by the slot 52 so that the opposite edge of the test slide abuts against the opposite side wall of the receiving slot. The action of the leaf spring 116 ensures that the test slide 71 is in its proper position in the receiving slot 52.

In its preferred form, the rotatable turntable 50 is formed with twelve receiving slots 52 spaced equidistantly around its peripheral circumference, with each receiving slot 52 having an open side 118 at the periphery of the turntable. The test slides 71 are inserted into their receiving slots through the open sides 118, and are held in place by the leaf springs 11. Also, in its preferred form, the top corner of the turntable includes a bevelled edge 120 which will facilitate the slide's transfer from the inserter 14 to the turntable.

Openings 122 are formed through the thickness of the rotatable turntable 50 at the centers of the recessed portions defining the receiving slots 52. The openings 122 are provided so that light emitted by the reflectometer positioned beneath the rotatable turntable may impinge on the film portion 124 of the test slide 71 on which is deposited the dry analyte. The openings 122 are dimensioned to be slightly greater than the diameter of an opening 126 formed in the frame 128 of the test slide which exposes the analyte film.

Furthermore, a plurality of radially extending slots 130 are formed through the thickness of the turntable 50, each slot 130 being in communication with the receiving slot 52 and the opening 122 formed in each receiving slot. The radially extending slots 130 are provided for the slide ejector mechanism to push the slides out of the receiving slot 52 after the test has been completed, as will be described in greater detail.

As mentioned previously, a cover 54 is provided to minimize evaporation of the serum sample deposited on the test slides 71. As shown in FIG. 8, the cover 54 is mounted concentrically on the rotatable turntable 50 over its top surface, and generally is configured to define a plurality of radially extending fingers 132 each finger 132 being separated by its adjacent finger by an open ended slot 134 having a "V" shaped area. Each finger 132 of the cover includes an opening 136 formed through its thickness. The side walls of the cover which define the openings 136 are stepped inwardly to define a shoulder 138.

A plurality of button members 140 are mounted on the cover 54, each button member 140 being received by a corresponding opening 136. The button members 140 include peripheral lips 142 which are adapted to rest on the shoulders 138 defining the cover openings 136. The button members 140 extend slightly below the lower surface of the cover 54. Each button member further includes a tapered or sloping side wall 141 extending to an exposed circular surface 143, which surface has a diameter that is at least slightly greater than that of the test slide opening 126.

The button members 140 may be coated at least on their bottom surfaces with an essentially inert and non-absorbing material, such as teflon ™. The coating not only reduces friction during the cover opening and closing motions, but also does not absorb gases which may be produced as the result of chemical reactions on the test slides. Such gases, if trapped in the cover material, could affect the results of the subsequent tests.

A plurality of leaf springs 144 are mounted on the upper surface of the cover 54 and extend radially. Each leaf spring 144 has a free end on which a button member 140 is mounted. The leaf springs 144 exert pressure on the button members 140 to bias the button members downwardly in the cover openings 136 so that the lips 142 of the button members engage the shoulders 38 defining the cover openings.

The cover 54 is attached to a supporting collar 146, which collar 146 has a central opening to receive a spindle 148 on which the rotatable turntable 50 and the cover 54 are mounted. Extending radially from the collar 146 is a pin 149 which, as will be described in greater detail, is used in rotating the cover 54 clockwise and counter-clockwise in order to cover and uncover the film portion 124 of each test slide 71 mounted on the rotatable turntable.

The cover is maintained in alignment with the rotatable turntable 50 by a pair of spring loaded ball bearings 151 positioned diametrically opposite one another on the collar 146 of the cover, each ball bearing 151 being partially received by one of two detents of two pairs of adjacent detents 153 formed in the hub 362 retaining the turntable to the spindle 148. The detents 153 are particularly positioned so that, when the ball bearings 151 of each pair engage one detent of each pair of detents, the cover 54 will be in the closed position, that is, covering the receiving slot 52 and in particular the film portion 124 of a test slide located in the receiving slot, and when the ball bearings 151 of each pair are received in the other detent 153 of each pair of detents, the cover will be in the open position, that is, where the receiving slot 52 and in particular the film portion of a test slide located in the receiving slot is uncovered.

An alternative form of the cover-to-turntable alignment mechanism is shown in the exploded view of FIG. 8A.

A hub member 362a is mounted to the vertical spindle 148a by a set screw 101. The hub member 362a includes three recesses 103 formed in its circumferential surface. An inner spring clip 105 having three upwardly extending resilient leafs 107 is mounted on the top surface of the rotatable turntable 50a at its center. The three leafs 107 fit into the three recesses 103 of the hub when compressed. Each leaf 107 includes an outward dimple or protrusion 109.

A collar member 146a includes an axial bore 111 into which the hub 362a fits. The inner sidewalls of the collar defining the bore 111 include grooves (not shown), which are engaged by the protrusions 109 on the spring clip, due to the expansion of the clip inside the collar. The inner spring clip 105 takes up any play between the collar and hub and ensures proper vertical positioning of collar 146a on the spindle 148a.

The collar 146a has an arm 113 extending radially outwardly. The arm includes a pin 115 mounted on it and extending downwardly. The pin 115 engages an alignment hole 117 formed in the cover 54a, and the collar is fixedly mounted on the cover so that the collar 146a and the cover 54a rotate together.

Interposed between the collar 146a and the cover 54a is a preferably one piece, circular leaf spring 119. The leaf spring 119 includes three radially extending resilient arms 121. Positioned beneath each arm 121 is a ball bearing 123. The ball bearings 123 are at least partially received by holes 125 formed through the thickness of the cover 54a.

Three pairs of detents or recesses 127 are formed in the top surface of the turntable 50a. The detents of each pair are separated from each other a predetermined distance (sufficient to allow the cover 54a to cover and uncover the receiving slots 52), and each pair is situated arcuately on the turntable and in alignment with a respective ball bearing-receiving hole 125. The force exerted on the ball bearings 123 by the arms 121 of the leaf spring causes the ball bearings 123 to engage one detent 127 of each pair. The position of the cover 54a relative to the turntable 50a is thus maintained until a sufficient force is exerted on the cover to cause the ball bearings to move into the other detent of each pair of detents. Accordingly, the cover may be maintained in either an open or a closed position.

FIGS. 9, 9A and 9B illustrate the sequence of loading a test slide 71 onto the rotatable turntable 50. In FIG. 9A, the slide inserter 14 is illustrated as pushing a test slide 71 into a receiving slot 52 of the turntable and between the turntable 50 and the cover 54. As stated previously, the slide inserter 14 is positioned above the base plate 48 of the analyzer at the same level as the rotatable turntable 50 so that the test slide resides in the same plane in which the receiving slots 52 the turntable are formed. This, of course, facilitates insertion of the test slides into the receiving slots.

FIG. 9B illustrates the test slide 71 being partially received by the receiving slot 52 of the rotatable turntable. The edge 150 of the test slide 71 engages the sloped side wall 141 of the button member 140, which is biased downwardly to extend below the lower surface of the cover, and the test slide will push the button member upwardly in its respective cover opening 136.

FIG. 9 illustrates the test slide 71 being fully received by the slot of the rotatable turntable 50. The button member 140 is deflected by the test slide 71 and due to the action of the leaf spring 144, exerts a pressure on the test slide and, as shown in FIG. 9, fully covers one side of the exposed analyte film 124 of the test slide, which side of the film will receive a predetermined amount of blood serum to be analyzed.

FIG. 11 illustrates the bridge bracket 58 shown in FIG. 3 in a raised position. As previously mentioned, the bridge bracket 58 is mounted over the cover 54 and rotatable turntable 50 and is supported at its ends by two upright supports 56. The bridge bracket 58 basically includes an elongated plate which is bent C-shape in cross-section and which is used to support a number of components of the chemical analyzer. The bridge bracket 58 is pivotally mounted on one of the supports 56 so that it may be raised to an upright position, as shown in solid lines in FIG. 11, or lowered to a second position bridging the rotatable turntable 50 and cover 54, as shown in phantom in FIG. 11.

A central opening 152 is formed in the bridge bracket 58 so that the bracket does not interfere with the spindle 148 on which the cover and rotatable turntable are mounted. The bridge bracket 58 may be conveniently raised to facilitate cleaning the cover and rotatable turntable of the analyzer and for easily accessing these components for any maintenance or repairs. It should be noted in FIG. 11 that a knurled knob 154 is screw-threaded onto the spindle 148 over the collar 146 of the cover. This knob 154 may be removed quite easily so that the cover 54 may be easily lifted from the spindle on which it is mounted.

Several additional components of the chemical analyzer of the present invention are shown in FIG. 11. On the underside of the bridge bracket 58 is mounted a printed circuit board 156. The printed circuit board 156 is coupled to the rest of the circuitry of the analyzer through a connector 157. An optical code reader 158 is mounted on the printed circuit board 156. When the bridge bracket 58 is in the lowered position, the optical code reader 158 is positioned directly above the test slides 71 mounted in the receiving slots 52 of the rotatable turntable.

The optical code reader 158 senses the bar codes 86 on the top side of the test slides, and provides this information to the computer which interprets the bar code information and determines what tests are to be performed.

To enable the optical code reader 158 to read the bar codes, the cover 54 is rotated with respect to the turntable 50 so as to uncover a major portion of the test slides. In other words the test slides 71, and in particular the bar codes 86 on the test slides, are exposed between the open "V" shaped area of the slots 134 formed in the cover. During the initial operation of the analyzer, and after the test slides have been loaded onto the turntable 50, the turntable is rotated such that each test slide 71 passes one by one under the optical code reader 158.

As mentioned previously, the cover 54 is adapted to rotate clockwise and counter-clockwise with respect to the turntable 50 in order to cover and uncover the test slides mounted on the turntable. Only a small arcuate rotation is needed to uncover the slides 71; for example, if the turntable 50 is configurated with 12 receiving slots 52, the cover 54 need only rotate 15 degrees in either direction in order to cover and uncover the test slides.

Referring for the moment to FIG. 3 of the drawings, it is seen that a reversible DC drive motor 60 is mounted on the top surface of the bridge bracket 58. The shaft of the drive motor 60 is connected to an L-drive reduction gear box 160, which gear box 160 includes a vertical shaft 162 extending through the bridge bracket 58.

Again referring to FIG. 11 of the drawings, an elongated pivot block 164 is mounted on the vertical shaft 162 of the gear box near one of its ends. A pin 166 protrudes from the underside of the pivot block 164.

When the bridge bracket 58 is in its lowered position the pin 168 extends far enough below the pivot block 166 to engage the radially extending pin 149 of the cover collar 146.

In order to uncover the test slides, the turntable 50 (and cover 54) are rotated with the spindle 148 by the turntable drive motor until the cover pin 149 extends substantially beneath the pin block 164. The drive motor 60 is then energized to rotate in one direction such that the pin 166 on the pivot block 164 engages the cover pin 149, causing the cover to rotate with respect to the turntable. During this action, the turntable 50 is maintained in its present position so that it does not rotate with the cover 54. The pivot block 164 will sweep through a full 360 degree rotation, but the cover 54 need only rotate about 15 degrees due to the action of the pivot block 164 and pin 166 in order to uncover the test slides.

To cover the slides, the DC motor 60 is energized with a voltage of opposite polarity so that the pivot block 164 now rotates in the opposite direction. The pin 166 will again engage the cover pin 149 so that the cover will rotate with respect to the turntable about 15 degrees in the opposite direction to cover the test slides.

An optical sensor 168, which may be the reflective type, is mounted on the printed circuit board 156 directly below the end of the pivot block 164 which is opposite to the end at which the block is mounted to the gear box shaft 162. A reflective foil or tape 170 surrounds the end of the pivot block 164.

When the cover has to be rotated, the associated electronics and computer of the analyzer causes the DC motor to be energized. The pivot block 164 will rotate in one direction until the reflective foil 170 is positioned over the optical sensor 168, which will be a full 360 degree rotation. The sensor 168 will detect the presence of the end of the pivot block 164 and signal the computer of the analyzer which will then de-energize the drive motor 60. Thus, the optical sensor will always sense when a full rotation of the pivot block 164 has occurred, either clockwise or counter-clockwise, which will indirectly indicate that the operation of covering or uncovering the test slides has been completed.

In an alternative embodiment of the cover opening mechanism, as shown in FIGS. 22A and 22B, the drive shaft of the L-drive gear box 160 has a pinion gear 161 mounted on it. The pinion gear 161 engages a secondary gear 163 with peripheral teeth, which gear 163 is rotatably mounted on a vertically extending pin 165 mounted on the underside of the bridge bracket 58a.

The secondary gear 163 has mounted on its underside a cover actuating pin 167, which is offset from the center of the gear. Pin 167 engages the cover pin 149 to open and close the cover in much the same way as pin 166 does in the previous embodiment.

The gear 163 further has a radially extending arm 169 mounted on it. Arm 169 cooperates with optical sensor 168 in much the same way as pivot block 164 does in the previous embodiment so that the analyzer can sense when the secondary gear 163 has made a complete revolution and has returned to its "home" position.

THE METERING ASSEMBLY OF THE ANALYZER

One of the advantages of the present invention is that only a small amount, on the order of 10 microliters, of serum to be analyzed need be deposited on each test slide. Accordingly, the metering apparatus of the chemical analyzer need only carry approximately 120 microliters of serum if all 12 test slides are to be utilized FIGS. 11-17 illustrate the components of the chemical analyzer which perform the metering operation.

As discussed previously, the metering apparatus of the chemical analyzer includes a pipette assembly 16 (see FIG. 16), which assembly basically includes a pipette 18 and a tube 20 connected to the pipette 18 and to the chemical analyzer. The tube 20 carries an electrical, two wire conductor conduit 172, as well as an air conduit 174.

The pipette 18 has a tapered stainless steel end on which is fitted a removable and disposable tip 176. The tip 176 has an upper end which is formed with a series of radially extending supporting fins 178.

After the pipette 18 has aspirated a predetermined volume of serum to be analyzed, as will be explained in greater detail it is placed through the opening 23 in the analyzer cover 12 (see FIG. 1), and its disposable tip 176 extends through the bore of a pipette support ring 180 (see FIG. 3) situated on the bridge bracket 58, with the supporting fins 178 of the tip resting on the upper surface of the support ring 180. As shown in FIG. 12, the tip 176 of the pipette extends below the bridge bracket 58 and directly above the film portion 124 of a test slide 71 mounted on the turntable, which is rotated so that the slide is in alignment with the pipette.

A vertically upward and downward movement is provided to the pipette 18 to ensure that a drop formed on the pipette tip will be properly transferred to the analyte film portion of the slide by capillary action.

Figure 12A:
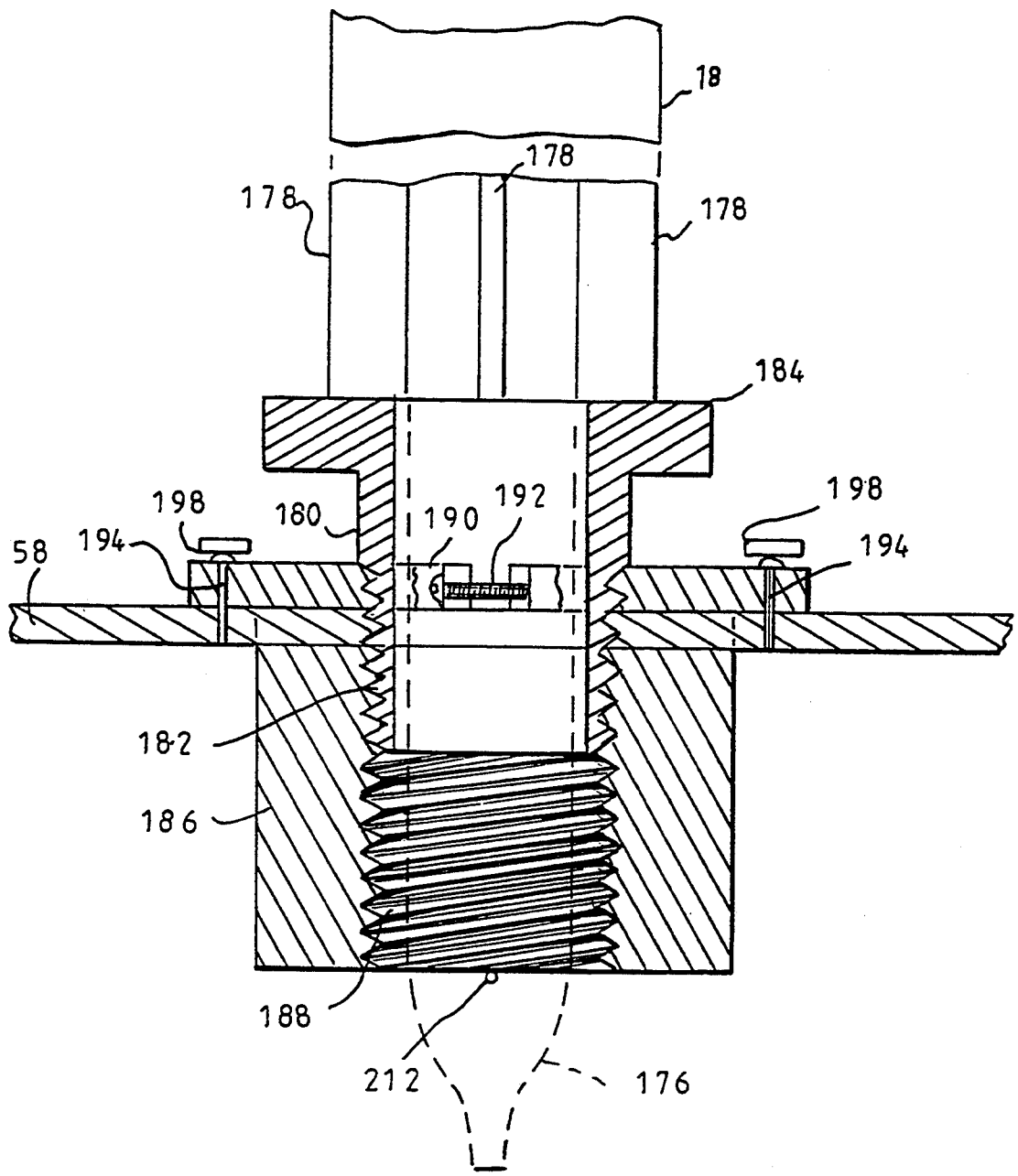
FIG. 12A is a detailed longitudinal cross-sectional view of a portion of the assembly shown in FIG. 12.

As more specifically shown in FIG. 12A, the supporting fins 178 of the pipette rest on the top surface of the support ring 180. The support ring 180 has a threaded cylindrical body 182 and an upper flange 184 extending from the cylindrical body 182, the supporting fins 178 of the disposable tip resting on the upper flange 184.

A cylindrical collar 186 which is internally threaded includes a bore 188 which receives the threaded cylindrical body 182 of the support ring. The support ring 180 may thus be threaded into the collar 186 a predetermined distance which, as will be seen, is used to adjust of the height of the pipette tip 176 in relation to the test slides mounted on the rotatable turntable. The outer collar 186 further includes a split flange 190 at its upper portion, where the flange ends are adjustably screwed together so that the outer collar 186 may be tightened about the inner support ring 180.

After the height of the pipette tip has been adjusted by threading the support ring 180 into the outer collar 186 a predetermined distance, the split flange 190 of the outer collar is tightened by adjusting the screw 192 so that the support ring will not turn within the outer collar and so that the height of the pipette will always be maintained at its proper setting.

A pair of guide pins 194 are mounted through the upper flange 190 of the outer collar and extend downwardly in the same direction as the outer collar 186. The guide pins 194, as well as the outer collar 186, pass through correspondingly dimensioned holes formed in the bridge bracket 58. The guide pins 190 prevent the support ring 180 and outer collar 186 from turning on the bridge bracket 58.

As shown in FIG. 3, a leaf spring 196 is mounted on the top surface of the bridge bracket 58. The free end of the leaf spring is split to define forked ends 198. The forked ends 198 engage the upper flange of the outer collar 186 at the heads of the guide pins 198, such that the leaf spring biases the outer collar 186 downwardly through the bridge bracket 58.

As shown in FIG. 3, and as mentioned previously, a drive motor 62 is provided to cause the pipette 18 to move vertically to deposit a serum sample on the test slides. The shaft of the drive motor 62 is coupled to an L-drive reduction gear box 200 also mounted on the upper surface of the bridge bracket 58. The vertically extending shaft of the gear box is coupled to a cam wheel 202, as shown in FIG. 12. The cam wheel 202 has a lower surface 204 which is sloped from a horizontal plane, which effectively provides the cam wheel with a non-uniform thickness.

A cam follower 206, in the form of a clevis, that is, with two ends 208 which partially surround the outer collar, 186 is pivotally mounted between a pair of extension blocks 210 from the underside of the bridge bracket. Each of the two split ends 208 includes a pin 212 which extends partially inwardly towards each other. The bottom of the outer collar 186 rests on the two pins 212. The opposite end of the cam follower 206 includes an outwardly extending pin 214 on which is rotatably mounted a cam follower wheel 216.

The leaf spring 196 biases the outer collar 186 downwardly such that it exerts a force on the pins 212 of the split ends of the cam follower 206 which, in turn, causes the cam follower wheel 216 to ride along the periphery of the sloping lower surface 204 of the cam wheel 202.

To effect a downward movement of the pipette 18 resting in the support ring 180, the drive motor 62 is energized, which causes the cam wheel 202 to rotate. Because the cam follower wheel 216 engages the lower surface of the cam wheel 202 which lower surface is sloping, the cam follower 206 will pivot downwardly, as shown in the dashed lines in FIG. 12, to its lowest position as the cam wheel 202 rotates to a point where the cam follower wheel 216 rests on the cam wheel at its narrowest portion.

The cam wheel 202 then continues to rotate until it returns to its initial position shown in FIG. 12, that is, where the thickest portion of the cam wheel 202 resides over the cam follower wheel 216. This causes the cam follower 206 to pivot on the extension blocks 210, forcing the outer collar 186 and pipette 18 upwardly against the force of the leaf spring 196.

An optical sensor 218, in the form of a pair of a light source and a photodetector spaced apart slightly from each other, is mounted on the underside of the bridge bracket 58. One of the split ends 208 of the cam follower 206 is extended such that when the pipette 18 is in its most raised position, the end 208 will be interposed between the light source and photodetector of the sensor 218 and disturb a light beam between the two.

At the appropriate time, the associated computer and electronic circuitry of the chemical analyzer will energize the drive motor 62, causing the cam wheel 202 to rotate. The cam follower 206 will pivot downwardly, following the slope of the lower surface of the cam wheel, and the extended split end 208 of the cam follower will be pivoted away from the optical sensor 218. When the cam wheel has rotated a full 360 degrees such that the cam follower 206 and pipette 18 have returned to their initial positions, the extended split end 208 of the cam follower will again disturb the light beam between the light source and photodetector. This disturbance in the light beam is detected, thus indicating that a full reciprocatingly vertical motion of the pipette 18 has been completed. The drive motor 62 will then be de-energized by the electronic circuitry until the next test slide has been properly positioned below the tip 176 of the pipette, where upon the sequence described above is repeated.

As will be explained in greater detail a drop of serum 220 to be analyzed is formed on the pipette tip 176 and is suspended from the tip prior to a downward motion of the pipette. After this metering of a predetermined amount of serum has taken place, the drive motor 62 is then energized to lower the pipette 18 to the test slide. Because the full drop of serum is formed on the pipette tip 176 prior to lowering the pipette to the test slide, it is not necessary to lower the pipette until its tip almost touches the film portion 124 of the test slide.

The metering operation relies on capillary action to draw the drop which has formed on the pipette tip from the pipette and onto the slide. The halfway height of a 10 microliter drop which is formed on the pipette tip has been measured to be approximately 1.2 millimeters. Accordingly, the chemical analyzer is adjusted so that the pipette tip 176 extends this distance above the film portion 124 of the test slide. However, this distance may vary in either direction by as much as 1 millimeter, as the drop will still be drawn by capillary action onto the test slide. Accordingly, stringent tolerances are not required in the present invention for proper metering to occur, as is required in many conventional chemical analyzers, so that the height tolerances in the rotatable turntable and bridge 58 may be relaxed.

FIGS. 13E and 13F show a modification to the pipette lifting mechanism. Before the pipette 18 is place into its support ring 180 in the chemical analyzer, it is placed partially into a vial of serum so that a predetermined amount of serum may be aspirated into the disposable tip. The pipette is then placed in its support ring 180 and the user may then press a key on the keyboard 4 to indicate that serum has been drawn into the tip and that the serum is ready to be tested.

One of the problems which may occur is that there may be a time delay between when the serum is drawn into the pipette 18 and when the user signals the analyzer to begin the operation of depositing the serum onto each test slide and testing the serum. During that time delay, the temperature of the pipette may increase. This increase in temperature may cause air above the serum in the pipette tip 176 to expand. This expansion may, in turn, force some serum out of the disposable tip prior to the metering operation so that an incorrect amount of serum may possibly be deposited on the test slides.

To minimize the possibility of a time delay between the steps of drawing the serum into the pipette tip and the metering operation, so as to minimize any temperature change which the pipette experiences, the support ring 180 may include an electrical switch to automatically sense when the pipette 18 has been properly placed in the support ring.

As shown in FIG. 13F, the switch, in one form, may include a first conductive contact 222 disposed on the top surface of the support ring 180, and a second conductive contact 224 disposed on the side wall of the support ring. When the supporting fins 178 of the disposable tip rest on the top surface of the support ring 180, as shown in FIG. 13E, the two electrical contacts will engage and provide an electrical path through the switch. This electrical path is sensed and provided to the associated computer and electronic circuitry of the analyzer which will then immediately begin the metering and testing operation. This will avoid any time delay by the user failing to immediately press the proper keyboard button after serum has been drawn into the pipette tip 176 and the pipette tip has been properly placed on the support ring 180.

Alternatively, and as shown in FIG. 22A, an opto-sensor 175 may be mounted on the bridge assembly. When the pipette is replaced in the pipette lifting mechanism, the tip 176 of the pipette will break a light beam of the opto-sensor 175, signalling the analyzer and its associated computer to proceed with the sample depositing operation.

An alternative form of the pipette lifter mechanism of the metering assembly is illustrated by FIGS. 22-26.

A motor 226 is mounted to a reducing L-drive gear box 228, both of which are mounted on the top side of the bridge bracket 58 (or to a supporting plate 227 mounted on bracket 58). The vertically extending output shaft of the gear box 228 has a gear 230 with peripheral teeth mounted on it. The gear box gear 230 engages an intermediary gear 232 mounted rotatably on a post 234 extending downwardly from the bridge bracket 58 (or plate 227). The intermediary gear 232 includes an eccentric boss or hub 236 which acts as a cam.

A rocker arm 238 is mounted to the bridge bracket to pivot vertically. The rocker arm 238 includes two outwardly disposed lever arms 240, 242. One lever arm 240 engages the eccentric boss 236 of the intermediary gear 232. The other lever arm 242 is split into two forked ends 244, clevis-style. Two pins 246 extend partially inwardly from each forked end 244 of the second lever arm.

The pipette 18 is mounted on the bridge bracket 58 in a manner which is similar to that previously described. A guide or stabilizing collar 248 is mounted on a second bracket 250 above the bridge bracket 58 and includes an internal bore which is dimensioned to be slightly larger than a stainless steel tip portion 252 of the pipette. A second collar 254 is mounted on the underside of the bridge bracket 58 (or plate 227), and includes a central bore which is concentric with an opening formed through the thickness of the bridge bracket (or plate 227).

A pipette support ring 256 includes a lower cylindrical body 258 which is slidably received by the central bore of the second collar 254 so that the support ring 256 may reciprocatingly slide within the second collar. The support ring further includes an upper flange 260 which extends outwardly radially from the cylindrical body 258 and which rests on the inwardly disposed pins 246 of the spaced apart forked arms 244 of the rocker arm's second leg. Alternatively, pins 246 may be eliminated and flange 260 may rest directly on the forked ends 244. A compression spring 262 is mounted between the underside of the guide collar 248 and the support ring 256. The spring forces the support ring 256 downwardly into the second collar 254.

The distance from the pipette tip 176 to the test slide 71 is adjusted by adding wishbone-shaped shim washers 264 between the slidable support ring 256 and the stationary second collar 254. This distance is determined when the chemical analyzer is calibrated.

The alternative embodiment of the pipette lifter described above operates in the manner described below. The motor 216 is energized causing the gear 230 mounted on the gear box to rotate. This, in turn, causes the intermediary gear 232 to rotate on its mounting post 234. The eccentric boss 236 of the intermediary gear engages the first lever arm 240 of the rocker arm and moves with the eccentricity of the intermediary gear 232. The movement of the rocker arm 238, which pivots in a vertical plane, causes the lifter leg 242 to raise and lower the support ring 256 within the second collar 254 against the force of the compression spring 262.

A pipette 18, which is situated in the stabilizer collar 248, and with its supporting fins 178 of the disposable tip resting on the support ring 256, will follow the reciprocating movement of the support ring so that the tip 176 of the pipette will be raised and lowered with respect to a test slide situated beneath it.

The pipette lifter mechanism is initially set by the chemical analyzer to be in its "home" position. That is, the support ring 256 is raised to its highest position with respect to the second collar 254. To sense when this has occurred, an optical sensor 266 in the form of a spaced apart LED light source and a detector is positioned near the support ring 256. A portion 268 of the upper flange 260 of the support ring is extended radially so that when the support ring is in its most upward position, the extended portion 268 of its flange is interposed between the LED light source and the detector of the sensor 266 to interfere with the light beam between the two. The optical sensor 266 is connected to the associated computer and electronic circuitry of the chemical analyzer so that the analyzer knows that the pipette mounted in the support ring is in its fully raised, "home" position.

As with the previous embodiment, the motor 226 is energized to cause the pipette 18 to lower a predetermined distance to a test slide situated beneath it and after a drop of serum has been deposited on the test slide, to return to its raised "home" position. This reciprocating action is due to the eccentricity of the boss 236 of the intermediary gear 232 which gear will rotate a full 360 degrees. When the extended portion 268 of the upper flange of the support ring 256 rises to a position where it again interrupts the light beam between the LED source and the detector, the associated circuitry recognizes that the pipette 18 has returned to its initial position, and it will de-energize the motor 226.

Figure 14:
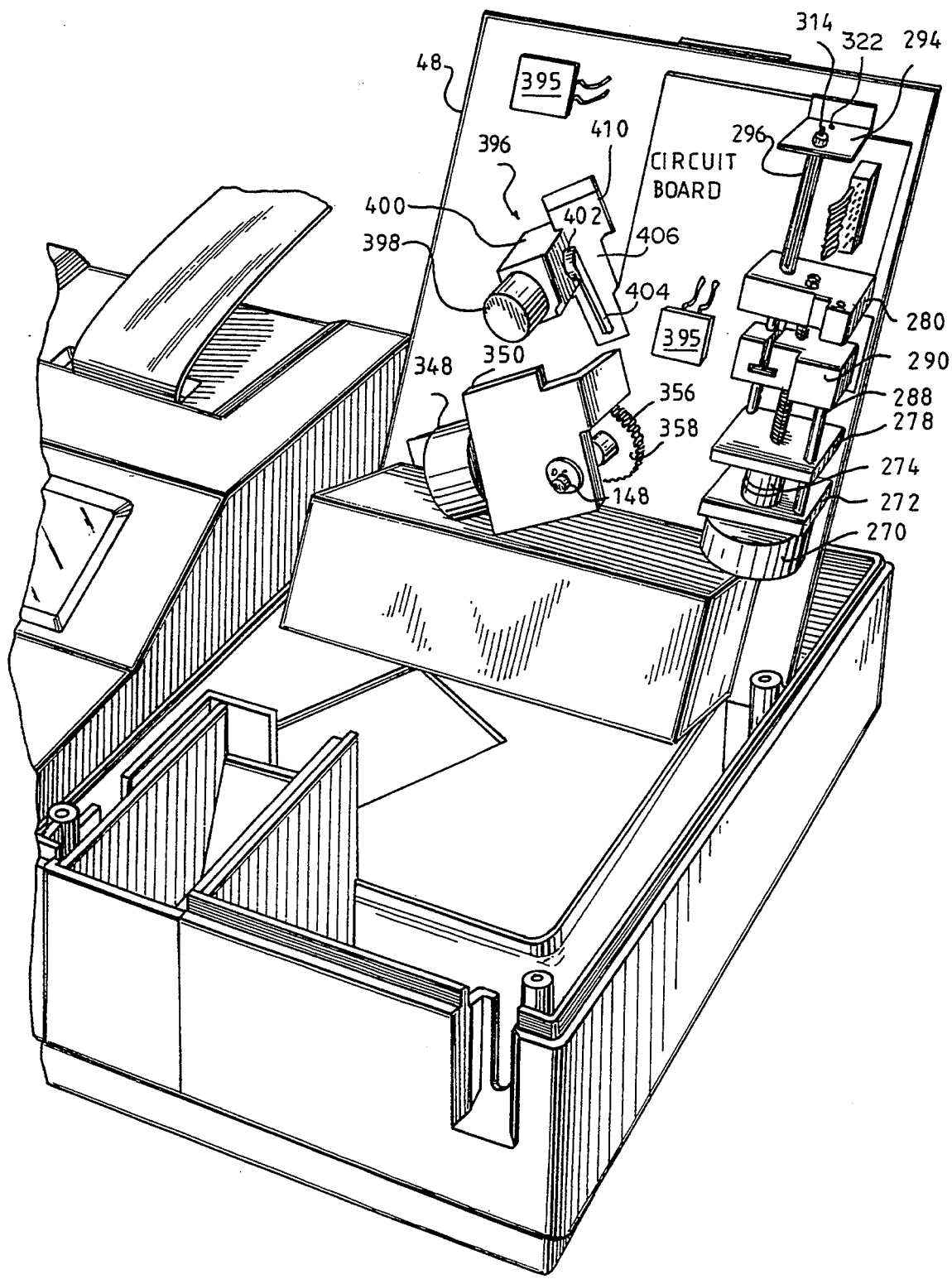
FIG. 14 is a perspective view of the chemical analyzer shown in FIG. 1 and illustrating the drive assemblies for the turntable and metering device.

FIGS. 14 and 15 show one form of the metering assembly of the present invention which is used to draw a predetermined amount of serum into the pipette tip and to deposit serum on each test slide. The metering assembly is preferably mounted on the underside of the base plate 48, which is shown in a raised position in FIG. 14.

The metering assembly includes a reversible DC stepper drive motor 270 which is mounted on a support member 272 attached to the underside of the base plate 48. The shaft of the drive motor 270 is connected to a coupler 274 which acts as a universal joint.

A lead screw 276 is mounted between a second support member 278 and a third support member 280 which are attached to the underside of the base plate. One end 282 of the lead screw is connected to the other side of the coupler 274 opposite the side to which the drive motor shaft is connected and the other end 284 of the lead screw 276 passes through the third support member 280 and is mounted to the member 280 by appropriate hardware, such as a pair of nuts 286. The lead screw 276 is rotatable relative to the second and third support members. The metering assembly further includes a pair of guide rods 288 which extend at least between the second and third support members.

Mounted on the lead screw 276 between the second and third support members 278, 280 is a movable lead screw engaging member block 290. When the stepping motor 270 is energized, the lead screw 276 will rotate and the block 290 will move reciprocatingly up and down on lead screw between the second and third support members 278,280. The guide rods 288 also pass through the movable block 290 and prevent the movable block from twisting or rotating on the lead screw 276 as the lead screw turns.

The movable block 290 has a T-slot 292 formed in one of its surfaces. Mounted between the third support member 280 and a support bracket 294 affixed to the underside of the base plate is a syringe 296 in the form of a tubular member. More specifically, one end of the syringe 296 is placed into a U-slot formed in the third support member 280 and held in place by a cover clip 298 and the other end is secured to bracket 294.

The syringe 296 is an air-tight member which includes a plunger 300 which extends through its central bore. The plunger 300 extends out of one end of the syringe and has an enlarged head 302 which is fitted into the T-slot 292 formed in the movable block 290. A teflon TM piston 304 is mounted on the other end of the plunger 300. The piston 304 and plunger 300 are slidable within the central bore of the syringe. A syringe which is suitable for use in the chemical analyzer of the present invention is Part No. 1725 manufactured by Hamilton Co., and described in U.S. Pat. No. 3,150,801.

When the stepping motor 270 is energized with a voltage of predetermined polarity and phasing, it will turn the lead screw 276, causing the movable block 290 to advance in a direction from the second support member 278 to the third support member block 280. This, in turn, will drive the plunger 300 and piston 304 through the central bore of the syringe, causing a serum sample collected by the pipette 18 to be expelled from the pipette tip 178.

When the stepping motor 270 is energized with a voltage of opposite phasing, the lead screw 276 will rotate in an opposite direction, causing the movable block 290 to move backward on the lead screw in a direction from the third support member 280 to the second support member 278. This, in turn, will cause the plunger 300 and piston 304 to be drawn back through the syringe, causing serum to be aspirated into the pipette tip 178.

A "home" position is selected for the movable block 290 on the lead screw 276. This position is generally where the movable block is near the third support member 280. A reflective type of optical sensor 306, such as described previously, is positioned adjacent a side wall of the movable block 290 when the block is in its home position. The side wall of the block may further have mounted on it a reflective foil 306 or other material in order to optimize the effect of the optical sensor. The associated computer and electronic circuitry of the chemical analyzer will be signalled by the optical sensor 308 when the movable block 290 is in its home position, or will place the movable block in its home position, by energizing motor 270, causing the lead screw 276 to rotate until the block's home position is determined by the optical sensor, which then signals the associated electronic circuitry.

The pipette assembly 16 is shown in FIG. 16. As mentioned previously, the pipette assembly includes a pipette 18 having a stainless steel tip portion on which is fitted a disposable tip 176. The tip converges to form a narrow end 310 on which a drop of sample serum is formed. The opposite end of the disposable tip includes a plurality of radially extending supporting fins 178. This opposite end is fitted onto the stainless steel tip of the pipette.

The pipette assembly further includes an outer tube 20. The outer tube 20 carries an air conduit 174 and a two wire conductor electrical conduit 172. The air conduit 174 is connected at one end through the body of the pipette 18 to a central bore (not shown) formed in the body, which bore (not shown) extends to an opening formed in the stainless steel tip so that the air conduit 174 is in communication with the interior of the disposable pipette tip 176 when the disposable tip is fitted onto the stainless steel tip of the pipette 18.

The other end of the air conduit 174 includes an airtight female connector 312 which is adapted to be inserted onto a male connector 314 mounted on the support bracket 294, which male connector is in communication with the syringe 296.

The electrical conduit 172 is connected through the pipette body to a single pole single throw (SPST) push button switch 316 mounted on an enlarged head portion 318 at the top of the pipette 18. The other end of the electrical conduit 172 is connected to a male plug connector 320 which is adapted to be received by a female connector 322 also mounted on the support bracket 294

(see FIGS. 1 and 14). The mating female connector 322 is connected to the electronic circuitry of the chemical analyzer.

At the appropriate time during operation of the chemical analyzer, the display 8 will instruct the user to insert the pipette tip 176 into a vial containing the sample serum to be analyzed. When this step has been done, the user will signal the chemical analyzer by pressing the push button switch 316 on pipette head 318 that the pipette is ready to aspirate sample serum into the tip. The chemical analyzer will then cause the stepping drive motor 270 to turn the lead screw 276 a certain number of revolutions, causing the plunger 300 to be withdrawn through the syringe a predetermined distance. The vacuum created in the disposable tip 176 will cause serum to be drawn from the sample vial into the disposable tip.

Only 10 microliters of serum is drawn into the tip for each test slide to be analyzed. Accordingly, if all twelve test slides are to be analyzed, 120 microliters of serum is drawn into the tip. An additional about 30 to about 40 microliters is preferably also drawn into the tip for proper operation.

The chemical analyzer will then signal the user to withdraw the pipette 18 from the serum vial. After this has been done an additional 2 microliters of air is drawn into the tip 176. The purpose of drawing air into the tip 176 after the desired quantity of serum has been aspirated is so that the tip 176 may be wiped clean without drawing any serum from the tip due to capillary action caused by the wiping material touching the open end 310 of the disposable tip.

The pipette 18 is then placed in the support ring 180 through the hole 23 in the cover 12 and the user presses a key on the key pad 4 to instruct the analyzer to begin the metering operation.

The associated computer and electronic circuitry of the chemical analyzer will then energize the motor 270 so that the lead screw 276 rotates in the opposite direction from the direction which caused the sample to be aspirated, causing the plunger 300 to move through the syringe toward the support bracket 294. This will force serum out of the pipette tip 176.

Because a stepping motor 270 is used, the number of turns of the lead screw 276 may be maintained to a desired number with accuracy and, consequently, the amount of fluid discharged by the pipette 18 is accurately maintained. Accordingly, the stepping motor 270 will turn a predetermined number of revolutions to cause the syringe 296 to force the preferred 10 microliters of serum out of the pipette tip 176 for each test slide. For the first test slide to be deposited with serum, the lead screw 276 is rotated an additional amount so that the 2 microliters of air which was drawn into the tip prior to wiping the tip and 10 microliters of serum are forced out of the tip.

When the 10 microliters are forced out of the pipette tip, a drop will form and be suspended below the open end 310 of the tip. The pipette lifter assembly is then activated, which will cause the pipette tip 176 to be lowered until the drop touches the film portion 124 of the test slide, where upon, by capillary action, the sample serum will flow onto the analyte film portion of the test slide. The pipette lifter will then raise the pipette tip 176 to its normal position, and signal the associated computer and electronic circuitry of the chemical analyzer to advance the turn table 50 so that the next adjacent test slide is positioned underneath and in alignment with the pipette tip 176. The stepping motor 270 of the metering assembly is then again energized to expel an additional 10 microliters of serum out of the pipette tip to form a second drop. The pipette lifter mechanism is then again energized to deposit the drop on the next test slide. The sequence is repeated until a sample has been provided to each test slide.

It is to be noted that the metering assembly operates by first aspirating serum by having the lead screw 276 turn in one direction and then expelling serum that it had previously aspirated by having the lead screw 276 turn in the opposite direction. This bi-directional rotation of the lead screw 276 may result in backlash between the lead screw 276 and the movable block 290, which may result in inaccuracy in the metering operation. In other words, the same number of revolutions of the lead screw in each direction may cause the movable block 290 (and, consequently, the plunger 300) to move different distances longitudinally along the lead screw 276.

One solution to this problem is to construct a lead screw/movable block assembly with little or no backlash, by fine machining techniques. However, such can be a rather expensive solution to the problem.

A more preferred and less expensive solution is to program the associated computer of the chemical analyzer with the number of turns of the lead screw which are necessary to eliminate the backlash, i.e., the difference between the number of rotational turns of the lead screw in opposite directions which will produce the same linear movement of the block 290. This number can be determined during calibration of the chemical analyzer. Thereafter, the chemical analyzer will add a certain number of rotations to the number of turns normally required to move the block 290 a predetermined distance along the lead screw, whenever the direction of the rotation of the lead screw is reversed.

Figure 27:
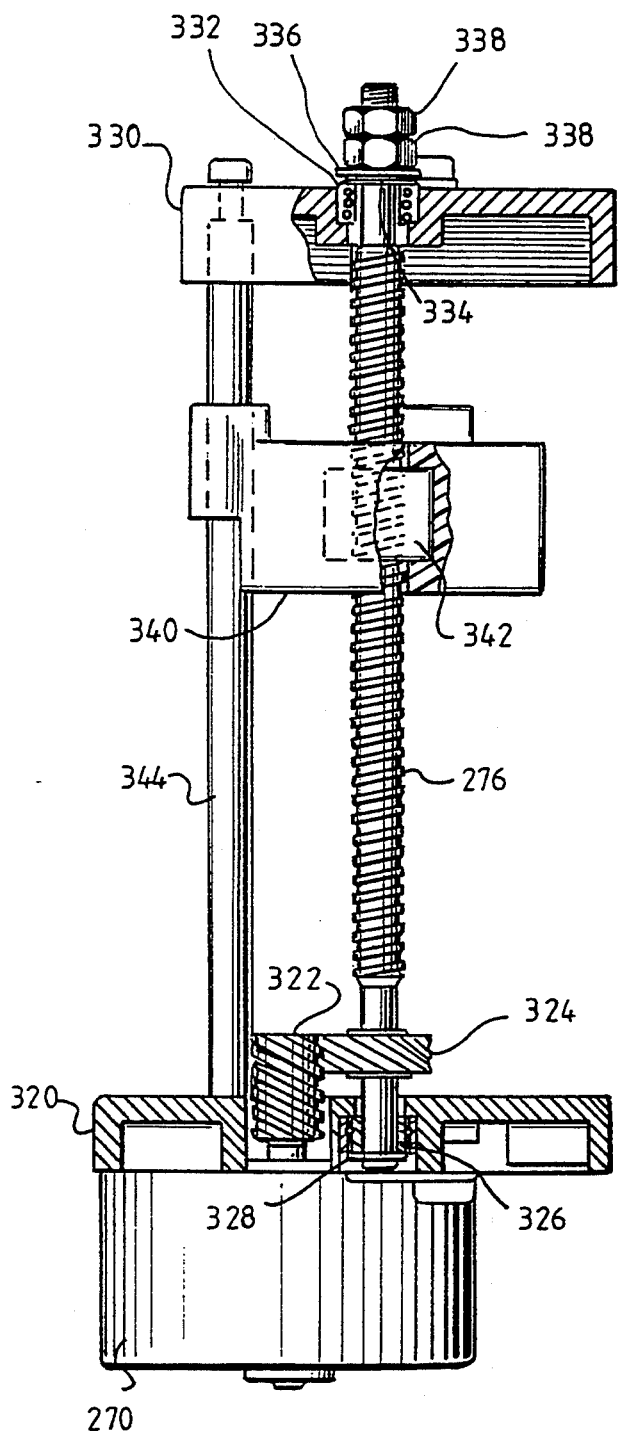
FIG. 27 is a bottom view, partially in section, of another alternative embodiment of the metering device of the present invention.
Figure 28:
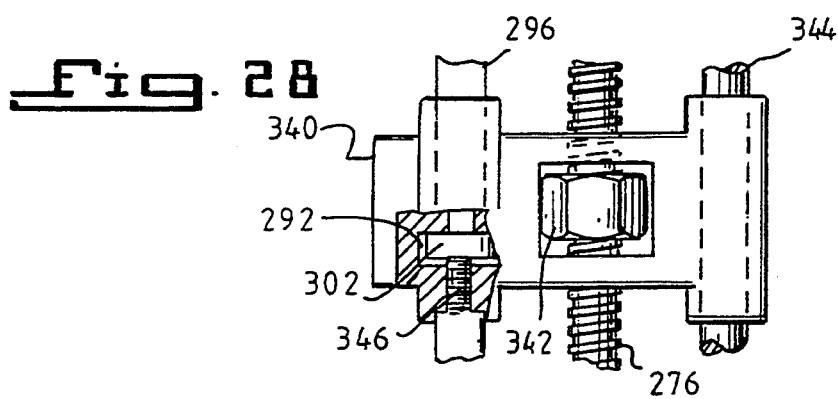
FIG. 28 is a detailed partial sectional view of a portion of the metering device shown in FIG. 27.
Figure 27A:
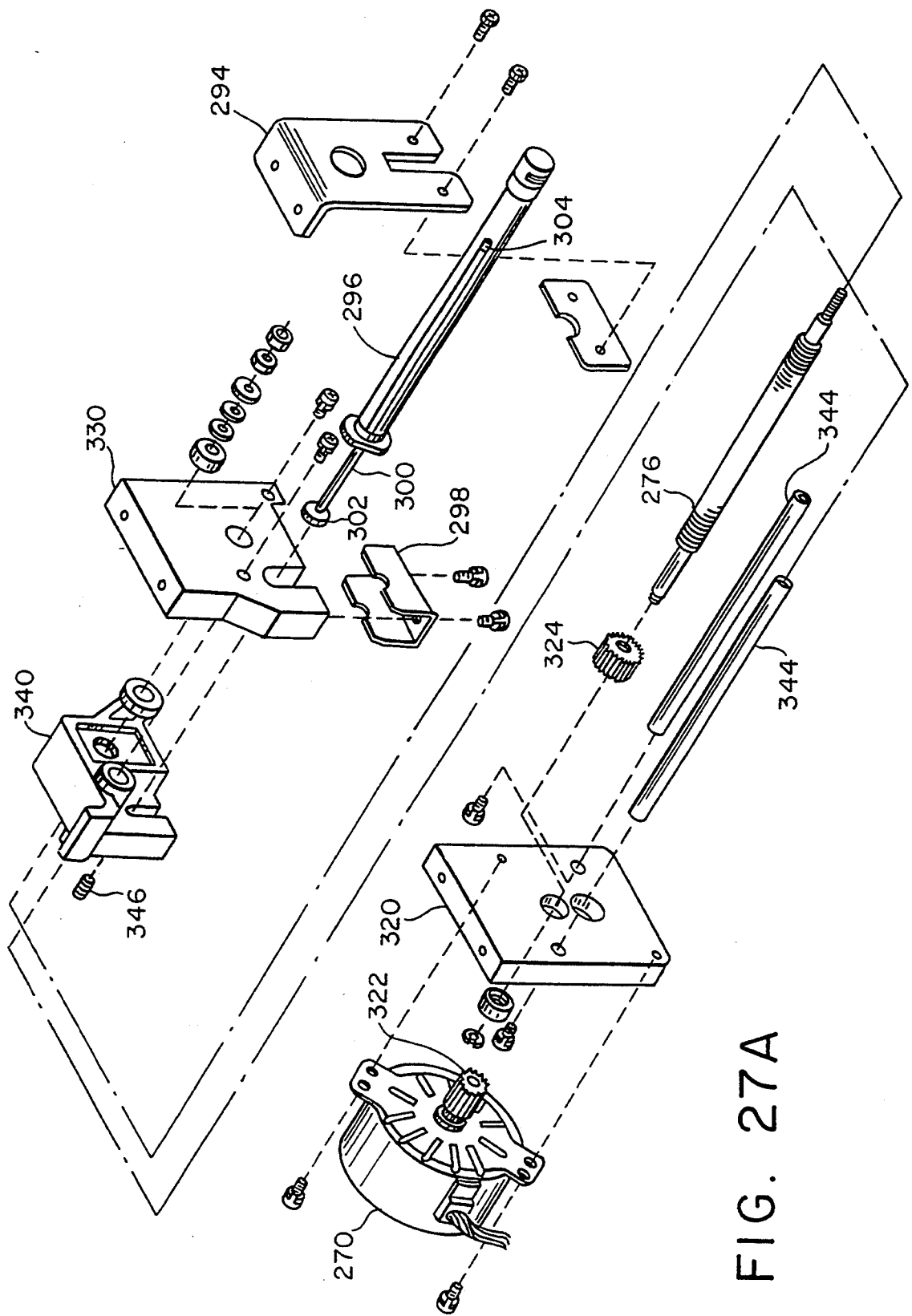
FIG. 27A is an exploded view, in perspective, of the metering device shown in FIG. 27.
Figure 32B:
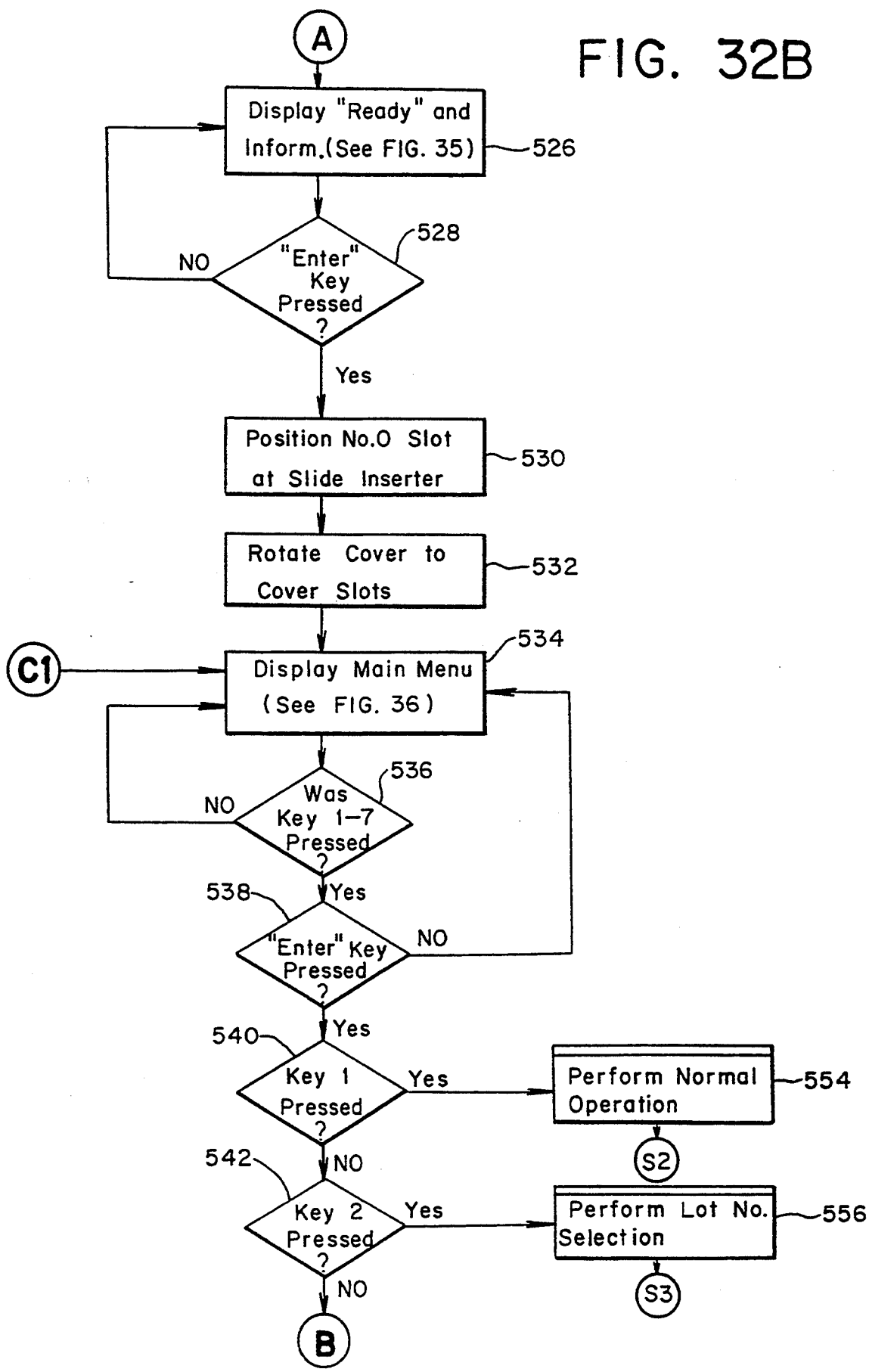
Figure 32C:
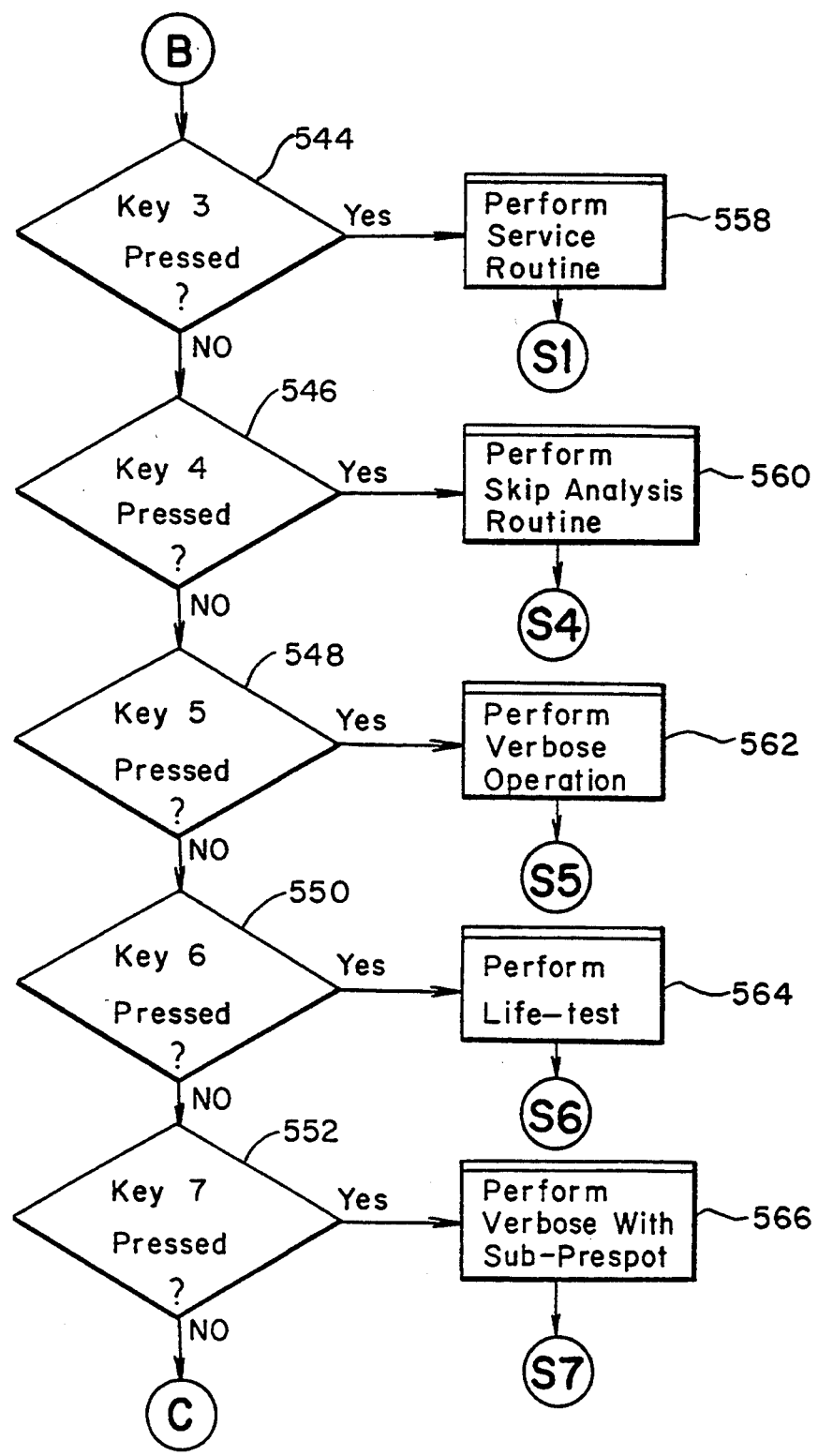
Figure 32D:
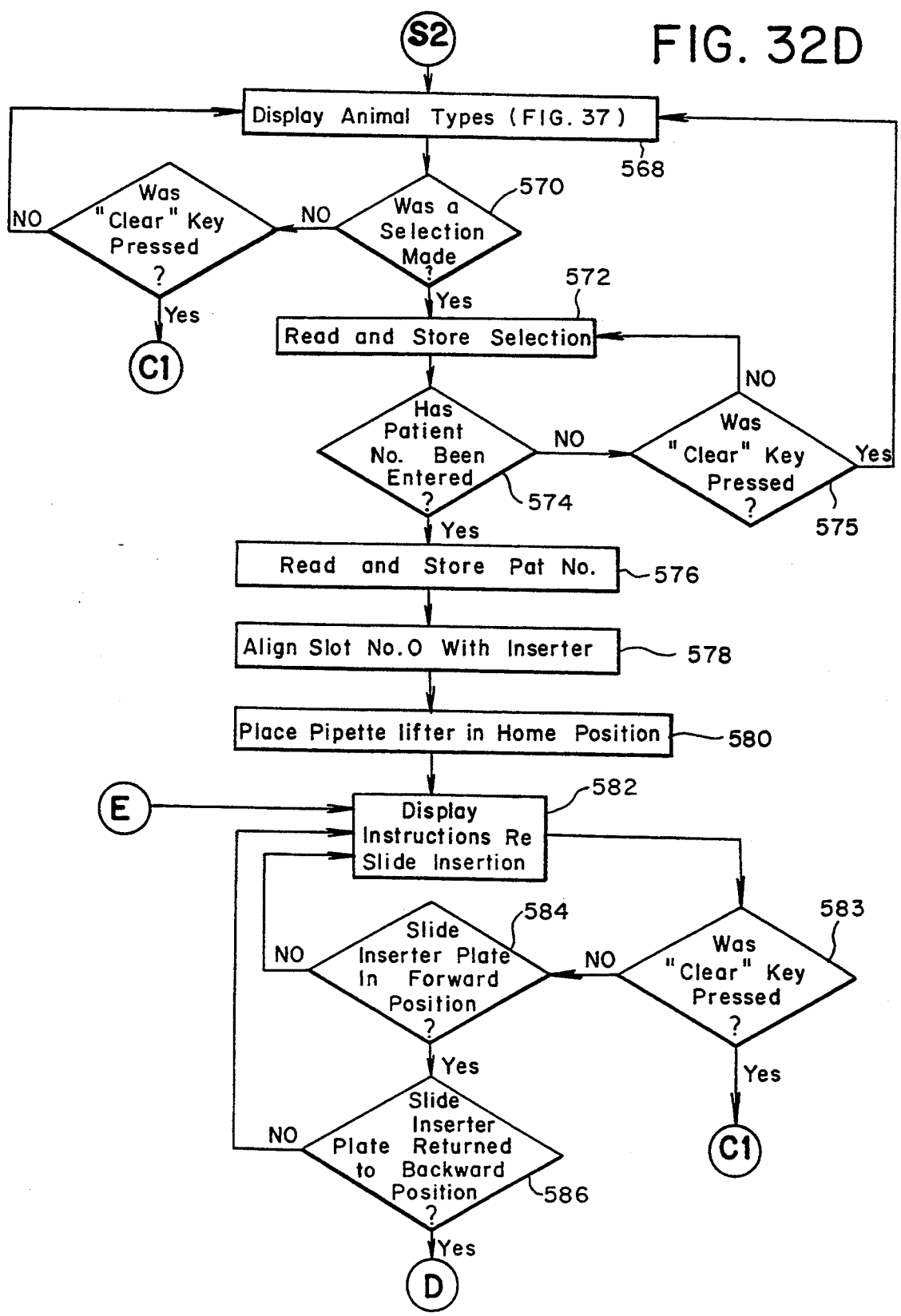
Figure 32E:
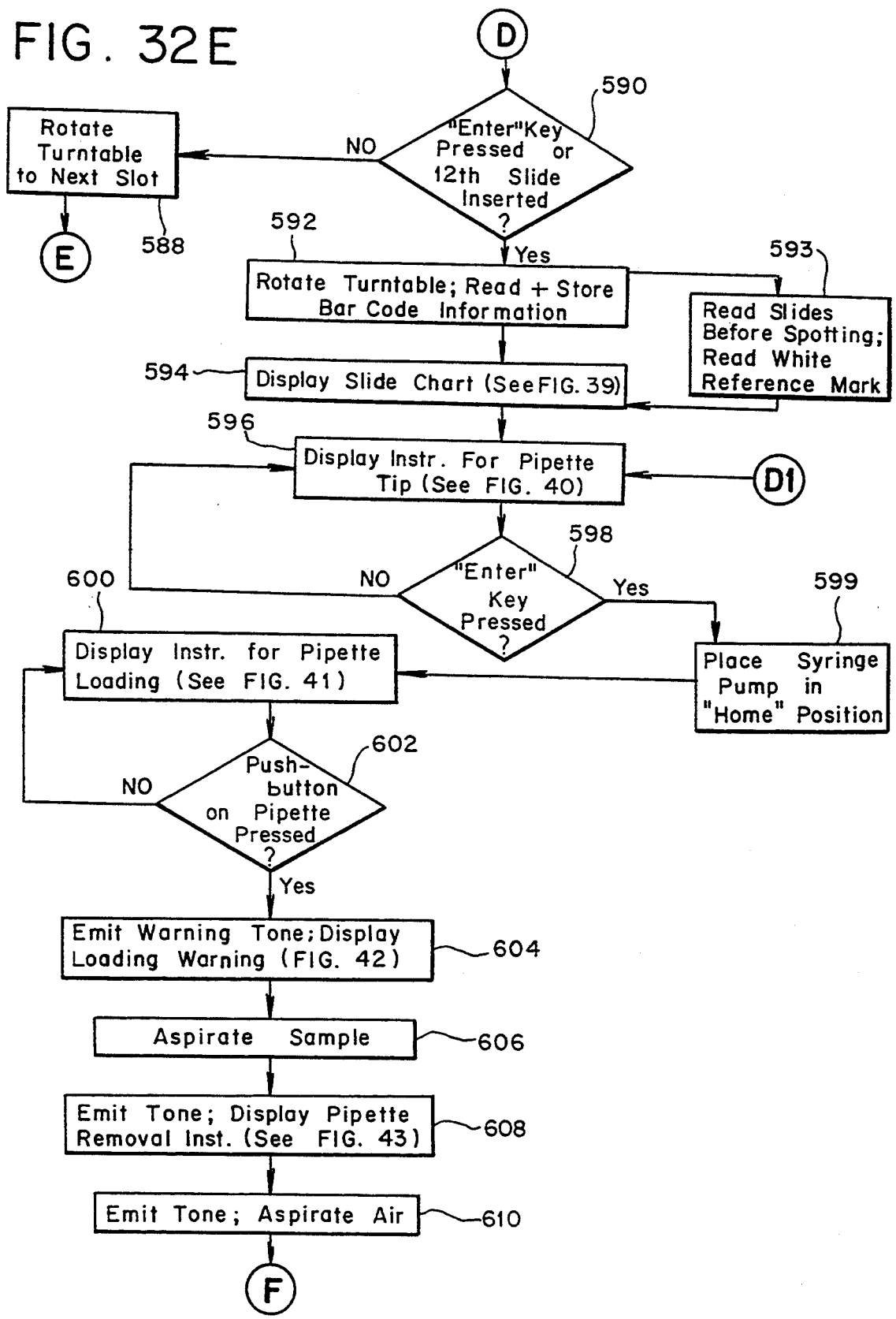
Figure 32F:
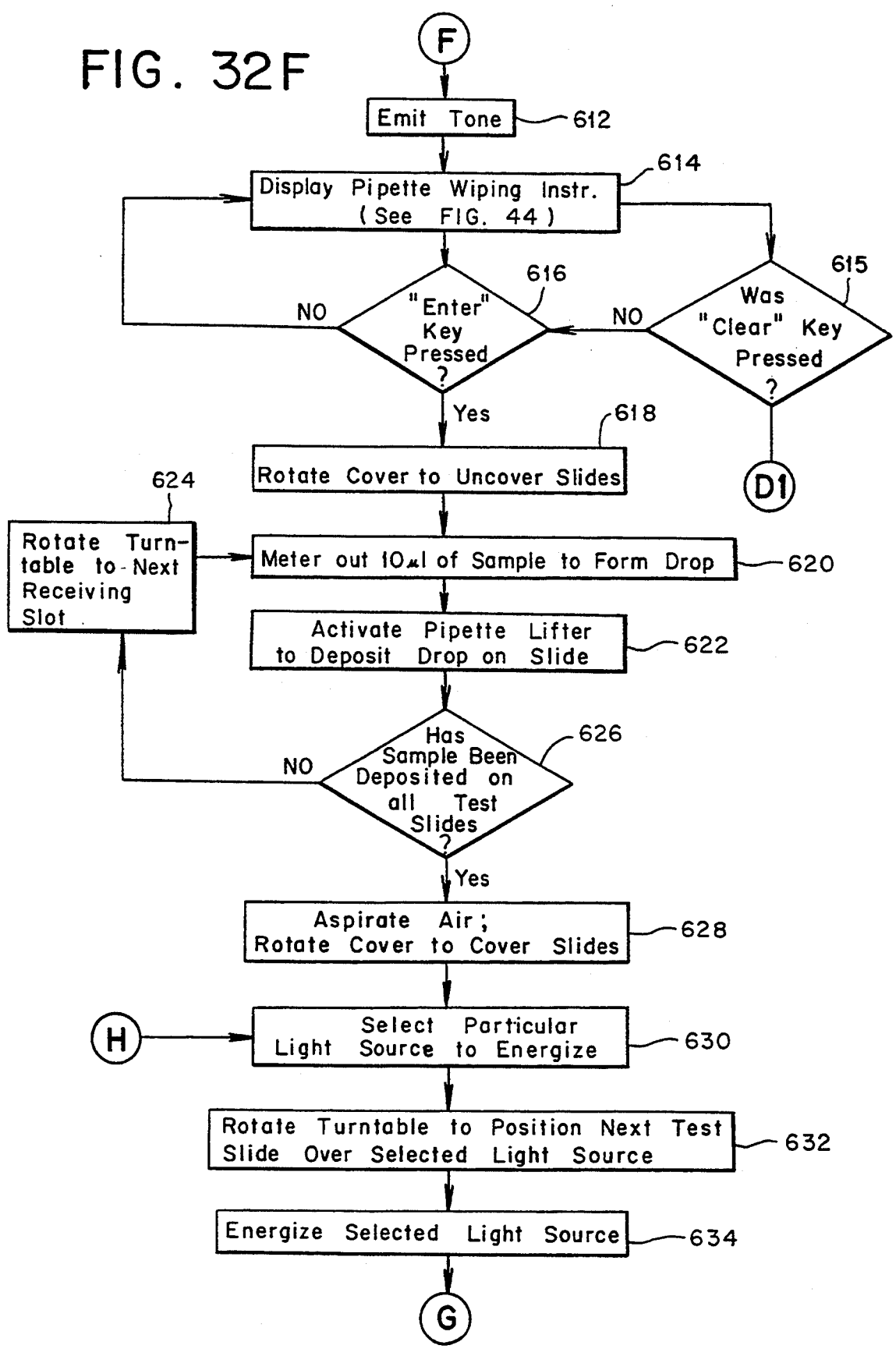
Figure 32G:
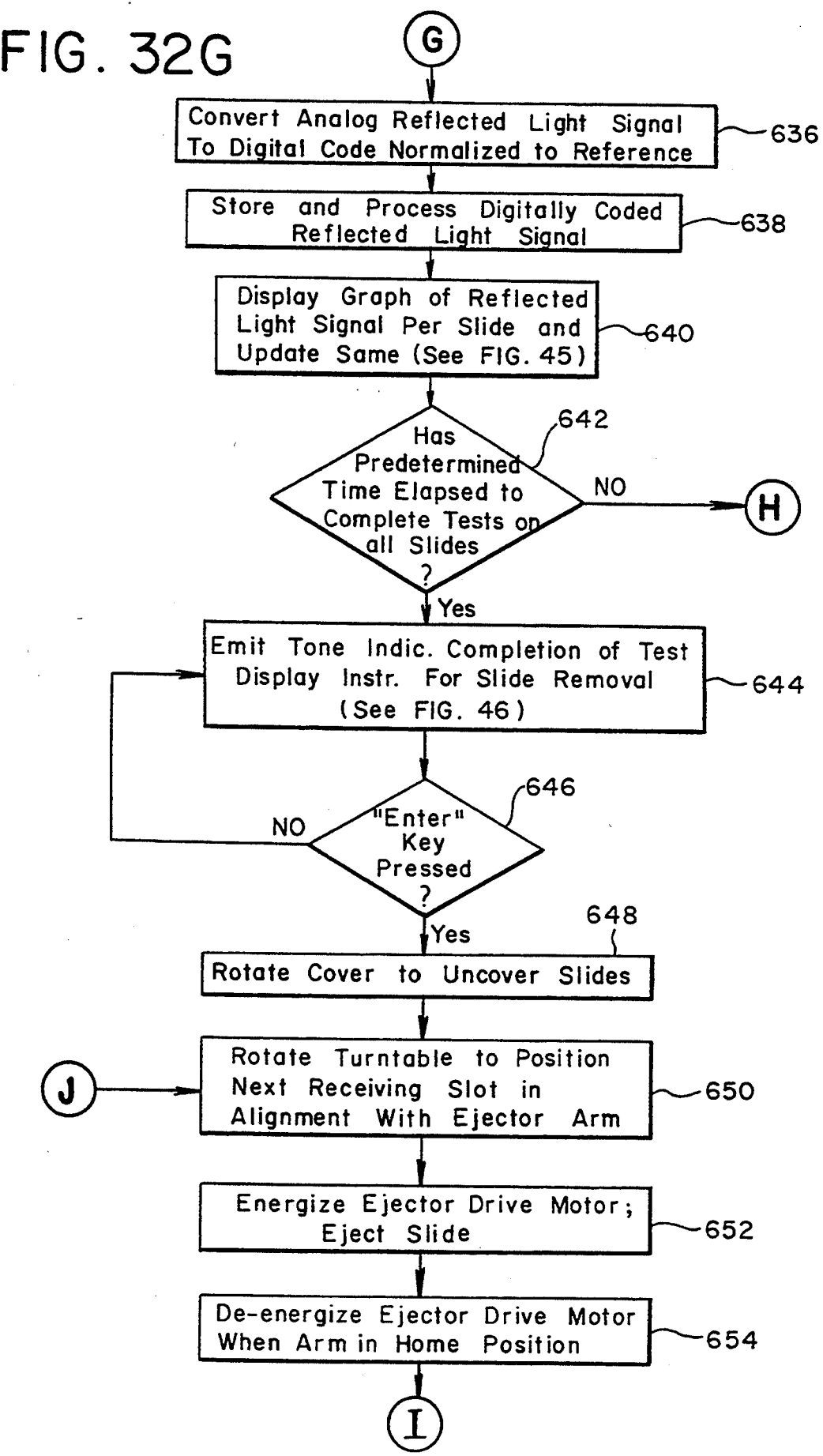
Figure 32H:
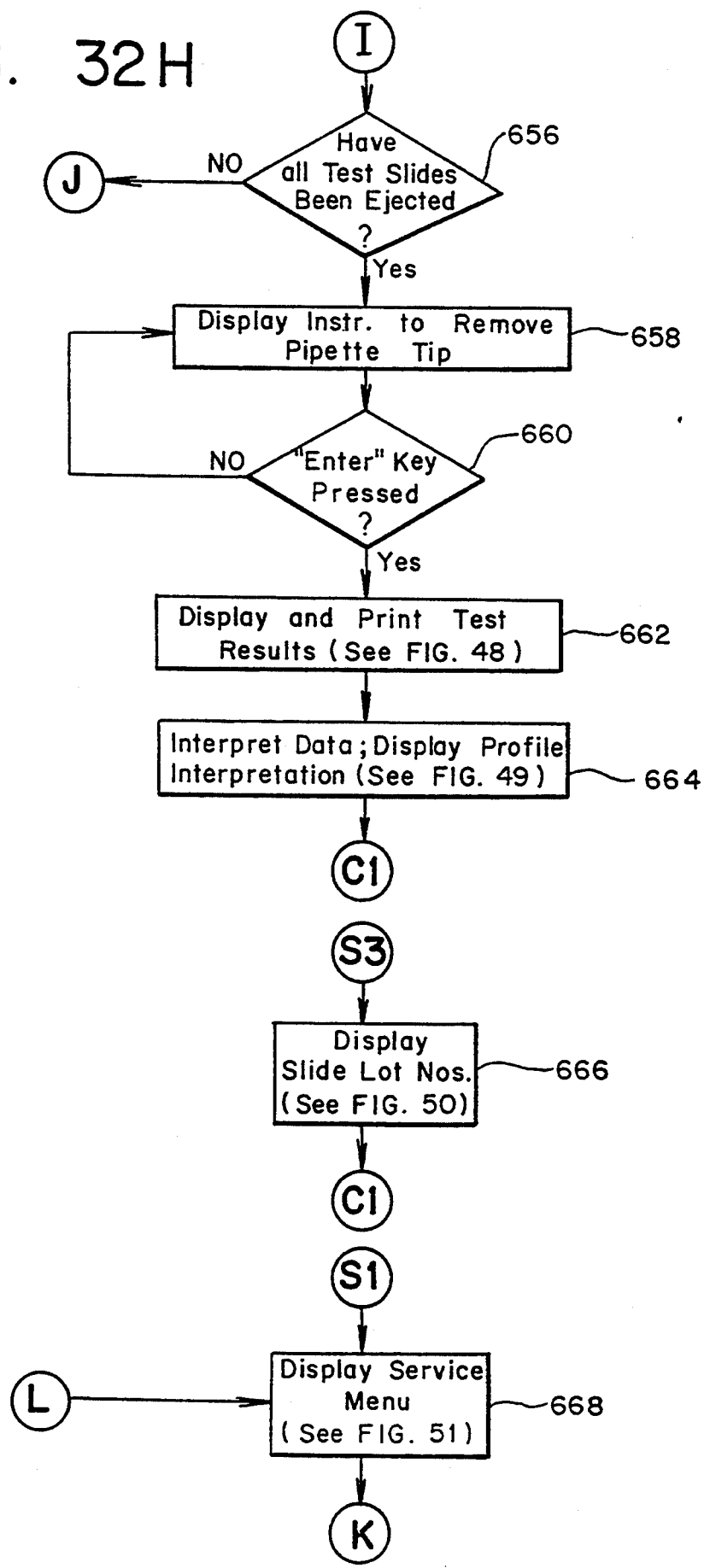
Figure 32I:
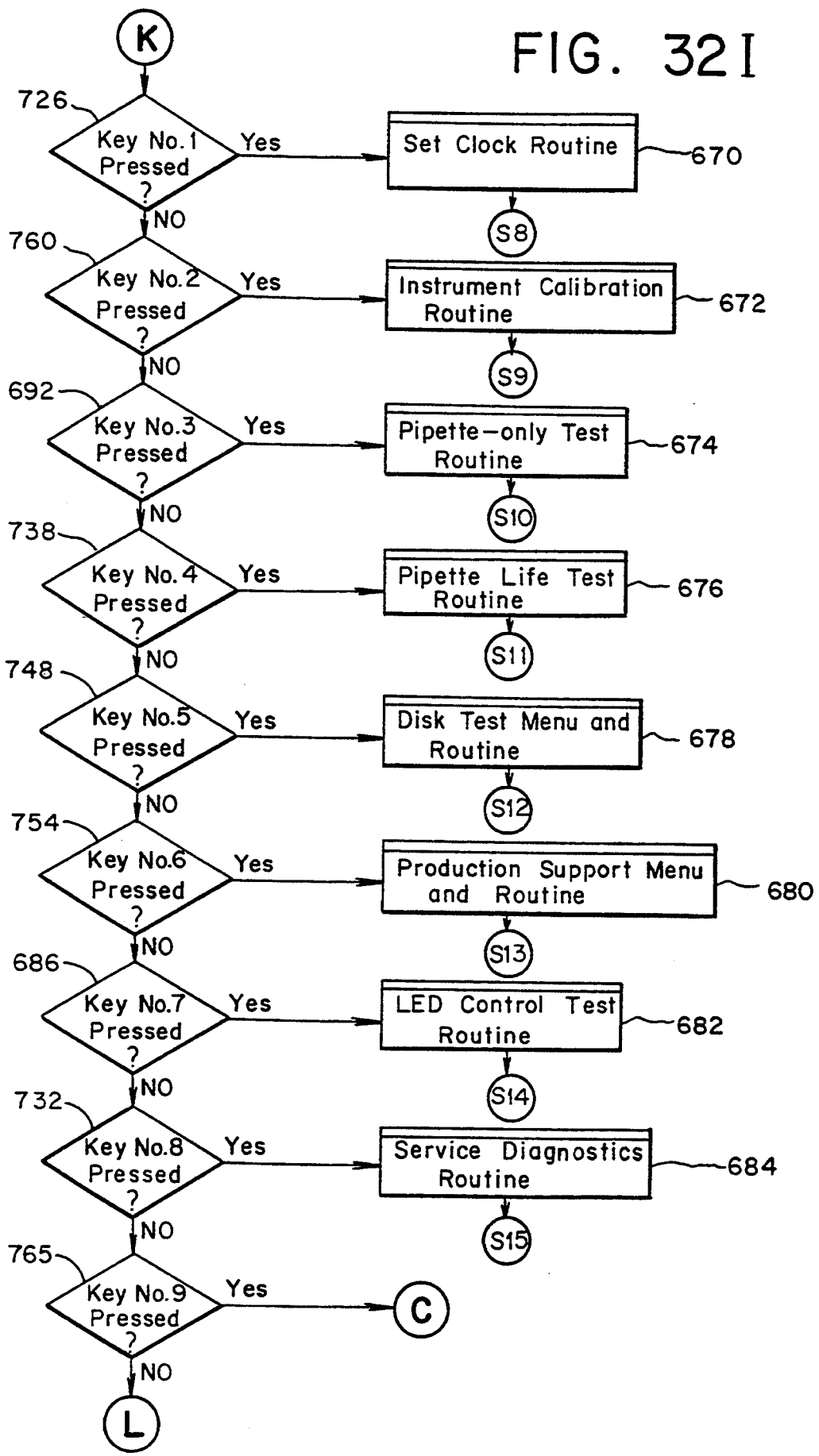
Figure 32J:
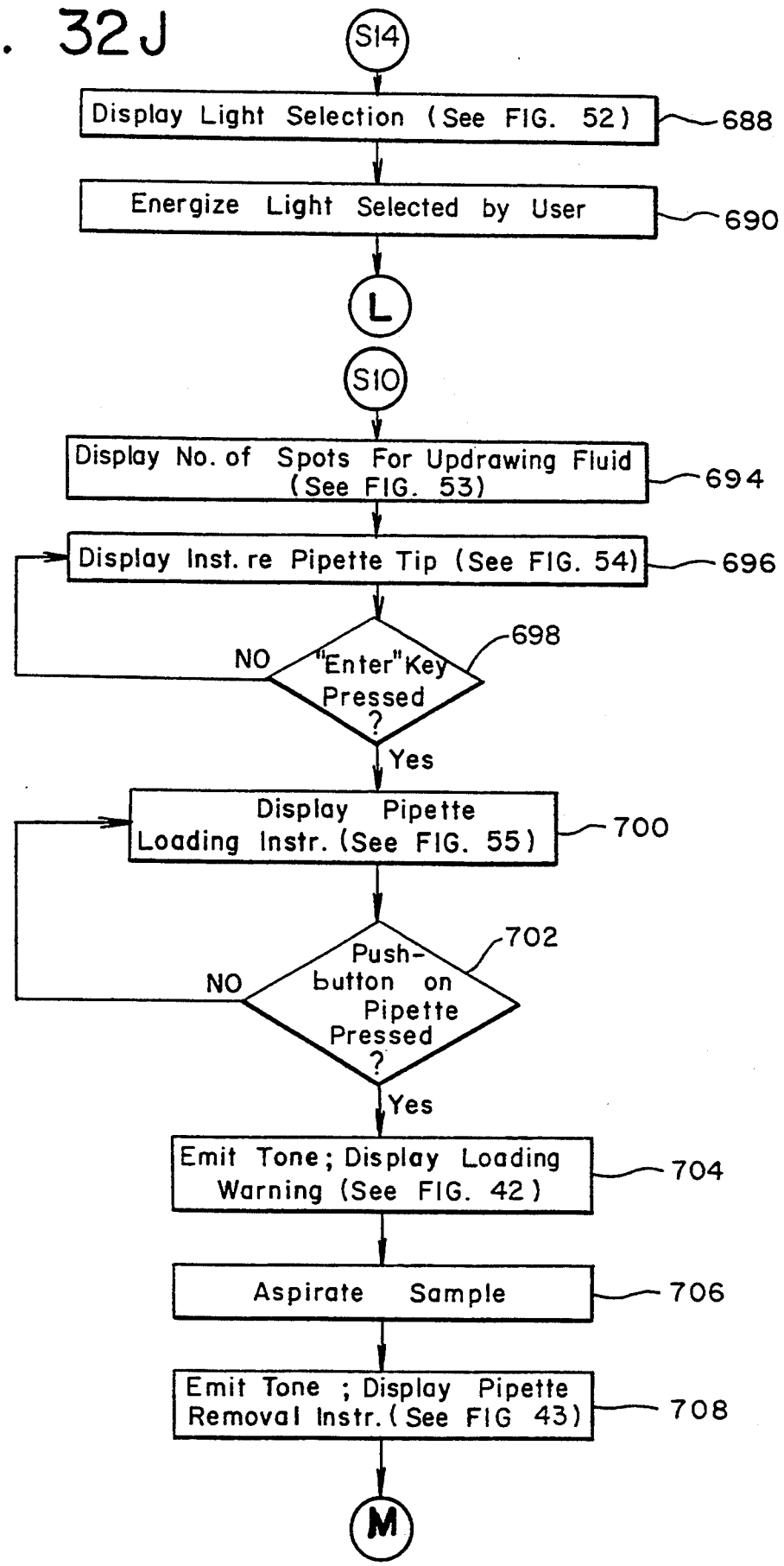
Figure 32K:
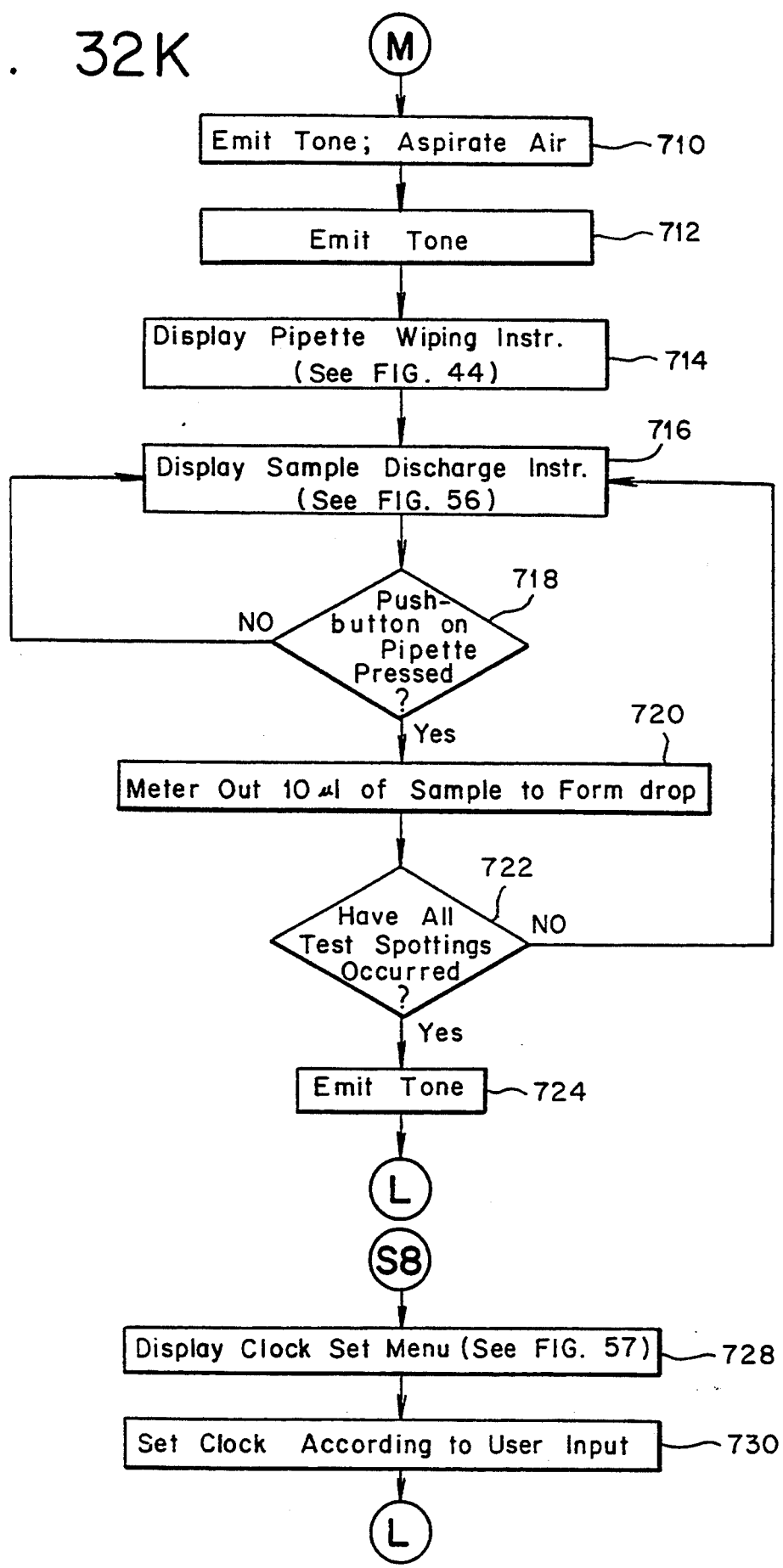
Figure 32L:
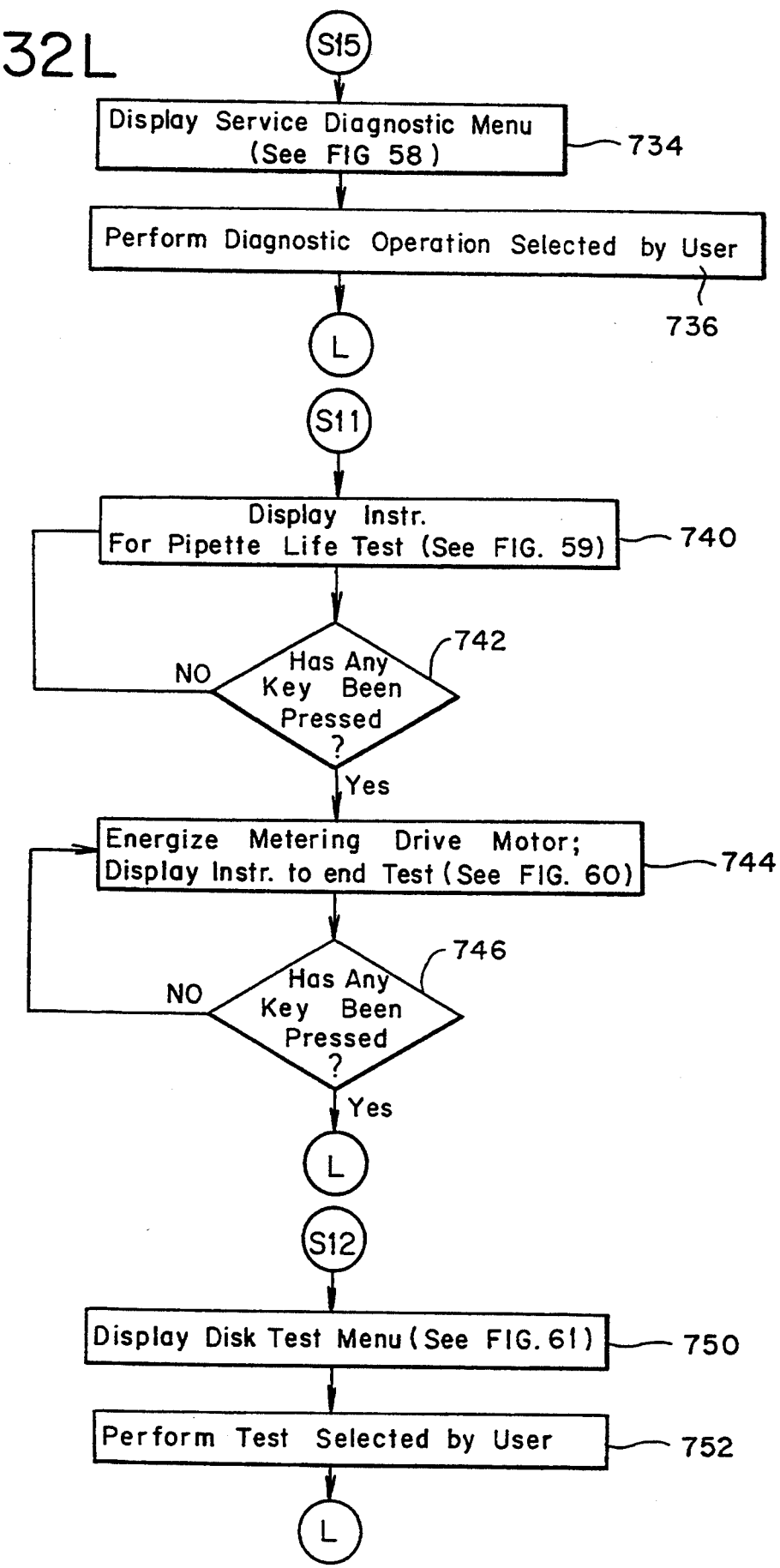
Figure 32M:
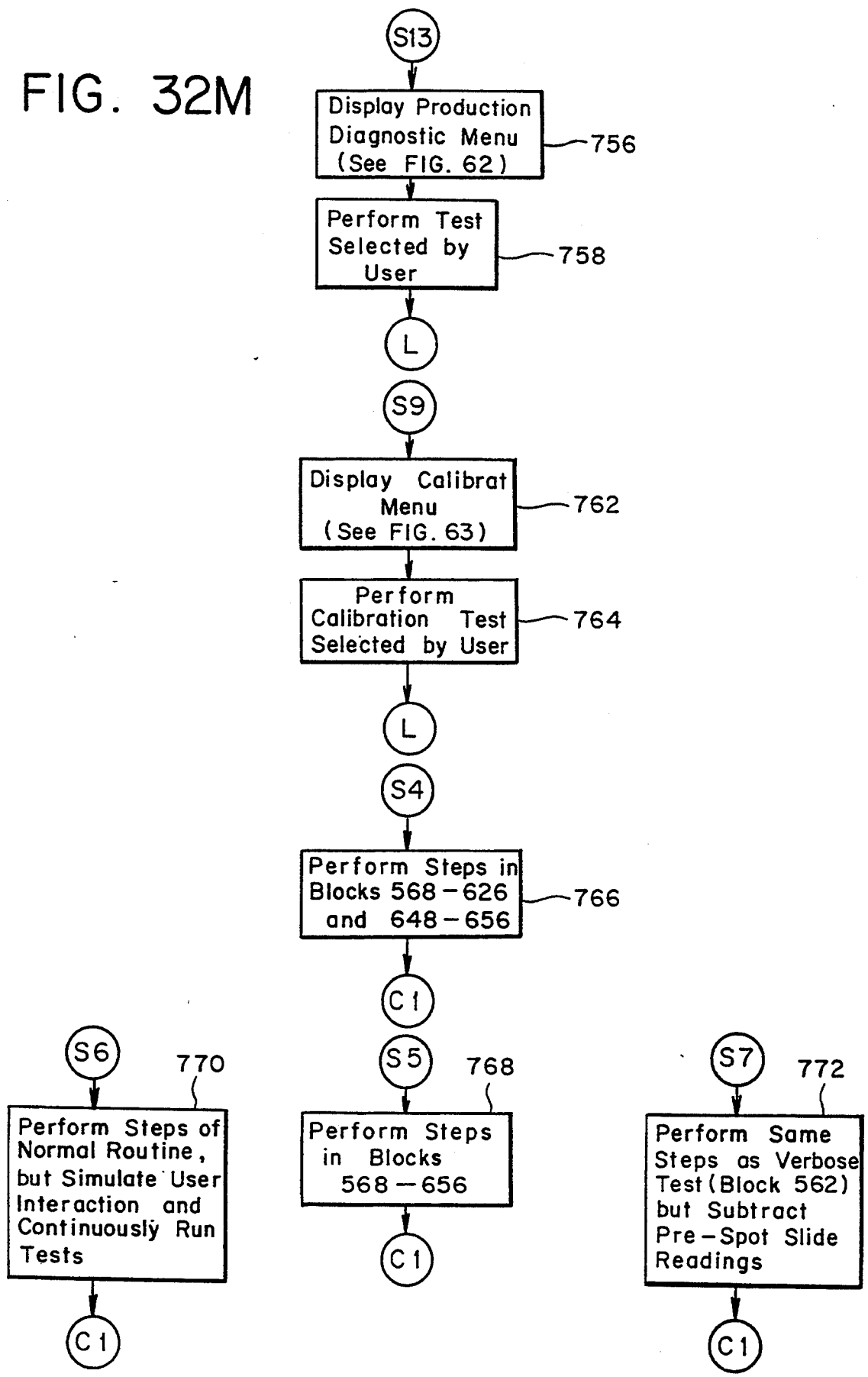

FIGS. 27, 27A and 28 illustrate an alternative form of the metering assembly of the present invention. The DC reversible stepping motor 270 is mounted on a mounting block 320 which is attached to the underside of the base plate 48. A pinion gear 322 is mounted to the drive shaft of the motor 270. The pinion gear 322 engages another gear 324 mounted on the lead screw 276. The lead screw 276 is mounted on one end through the mounting block 320. A ball bearing bushing 326 surrounds the end of the lead screw to minimize friction. A spring clip 328 is fitted into a circumferential slot formed in the end of the lead screw 276 so that the lead screw is rotatably secured to the mounting block 320.

The other end of the lead screw 276 is mounted rotatably through an end support block 330 also attached to the underside of the base plate 48. Again, a ball bearing bushing 332 surrounds the end of the lead screw and is housed by the end support block 330. The end of the lead screw extends through the end support block 330 and is retained in place by a bellville washer 334, followed by a flat washer 336 and two nuts 338.

As in the previous embodiment, a preferably plastic guide or movable block 340 having brass threaded nut 342 internally mounted in the guide block 340 is mounted on the threaded portion of the lead screw 276. Two guide rods 344 extend between the end support block 330 and the mounting block 320 and through the plastic guide block 340 to prevent the guide block from turning relative to the lead screw 276.

The guide block 340 includes a T-slot 292 formed in one surface, as in the previous embodiment, which receives the enlarged head 302 of the plunger 300 of the syringe assembly. Once the head 302 of the plunger is properly inserted into the T-slot 292, a set screw 346 threadingly secured to the mounting block 320 may be tightened against the enlarged head 302 to secure the plunger and syringe in place. The operation of this embodiment of the metering assembly is similar in most respects to the previous embodiment described.

THE ROTATABLE TURNTABLE DRIVE ASSEMBLY

Figure 18:
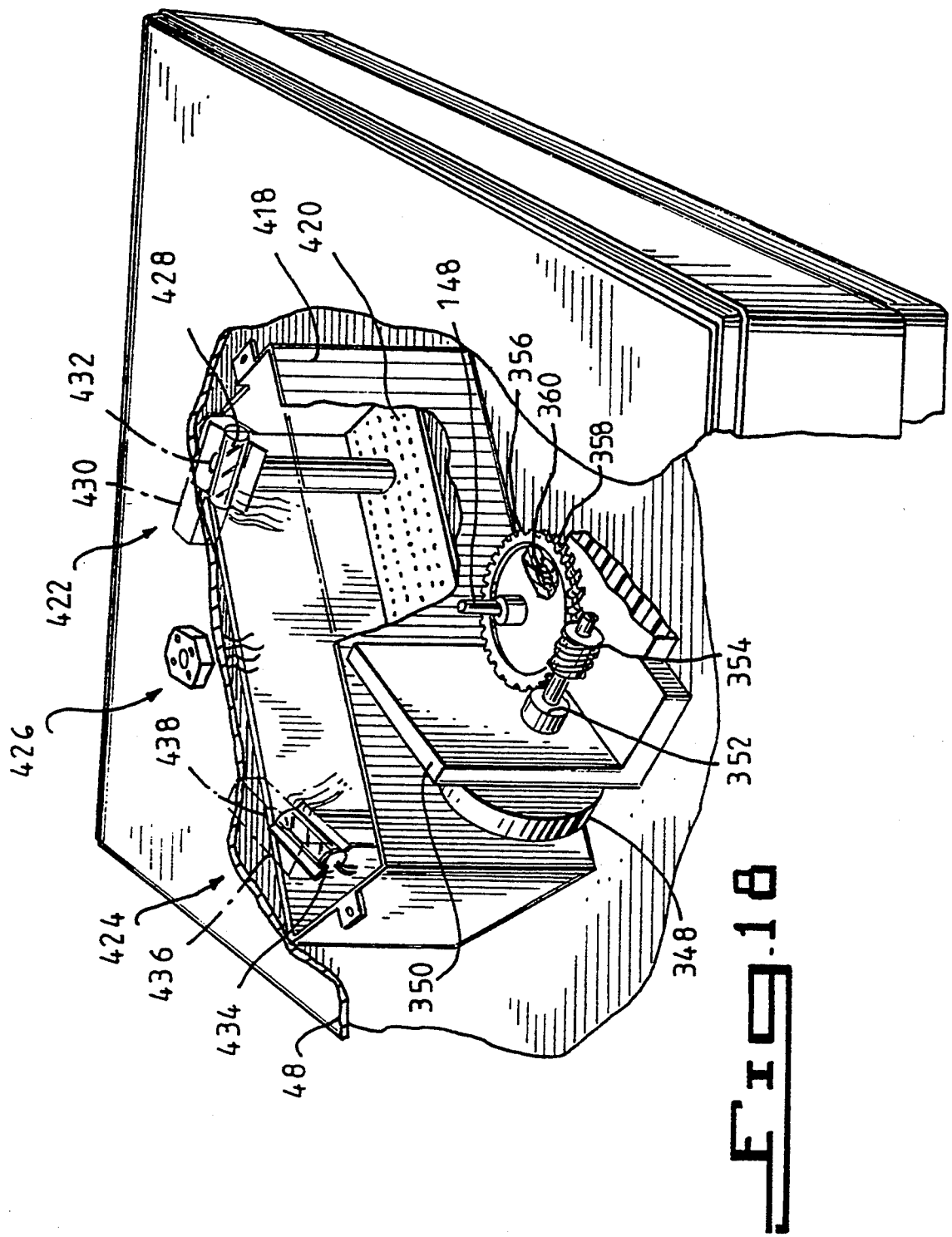
FIG. 18 is a top perspective view partially broken away, illustrating the drive mechanism of the turntable of the chemical analyzer in accordance with one form of the present invention.
Figure 26:
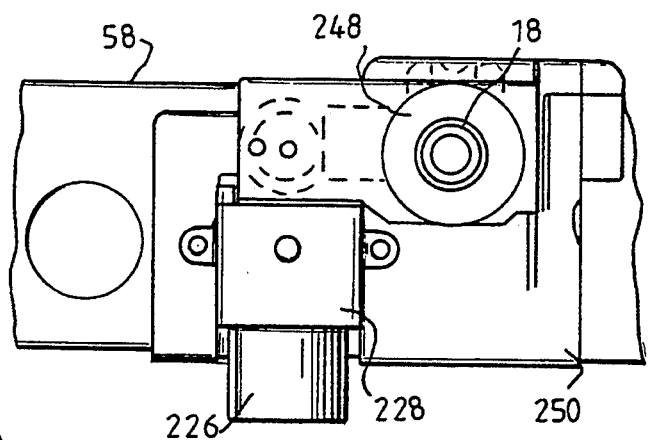
FIG. 26 is a top elevational view of the metering device shown in FIG. 25.
Figure 30:
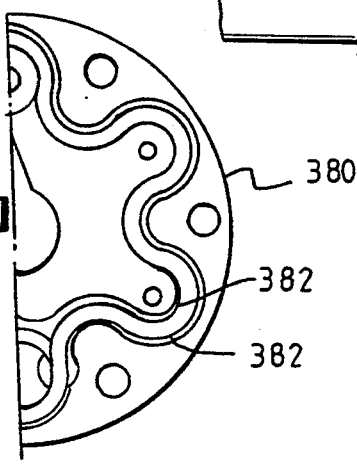
FIG. 30 is a partial bottom view of a heater mechanism for the turntable of the present invention.
Figure 25:
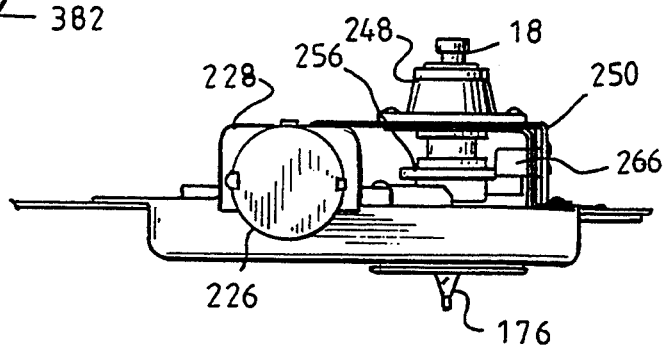
FIG. 25 is a front elevational view of the metering device of FIG. 22.
Figure 29:
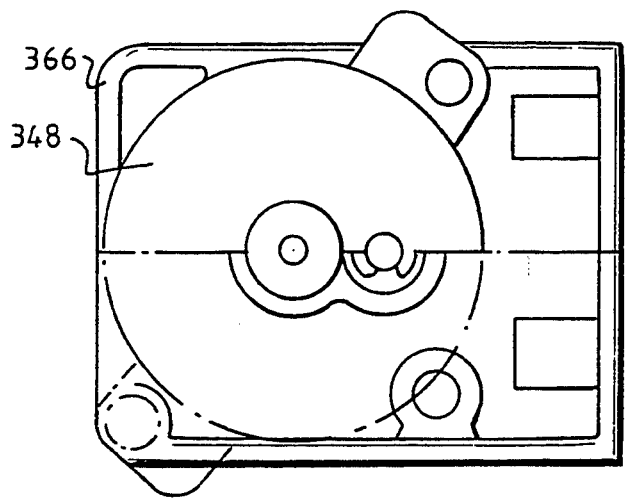
FIG. 29 is a top plan view of a portion of the drive mechanism shown in FIG. 19.

FIGS. 14, 17 and 18 illustrate one form of the drive mechanism for rotating the turntable of the chemical analyzer. The drive mechanism includes a DC reversible stepping motor 348 which is mounted to a supporting bracket 350 attached to the underside of the base plate 48. The drive shaft of the motor 348 passes through an opening formed in the supporting bracket 350 and is connected, by way of a coupler 352, to a helical gear 354 that extends between the drive shaft and an opposite wall 356 of the supporting bracket 352.

The helical gear 354 engages a pair of concentrically mounted drive gears 356, 358 having peripheral teeth, each drive gear being of the same diameter. The drive gears 356, 358 are mounted on the vertically disposed spindle 148 on which the turntable 50 is fixedly mounted. The upper gear 356 is fixedly mounted to the spindle 148. The lower gear 358 is loosely mounted on the spindle 148, but connected by a spring 360 to the upper gear 356. This arrangement minimizes the backlash between the helical gear 354 and the drive gears 356, 358 when the turntable is rotated in opposite directions.

The spindle 148 on which the rotatable turntable 50 is mounted is supported at one end by the bracket 350 and passes through the base plate 48 of the analyzer.

In one form of the present invention, as shown in FIG. 10, the rotatable turntable 50 is secured to the spindle 148 by a hub 362 mounted on the turntable. The hub 362 includes a notch 364 formed in its side wall, which notch 364 is adapted to receive part of the pin 149 used for opening and closing the cover 54.

An alternative form of the turntable drive mechanism and the turntable is illustrated by FIGS. 8A, 19, 29 and 30. The drive motor 348 is mounted vertically on the underside of the base plate from a mounting bracket 366. A pinion gear 368 mounted on the drive shaft of the motor 348 directly drives a pair of superposed gears 370, 372 mounted on the spindle 148 of the turntable. The upper gear 370 is fixedly mounted to the spindle 148 (or to the turntable 50), while the lower gear 372 is rotatably mounted on the spindle but coupled to the upper gear by way of one or more springs 374. As with the other previously described embodiment of the turntable drive mechanism, the arrangement of the two turntable gears 370, 372, is to minimize backlash.

A shallow recess 376 is formed in the underside surface of the turntable. The recess 376 houses a printed circuit board 371 (see FIG. 8A) used for sensing the temperature of the turntable. Mounted closely within another recess 377 formed in the underside surface of the turntable is a heat sensing device 378, such as a thermocouple, which is also mounted on an end of the printed circuit board 371 and which senses the temperature of the turntable 50 by heat conduction. The thermocouple 378 is connected to the associated circuitry of the analyzer as will be explained.

An insulating material 373 is provided on the bottom of the printed circuit board to prevent damage to the circuit board and its components.

A heater plate 380 (see FIGS. 8A and 30) which includes a recess formed in one of its top or bottom surfaces houses a number of conductor windings or heater elements 382, such as manufactured by Kurabe Wire and Cable Co., and is positioned on the spindle 148 adjacent to and underneath the turntable 50. Heat from the elements 382 is spread by the heater plate 380 and is conducted to the turntable in order to maintain the temperature of the test slides within a predetermined range.

A second insulator 384 is mounted below the heater plate 380, and adjacent the insulator 384 is mounted a printed circuit board 386 containing a number of slip rings (not shown).

In one form of the present invention, there are three slip rings provided on the circuit board 386: one slip ring is a common conductor; another slip ring is for providing power to the heater plate 380; and the third slip ring is for providing the signal from the sensor 378 and its associated printed circuit board to the other electronic circuitry of the analyzer.

Mounted through an opening of the base plate 48 of the analyzer is a brush assembly 388. The brush assembly 388 includes three upstanding brushes or contacts 390 which are spring loaded. The contacts 390 contact the slip rings on the printed circuit board 386. The combination of the slip rings and brush assembly provide electrical continuity to the heater plate 380 and the components of the sensor printed circuit board while the turntable 50 is rotating.

In order for the rotatable turntable 50 to be properly aligned with the slide inserter 14, ejector mechanism (which will be described) and pipette assembly 16, a "home" position of the rotatable turntable 50 is sensed optically. Mounted generally on the underside of the turntable 50 (and more specifically on the bottom surface of the heater plate 380) and rotatable with the turntable is an L-shaped bracket having a downwardly protruding leg 392 (see FIGS. 8A and 17). Extending upwardly through the base plate 48 of the analyzer is an optical sensor 394 including a pair of spaced apart LED light source and light detector. The optical sensor 394 and the downwardly extending leg 392 are situated radially with respect to each other such that, as the turntable 50 rotates, the leg 392 will pass between the light source and the detector breaking the light beam between the two.

The downwardly extending leg 392 is positioned at a particular point on the rotatable turntable 50 circumferentially. When the leg passes between the light source and detector of the optical sensor 394, the sensor will signal the associated computer and circuitry of the analyzer. The computer is programed to provide the stepping drive motor 348 with a predetermined number of pulses to drive the turntable clockwise or counterclockwise from the time the signal from the optical sensor is received in order to align a particular receiving slot 52 with any one of the slide inserter 14, the pipette assembly 16, and the ejector mechanism.

It should be noted that the base plate 48 is also maintained at a constant temperature. To accomplish this, a plurality of heaters 395 are mounted to the underside of the base plate 48 (see FIG. 14). Alternatively, a strip heater not shown) may be mounted to the base plate 48 to maintain a constant temperature. The strip heater is basically an elongated coil inside a silicon jacket which is disposed in a circle on the underside of the base plate. Such a device is manufactured by Kurabe Wire and Cable Co., and is similar to heater element 382.

THE SLIDE ELECTOR MECHANISM

FIGS. 14, 20 and 21 illustrate a preferred form of an ejector mechanism 396 which removes the slides from the rotatable turntable generally after the tests have been completed.

The slide ejector 396 basically includes a DC drive motor 398 mounted to an L-drive reduction gear box 400. The motor 398 and the L-drive reduction gear box 400 are mounted to the base plate 48 of the analyzer and positioned, for the most part, on the underside of the base plate.

The drive shaft of the motor 398 is disposed vertically. Therefore, the output shaft of the L-drive gear box 400 is disposed horizontally and positioned slightly below the underside of the base plate.

A hub 402 is mounted onto the gear box shaft, and an elongated ejector arm 404 is mounted in a key slot formed in a peripheral wall of the hub 402.

The ejector arm 404 is positioned in alignment with an opening 406 formed in the base plate 48 of the analyzer and has a length which is such that it will extend through the receiving slots 52 formed in the rotatable turntable and contact a test slide 71 in the receiving slot of the turntable when the receiving slot is positioned to be in alignment with the ejector arm 404.

When the test slides are to be unloaded from the turntable, the turntable is rotated until a receiving slot 52 is positioned in alignment with the ejector arm 404. The computer and electronic circuitry of the analyzer then energizes the drive motor 398, which causes the ejector arm 404 to rotate upwardly through the base opening 406. The ejector arm 404 contacts the edge of the slide 71 in the receiving slot 52 aligned above it and pushes the slide out of the open end of the receiving slot.

The arm 404 continues to rotate until it reaches its initial position at which time the drive motor 398 is de-energized by the computer and electronic circuitry and the movement of the arm stops. The initial or "home" position of the arm 404 is detected by using an optical sensor 408 such as the reflective type described previously or the LED/detector type, mounted on the underside of base 48 and adjacent to arm 404.

After a test slide 71 has been removed from the receiving slot 52 by the ejector, the turntable 50 is again rotated until the next adjacent receiving slot is positioned in alignment with the ejector arm 404. The computer and associated circuitry will then energize the drive motor 398 of the ejector to eject the test slide in that receiving slot. The sequence repeats itself until all of the test slides have been unloaded from the rotatable turntable 50.

As a slide 71 is removed from a receiving slot 52, it passes through a discharge opening 410 formed in the base plate 48 and is caught by the slide drawer 24 which is partially positioned under the slide discharge opening 410 formed in the base plate (see FIG. 4). The bottom of the slide drawer 24 includes a protruding lip 412 which catches on the edge 413 of the analyzer base to prevent the drawer from inadvertently sliding open.

An upstanding cowling 414 is mounted on the top surface of the base plate 48 and partially surrounds the slide discharge opening 410. The cowling 414 may include outwardly flared ends 416 which define an open side of the cowling between them. The cowling 414 is used to guide the test slide 71 into the discharge opening 410 as it is being removed from the turntable 50 (see FIG. 7).

THE REFLECTOMETER ASSEMBLY OF THE ANALYZER

FIGS. 18 and 31a, 31b and 31c illustrate the reflectometer assembly of the analyzer. The assembly is generally enclosed by a rectangular housing 418 secured to the underside of the base plate 48. The reflectometer assembly basically includes a printed circuit board 420 containing associated circuitry, and several light sources, generally designated by references numerals 422–426. The first light source 422 includes a fluorescent lamp or tube 428 emitting a light having a frequency of between about 390 and about 405 nM and is optimally about 400 nM. The fluorescent tube 428 is mounted on one side of a block 430 having a bore 432 extending through its thickness at a predetermined angle of slope with respect to the vertical. The block 430 is mounted on the top surface of the base plate 48, with the fluorescent tube 428 situated below it, and is situated over a cutout 431 formed through the thickness of the base plate 48. The block 430 is situated on the base plate 48 with respect to the turntable 50 such that light emitted by the fluorescent tube 428 through the bore of the block will impinge directly on and at a particular angle to the underside of the film portion 124 of a test slide 71. An ultra-violet bandpass filter 429 is interposed between the fluorescent lamp 428 and the test slide and is preferably mounted in the bore 432 of block 430.

A second light source 424 also includes a fluorescent lamp or tube 434 is mounted in a similar manner as that described for light source 422. This fluorescent tube 434 emits a light having a frequency in the range of about 345 to about 355 nM and is optimally about 350 nM. The second fluorescent tube light source 424 also has a block 436 having a bore 438 associated with it, which block is mounted on the base plate 48 over a second cutout 439 formed in the plate similar in structure to that previously described in relation to the first fluorescent tube light source 422. As with light source 422, light source 424 includes an ultra-violet bandpass filter 440 interposed between the fluorescent lamp 434 and the test slides and preferably is mounted in the bore 438 of block 436.

The two fluorescent tube light sources 422, 424 are particularly situated with respect to each other and to the rotatable turntable 50 such that they are adapted to form a light beam emitted by their respective fluorescent tubes on the bottom of the film portion 124 of a test slide located in a receiving slot 52.

As mentioned previously, the receiving slots 52 of the turntable 50 are preferably formed to be larger than the exposed film portion 124 of the test slide so that the receiving slot does not interfere with the light impinging on the test slide.

A first collimating lens 442 is mounted in an opening 444 formed through the thickness of the base plate 48 directly below a receiving slot 52 aligned with it. The collimating lens 442 is surrounded by a closed cylindrical tube 446 which extends upwardly from the printed circuit board 420 of the reflectometer assembly. The closed tube 446 ensures that no light enters the reflectometer assembly to interfere with the light received by the collimating lens 442. The lower end of the tube 446 surrounds a photodiode mounted 448 on the printed circuit board 420. Light from the first fluorescent lamp 428 is reflected from the test slide 71 and is received by the photodiode 448 through the lens 442. The tube may also include an optical stop 447 positioned between the lens 442 and the photodiode 448 to prevent any stray light from being received by the photodiode and affecting the measurements. Optical stop 447 includes an aperture through its thickness.

A similar arrangement as described above is provided for the second fluorescent tube light source 424. More specifically, a second collimating lens 450 is mounted in an opening 452 in the base plate 48 directly below another receiving slot of turntable 50 and a second cylindrical tube 454 is disposed between the collimating lens 450 and the printed circuit board 420. The lower end of the second tube 454 also completely surrounds and encloses a second photodiode 456 mounted on the printed circuit board. The second tube also preferably includes an optical stop 449 between the lens 450 and the photodiode 456.

An optical sensor, such as a photodiode 457, 459, is positioned partially in the light beam emitted by the fluorescent tubes 428, 434 for the purpose of determining the amount of light which is directed onto the test slides. This information is used as a reference and is compared to the light which is reflected from the test slides and detected by the photodiodes 448, 456.

Light of a particular frequency emitted by one of the fluorescent tubes 428, 434 forms a beam when passing through the bore of the corresponding mounting block 430, 436, which beam impinges on the bottom of the film portion 124 of a test slide located in a receiving slot aligned with the associated collimating lens 442, 450. A certain amount of light is reflected by the test slide into the collimating lens, which light is received by the associated photodiode 448, 456 through the enclosed tube 446, 454.

A third light source assembly 426 is also provided. The third light source assembly basically includes a mounting block 458 situated on the top surface of the base plate 48, and partially passing through an opening formed in the base plate. The third mounting block 458 includes a plurality of spaced apart bores 460 formed through its thickness. Each bore is sloped to the vertical and, preferably, is at an angle of 45 degrees to the vertical. In a preferred form of the invention, four bores 460 are formed spaced equally distantly about the general periphery of the third mounting block 458.

Four light emitting diodes (LEDs) 462, each emitting a light of different frequency, are mounted in the underside of the third mounting block 458, each LED 462 being received by a corresponding bore 460. The third mounting block 458 is situated on the base plate and with respect to the rotatable turntable 50 such that light emitted by any one of the LEDs will impinge on the bottom of the film portion 124 of a test slide 71 located in a receiving slot.

A bore 464 is formed centrally through the mounting block 458. A collimating lens 466 is mounted in the bore 464 and near the top surface of the block 458. A photodiode 468 is also mounted in the bore 464 and near the lower surface of the block 458. Interposed between the lens 466 and the photodiode 468 and in bore 464 is an infrared rejection filter 470.

Light from any LED 462 impinging on the test slide 71 will be reflected directly into the photodiode 468 through the lens 466 and filter 470. The photodiode will provide a signal indicative of the amount of light reflected to the associated circuitry of the reflectometer.

As mentioned previously, four LEDs 462 are provided, each LED emitting a light of different frequency. The preferred frequencies emitted by the LEDs are in the following ranges: about 555 to about 565 nM; about 585 to about 595 nM; about 635 to about 645 nM; and about 675 to about 685 nM. The optimal frequency for each of the LEDs mentioned above is 560 nM, 590 nM, 640 nM and 680 nM, respectively. Preferably, the latter two LEDs (i.e., 640 nM and 680 nM LEDs) have filters 469 of the desired wavelength (i.e., 640 and 680 nM) positioned in their respective bores 460.

Each of the four LEDs 462 may be individually energized so that a single beam of light having a particular frequency or range of frequencies will be selected to impinge on a particular test slide. Although the fluorescent lamp light sources 422, 424 may be individually energized, they are preferably energized when the analyzer is powered up. Any test slides which have a chemistry that requires one or the other fluorescent source are positioned by the turntable over that source. During the analysis operation, the associated computer and electronic circuitry of the chemical analyzer has stored in memory what test slide is aligned with what light source.

Various tests require various test slides each test slide carrying a different dry analyte. The various test slides must be exposed to light of selected frequencies in order to conduct a reflectometry test. The type of test slide, for example, for a calcium test, is provided by the bar code information 86 on the top surface of the slide, which information is read by the bar code optical scanner 158 and which is provided to the associated computer and circuitry of the analyzer In its memory, the analyzer will associate a particular receiving slot 52 with a particular test slide 71 and will energize the appropriate light source 422–426 during the analysis operation when the slide is positioned over the particular light source. This will be discussed in greater detail during the explanation of the operation of the chemical analyzer.

HOW THE ANALYZER USES REFLECTED LIGHT TO DETERMINE CONCENTRATION

The slides used in the analyzer change in intensity (at certain known wavelengths) according to the concentration of the chemistry in the serum. The analyzer must read the change in intensity and derive the concentration accordingly.

The analyzer software performs this task. The software makes use of the following two equations in order to determine the concentration:

1) $$\text{Percent Reflectance} = \frac{(\text{ACTUAL READING}) - (\text{ABSOLUTE BLACK})}{(\text{ABSOLUTE WHITE}) - (\text{ABSOLUTE BLACK})}$$

The Percent Reflectance is a value between 0 (black) and 1 (white).

2) R.D. (Reflectance density) = $\text{Log}_{10}$ (1/Percent Reflectance)

Reflectance density usually ranges from about 0.1 (white) to about 2.0 (black).

In order for the analyzer to determine these values, it first needs to know the value of ABSOLUTE WHITE and ABSOLUTE BLACK. These are determined by putting slides in the analyzer with known Percent Reflectances when the analyzer is calibrated. These slides are called black and white references. The ACTUAL READING is then taken from these two slides and then by simple algebra the ABSOLUTE BLACK and ABSOLUTE WHITE values are determined. This procedure is referred to as INSTRUMENT CALIBRATION.

Once the absolute values are determined, the analyzer can easily determine the RD value for any slide. There are two types of slides:

1) ENDPOINT slides—The concentration of the sample is determined by taking the RD at a fixed amount of time after the sample was placed on the slide (which is usually about 8 minutes).

2) RATE slides—The concentration is determined by the rate of change in the RD. The rate is determined after the whole analysis has taken place.

First, the INITIAL RATE is determined. This is done by taking the change in RD for almost the whole analysis. During some parts of the analysis, the reaction may not be stable, so these portions are ignored. This INITIAL RATE tells if the ACTUAL RATE is a large or small one. The points to use for determining the INITIAL RATE are predetermined for each chemistry by analyzing various samples of known concentrations.

According to how large the INITIAL RATE was, points are picked to use in determining the ACTUAL RATE. If the INITIAL RATE was high, then points are picked close together (because the chemicals in the slide wear out quickly with high concentration samples). If the INITIAL RATE was low, then points are picked far apart (this provides better accuracy). These points are predetermined according to the chemistry by doing trials of the chemistry with various samples of known concentrations.

A linear regression is done over this range of points (in time) of the reaction to determine the rate.

Now, the ENDPOINT RD or RATE is used to determine the concentration of the sample. Different lot numbers for each slide chemistry have different correlations between this ENDPOINT/RATE and the concentration. These correlations are predetermined by analyzing various samples of known concentrations. A chart or table for each different correlation is made, for example:

| GLUCOSE lot 4567: concentration (mg/dl) | R.D. |
| --- | --- |
| 0 | 0.0500 |
| 32 | 0.1976 |
| 191 | 0.5961 |
| 396 | 0.9216 |
| 480 | 1.0200 |

This is called a CHEMISTRY CALIBRATION CURVE. By doing a linear interpolation of the sample's known RD, one can determine the concentration. For example, if the RD was 0.7854, then the concentration would be determined as follows:

$$\frac{0.7854 - 0.5961}{0.9216 - 0.5961} = \frac{? - 191}{396 - 191}$$

By simple calculation, one finds that the concentration is 310 mg/dl.

The reflectometer of the analyzer is preferably calibrated in three different ways. The first method, which was described previously, uses black and white reference test slides. The slides are inserted in the receiving slots of the rotatable turntable, and the various light sources 422–426 are energized so that their light impinges on and is reflected by the reference test slides. The reflected light is measured by the analyzer, and data corresponding to the measurements are stored in the analyzer's associated computer.

These measurements are used in the initial calibration of the analyzer envisioned to be conducted at the analyzer manufacturing facility. Because the turntable may "wobble" during rotation or have a thickness which varies slightly about its circumference, not all of the test slides mounted on the turntable may be at the same distance above the light sources of the reflectometer. This variation in distance of the turntable at the respective receiving slots with respect to the light sources may affect the amount of reflected light received by the photodiodes of the various light sources. The computer of the analyzer will associate this measurement data with each respective receiving slot location on the turntable to compensate for any disparity in the reflected light received by the photodiodes of the light sources.

The second method involves rotating the turntable to position a light reference mark situated on the underside of the turntable over each light source. This operation is performed when the analyzer is initially calibrated, but also is repeated each time the analyzer is used to test a sample. During a sample test, the light from each source is directed onto the light reference mark, and the reflected light is measured and compared with measurements taken during initial calibration. This comparison will detect any varying brightness in the light sources for drift in the intensity of the light through the optics of the reflectometer and will compensate for such changes by providing a multiplication factor which is used in the computation of the sample's concentration.

The third method is conducted during a test operation. More specifically, the analyzer will energize one of the light impinge on and be reflected by the unspotted test slides. It is possible that the wavelength of light emitted by the sources is shifted from the optimum desired wavelength (due to the variations in the light sources and associated components used in the analyzer), and this shift in wavelength may affect the accuracy of the measurements, as different amounts of light may be reflected at different frequencies. For example, about a 1% change in the wavelength of light impinging on a calcium test slide may result in about a 6% change in light reflected by the slide. This shift in wavelength will not be detected by the second method of calibration using the white reference spot, as a white color will for the most part reflect light of all frequencies. Accordingly, by "reading" the test slides prior to their being spotted to determine the wavelength shift in the analyzer's light sources (and in particular, the LED light source 426), the analyzer can appropriately adjust the density value after the test slides "develop".

There is another reason why the reflectance of the test slides are read before they are spotted. It may be possible that a previously used slide has been inadvertently reloaded into the analyzer. By looking at the reflectance of the test slides prior to spotting, the analyzer may determine if any test slides were already used and eject the slides.

The chemical analyzer 2 of the present invention is designed to be user friendly. More specifically, the chemical analyzer will provide not only the test results of the analysis and a diagnosis of the possible ailments of the animal being tested, but also will provide instructions on its LCD display 8 for the user to follow during operation of the analyzer. The operation of the analyzer is illustrated by the flow chart shown in FIGS. 32a–f of the drawings.

The first step in the operation of the analyzer is to turn the power switch 28 on (Block 500). When this occurs, the analyzer will load data into its memory from the floppy disk (Block 502) and will initialize the hardware and software, such as by master resetting the components, etc (Block 504).

The analyzer will then not only display but also print out a copyright notice (Block 506; FIG. 33). Once the system has been initialized so that keyboard data may be read, the analyzer will look to see if a particular key (for example, key No. 3) on the keyboard 4 is pressed (Block 508). If it is, this is an indication to the analyzer that a service routine is to be performed (Block 510) as opposed to a normal analysis operation.

If key No. 3 is not pressed, the analyzer will go on to perform a self test of its electrical and mechanical functions (Block 512). For example, it will test to see if the pipette lifting mechanism is operational, whether the cover 54 can be opened and closed and whether the ejector mechanism 396 is operational.

During this time the display will provide information to the user that the incubator is warming (Block 516) (and will display the temperature of the incubator, i.e., the turntable 50) and that a self test is in progress, and will instruct the user to wait until the test has been completed (FIG. 34).

The analyzer will then eject any slides which are left in the analyzer, and find the "home" positions of the ejector mechanism, the pipette lifter, the cover motor and the turntable by moving each mechanism until the optical sensor associated with each mechanism determines the position of the movable components (Block 514). The system then ensures that all of the components are properly aligned for example, that a particular receiving slot (for example slot No. 0) is in alignment with the longitudinal axis of the slide ejector and that the cover pin is in alignment with the cover movement mechanism. All during this period, the heating plate 380 and other heating elements 395 have been energized and the temperature of the turntable 50 is being monitored (Block 516).

Since the slide inserter 14 is manually operated, the inserter plate 68 may be in the wrong position for loading. An alarm or speaker 518 incorporated into the analyzer will be activated to alert the user to grasp the grip 80 and pull the inserter plate to its most backward position on the slide inserter. The incorrect position of the inserter plate 68 is sensed by the first pair of light source 102 and photodetector 104 at this stage in the operation of the analyzer.

The incubator will continue to warm until it reaches a particular range of temperature. The incubator will then be maintained at this particular temperature, which is preferably about 37° C.35 0.2° C. All during the warming process the temperature of the incubator may be displayed (FIG. 34).

The analyzer senses when the incubator has reached the desired temperature (Block 520). It will then start a clock (internal to the software of the associated computer) to allow the analyzer to stabilize in temperature for a predetermined period of time (Block 522).

The analyzer senses when the clock has reached the predetermined period of time (Block 524), which is preferably set for about ten minutes, and will then inform the user that the incubator is ready and that the self test is complete by displaying such information on the display (Block 526) and will also signal the user, who may not be looking at the display, by activating the alarm 518 which emits three loud tones. The user is then instructed to press the "Enter" key (E) on the keyboard 4 to use the analyzer (FIG. 3).

The analyzer will sense when the "Enter" key has been pressed (Block 528) and will then cause the turntable to rotate until the No. "0" assigned receiving slot 52 is in alignment with the slide inserter 14 (Block 530). It will further cause the cover 54 to rotate with respect to the turntable 50 such that the cover covers each receiving slot (Block 532). The cover 54 and the spring clip 116 of each receiving slot helps guide the slides 71 into a respective receiving slot at the proper time in the sequence of operations.

The analyzer will then display to the user the main menu from which the user may select the particular operation desired (Block 534; FIG. 36).

In one form of the invention, there are seven operations which are displayed to the user on the main menu. The first is a normal analyzer operation. The second is a lot number selection. The third operation is a service menu, for testing improper operation of the analyzer. The fourth operation is a skip analysis operation, the fifth is a verbose operation, the sixth is a life test and the seventh operation is a verbose operation with sub-prespotting. Each operation will be described in greater detail.

The user is instructed to enter his selection of operations by pressing one of the keys on the key pad 4 and also the "Enter" key. The analyzer will sense when a corresponding key adjacent to the displayed operation has been pressed (Block 536), as well as the "Enter" key (Block 538), will determine which key was selected (Blocks 540–552) and will perform the operation corresponding to the particular key selected (Blocks 554–566). In an alternative form, the "Enter" key need not be pressed for menu selection, the analyzer sensing when and which operation key is pressed and immediately performing the operation selected.

To facilitate an understanding of the operation of the analyzer, the following events which occur are for the normal operation of the analyzer (i.e., Block 554), as if the user pressed the key No. 1 associated with the normal operation displayed on the display.

In the "Normal Operation" routine, the analyzer will provide a display of information for the user. In its preferred form, the analyzer is particularly adapted for testing the serum of animals and for providing a diagnosis of the possible maladies of the animal being tested. The associated computer of the analyzer has stored in its memory the normal ranges for tests which are performed with respect to each category of animal. If the test results are outside of the normal ranges expected, the analyzer will alert the user to that fact and will provide the user with a possible diagnosis of the ailment. Accordingly, the analyzer will display the kind of a variety of animals (Block 568; see FIG. 37).

The user is instructed to press a particular key on the key pad for a particular animal being tested. For example, he is instructed to press the "1" key if the animal being tested is a dog, and the "2" key if the animal being tested is a cat, and so on. He is also instructed to press the "0" key for all other animals which are not displayed. The analyzer will sense when and what animal type was selected (Block 570), and the user selected information is then provided to the computer (Block 572). If the "Clear" key was pressed (Block 571) rather than making a selection, the analyzer will redisplay the main menu (Block 534).

The analyzer then provides another display (FIG. 38) in which it requests the user to enter the patient identification number. This may be a file number which is assigned to the animal by the veterinarian. In the preferred form, a patient number consisting of no more than 10 digits may be entered by the user. The analyzer will sense when the patient identification number has been entered (Block 574) and will store this information (Block 576). If the "Clear" key was pressed (Block 575) and no identification number was entered, the analyzer will redisplay the animal types (Block 568).

The analyzer, upon receiving this information, will then rotate the turntable so that receiving slot No. 0 is in alignment with the slide inserter 14 (Block 578). It should be noted that the pipette lifter was previously placed into its fully raised "home" position (Block 514).

The analyzer will then provide another display to the user (FIG. 38), instructing the user to insert the slides in the analyzer, and will inform the user how to perform this operation (Block 582). If, during the slide insertion operation, the "Clear" key is pressed (Block 583), the analyzer will eject the slides and return to displaying the main menu (Block 534).

The user inserts the slides individually into the slide inserter 14, with the notch 94 on each slide aligned with the tab 92 formed on the slide orientation plate 88. If the slides are properly aligned, the bar code 86 on the slide will be exposed through the slot 90 formed in the orientation plate.

The user then grasps the grip 80 on the inserter plate 68 and pushes forward until the inserter plate is in the most forward position. The inserter plate will push the slide 71 into an appropriate receiving slot 52 on the rotatable turntable 50 No alarm will sound, as the operation is being performed properly. One optical sensor 108, 110 associated with the slide inserter 14 will sense when the inserter plate 68 has reached its most forward position, indicating that the slide 71 has been pushed into a receiving slot 52 on the turntable (Block 584). The user then pulls back the grip 80 on the inserter plate to its most backward position, which position is sensed by the other optical sensor 102, 104 (Block 586). When the most backward position is sensed, the analyzer will cause the turntable to rotate until the next adjacent receiving slot 52 is aligned with the slide inserter 14 (Block 588). The user will then place a second slide in the slide inserter and load that slide into the next receiving slot in the same manner as before. The turntable will then rotate so that the next adjacent receiving slot is aligned with the slot inserter, and the sequence repeats itself until the desired number of slides have been inserted by the user into the rotatable turntable.

The user then indicates to the analyzer that he has completed the loading of the test slides by pressing the "Enter" key. The analyzer will sense if the "Enter" key is pressed or if all 12 receiving slots have been filled (Block 590). The slide loading operation has been completed, and the analyzer will proceed to the next step in the operation.

After the slides have been loaded, the analyzer will rotate the turntable so that test slides loaded onto the turntable will pass beneath the optical code reader 158 so that the bar code information of each test slide will be read. This information is loaded into and stored in the computer of the analyzer (Block 592). The analyzer will then "read" the slides prior to spotting and will read the white reference mark on the underside of the rotatable turntable (Block 593), as described under the heading *How the Analyzer Uses Reflected Light to Determine Concentration.*

The analyzer will display (FIG. 39), for the user's information, a chart showing the type of test slide which has been loaded into each receiving slot (Block 594). If, for example, three test slides are loaded into the analyzer, one test slide being for a calcium (CA) test another test slide being for an ammonia (NH3) test, and the third test slide being for a glucose (GLU) test, this information will be displayed in the first three boxes of the chart on the display. Since in the preferred form of the invention, there are twelve receiving slots 52, twelve boxes on the chart are displayed. The remaining boxes, which represent the unused receiving slots in this particular example, are displayed with the word "open" as no test slide had been inserted into these receiving slots.

The analyzer then informs the user that the slides have been counted, and instructs the user to insert a new disposable tip 176 on the pipette (Block 596). It also provides information to the user on its display as to how to go about putting the disposable tip on the pipette (FIG. 40). The user then signals the analyzer that this operation has been completed by pressing the Enter key.

When the analyzer senses that the Enter key has been pressed (Block 598), it will then cause the drive motor 270 of the pipette syringe metering assembly to rotate until the syringe is in its "home" position (Block 599). It is preferred to "home" the metering assembly at this stage of the operation. If the syringe homing step is performed at some other time, it is possible that any serum which the user may have accidentally left in the pipette tip may be pushed into the analyzer in an area other than on a disposable test slide. The analyzer will then also display instructions to the user to load the pipette 18 with the sample by placing the pipette tip 176 just below the fluid level of the sample and then pressing the pipette push button switch 316 to start the sample loading process (Block 600; FIG. 41). When the user presses the push button 316 on the head 318 of the pipette, this will be sensed by the analyzer (Block 602) which will then emit a tone indicating that the pipette is being loaded with serum sample. This is an indication to the user not to remove the disposable tip from below the surface of the serum sample. The analyzer will also display that the pipetting operation is underway, and that serum is being updrawn (Block 604; FIG. 42).

The analyzer will cause the drive motor 270 of the metering assembly to rotate a preselected number of turns to cause the plunger 300 of the syringe to be drawn backwardly through the syringe, which will cause serum to be aspirated into the disposable tip 176 of the pipette (Block 606).

After the proper amount of sample has been drawn into the pipette tip (which is about 10 ul per slide and about 30–40 ul to increase the pipetting accuracy), the drive motor of the metering assembly is de-energized, and the analyzer will activate the alarm 518 to emit a tone indicating that the serum sample loading operation has been completed. The analyzer will also display instructions to the user to lift the pipette tip out of the serum sample (Block 608; FIG. 43).

After a predetermined amount of time after the tone has been emitted (this time delay is provided for the user to remove the tip from the sample serum) and the user has been instructed to remove the tip from the sample serum, another tone will be emitted by the alarm 518 of the analyzer, and the analyzer will again energize the stepping motor of the metering assembly to rotate a predetermined number of steps in order to aspirate two microliters of air into the pipette tip (Block 610).

The analyzer will then provide a third tone (Block 612) and display instructions to the user to wipe the tip of the pipette and replace the pipette into the analyzer (Block 614; FIG. 44). If the user has problems with serum aspiration, he can press the "Clear" key (Block 615) and the analyzer will begin the aspiration process again at Block 596.

The user will then wipe the tip of the pipette, as instructed. The two microliters of air aspirated into the pipette tip 176 after the serum has been drawn into the pipette tip will ensure that no serum is drawn from the pipette tip by capillary action during the wiping operation. The user then places the end of the pipette through the opening 23 in the cover 12 of the analyzer and into the support ring 180 of the pipette lifter assembly. As mentioned previously, the lifter assembly has been properly positioned in its "home" position, where the pipette 18 is in its most raised position.

After the user has signaled the analyzer that he has properly placed the pipette into the pipette lifter by pressing the "Enter" key (Block 616) or automatically by sensor 175, the metering and analysis operation will now take place.

The cover 54, which had previously been placed in a position so as to cover the test slides to provide an optical background, is now rotated with respect to the turntable 50 in order to uncover the test slides so that a certain amount of sample serum may be deposited on the film portion 124 of each test slide (Block 618). Alternatively, the cover may be rotated to uncover the slides before the pipette is loaded (i.e., preferably between Block 593 and Block 594). The reason for uncovering the slides earlier in the operation is so that there is minimal delay after the filled pipette is placed in the analyzer. This allows the analyzer to start the metering operation immediately without the sample in the pipette rising in temperature appreciably. The turntable is then rotated so that each test slide 71 is sequentially positioned in alignment with the pipette tip.

More specifically, when a test slide is positioned beneath the tip 176 of the pipette, the motor 270 of the metering assembly is energized to rotate a given amount to cause the plunger 300 to move in the forward direction in the syringe 296 of the metering assembly. This forces air out of the syringe and into the disposable tip 176 of the pipette, which in turn pushes a predetermined amount of sample fluid out of the pipette tip 176. The fluid forced out of the pipette forms a drop suspended from the open end 310 of the pipette tip (Block 620). The motor 270 of the metering assembly is de-energized, and the motor 62 for the pipette lifter is then energized.

The pipette lifter lowers the pipette 18 such that the tip 176 is disposed a predetermined distance above the test slide 71 which distance is such that the drop 220 contacts the film portion 124 of the slide and is drawn by capillary action onto the film's top surface. The pipette tip is then withdrawn from the slide until the pipette reaches its home position, at which time the pipette lifter motor 62 is de-energized (Block 622). The home position of the pipette 18 is sensed by the optical sensor 218, which will signal the analyzer to rotate the turntable until the next test slide is positioned below the pipette tip (Block 624). The metering operation then repeats itself until serum has been deposited on each test slide (Block 626).

After the metering operation has been completed, about 10 ul of air is drawn up into the pipette tip (Block 628). This is done to prevent any unused serum remaining in the tip from being expelled by air in the tip above the serum sample when the air warms up, expands and exerts pressure on the sample. The cover 54 is again rotated so that it now covers each test slide (Block 628) to minimize evaporation of the deposited sample, and the analysis operation begins.

The reflectometer is energized. More specifically, depending on a particular test slide used, one or more of the LEDs will be energized depending on the test performed so that they emit and direct a light beam of a particular wavelength on the test slides (Block 630). In one form of the invention, the fluorescent lamps always remain on. Because they are separated from each other, unlike the LEDs which are grouped together, the light they emit will not interfere with that of another light source. The turntable will position the test slide over one fluorescent light source or the other, depending on the test to be performed. The reflectometry test is performed on the underside of the rotatable turntable. The cover is maintained in its covered position to prevent evaporation and to allow the reflectometry test to be performed (i.e., the reflectometer reads reflected light only, that is, color changes only on the bottom of the test slides).

The rotatable turntable continuously rotated intermittently generally in one direction (i.e., clockwise) past the reflectometer portion of the analyzer (Block 632). The turntable positions the test slides over the particular light source 422-426 corresponding to the test to be performed and energizes a particular LED of light source 426 (Block 634). It may be necessary to rotate the turntable bi-directionally during the reflectometry test. If the "leading" slide needs to be positioned over the farther fluorescent light source 422 (in terms of normal clockwise rotation of the turntable), and the next adjacent slide (in the counterclockwise direction) needs to be positioned over the other fluorescent light source 424, which it passed, the associated computer will cause the turntable to "back up" Light reflected from each test slide is detected by the photodiodes 448, 456, 468, and this information is provided to the computer of the analyzer, where such information is converted from an analog signal to a digital code and normalized to the corresponding reference signal (Block 636) and stored in memory and processed (Block 638).

If twelve receiving slots are provided on the turntable, twelve tests will be conducted simultaneously. Accordingly, the total time required to complete all twelve tests concurrently is about six or seven minutes.

Figure 45:
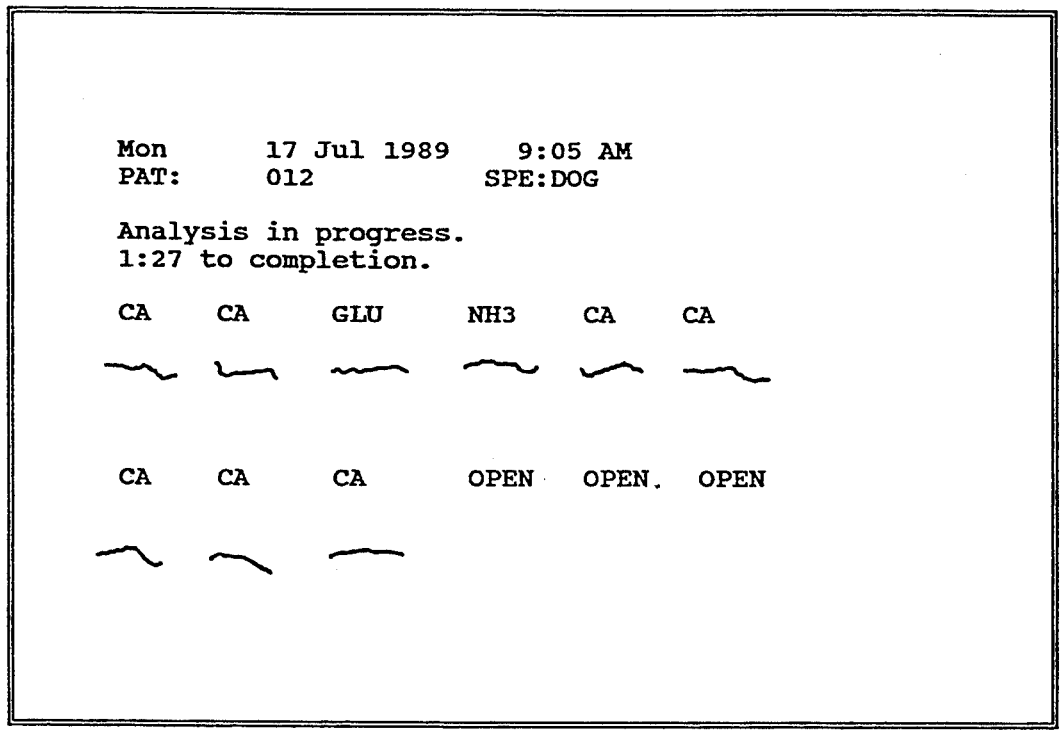
FIG. 45 is a front view of the display of the analyzer and information displayed thereon.

During the analysis operation, the analyzer will display a graph of the test results in progress (FIG. 45). If twelve test slides are being analyzed, twelve graphs will appear in two rows on the same display, so that the user may quickly and easily see the results being obtained from the test while the test is in progress. The analyzer also indicates to the user that the test is in progress, and displays the time until completion of the test (Block 640).

Figure 46:
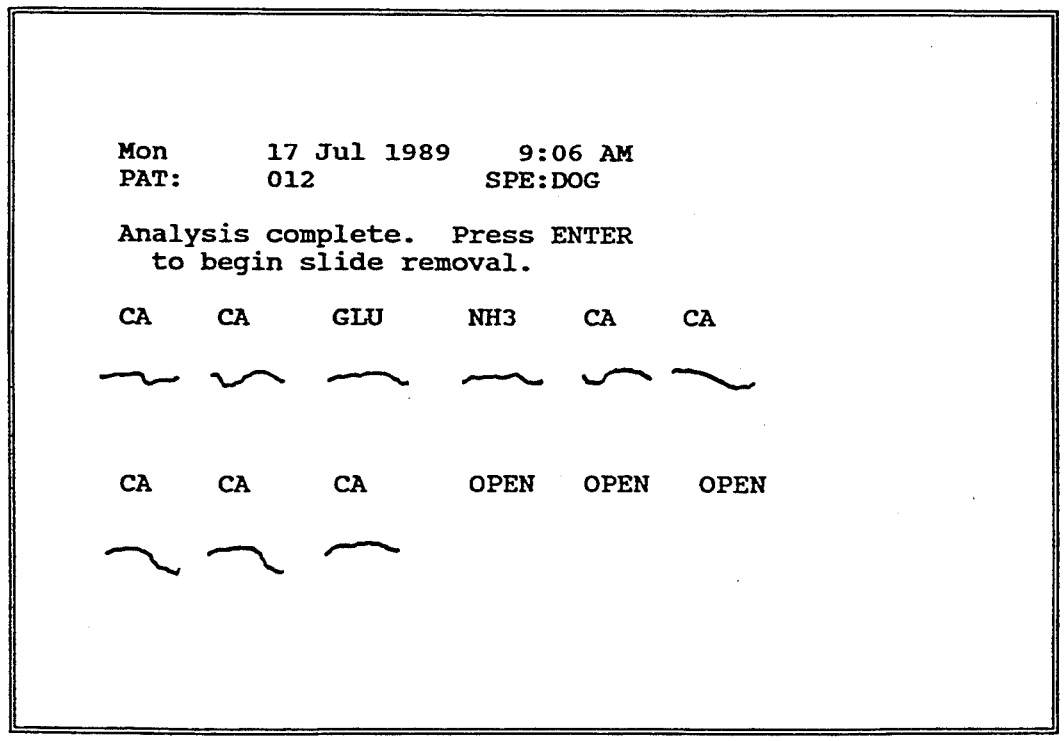
FIG. 46 is a front view of the display of the analyzer and information displayed thereon.

After a predetermined time has elapsed and the test has been completed (Block 642), the analyzer will emit a tone from the alarm 518. It will also instruct the user to press the Enter key when he wishes to begin the slide removal operation. (Block 644; FIG. 46).

After the user has instructed the analyzer to remove the slides by pressing the Enter key (Block 646) the analyzer rotates the cover 54 with respect to the turntable 50 so that the cover is now in the open position, that is, the slides are now exposed (Block 648). This will allow the ejector arm 404 to move upwardly through the receiving slots 52 to push the slides out of each receiving slot.

The turntable is then rotated intermittently so that each receiving slot is sequentially in alignment with the ejector arm 404 and with the discharge opening 410 formed in the base plate (Block 650). When a receiving slot is in proper alignment, the drive motor 398 for the ejector assembly is energized, and the ejector arm rotates upwardly through the receiving slot 52 to push the slide 71 contained in the receiving slot out of the open end of the slot and into the discharge opening 410 Block 652). The ejector arm 404 then continues to rotate to its home position, which position is sensed by the optical sensor 408 and which sensor signals the computer that the slide has been unloaded. The analyzer will then de-energize the ejector assembly drive motor 398 so that the ejector arm remains in its home position (Block 654), and will energize the drive motor 348 for the turntable so that the turntable rotates until the next adjacent receiving slot is aligned with the ejector arm 404 and discharge opening 410. The ejector assembly drive motor 398 is then energized to remove the next slide from the turntable. This sequence repeats itself until all test slides have been unloaded (Block 656).

After the slide unloading operation, the analyzer displays to the user instructions to remove and discard the pipette tip and to replace the pipette in the analyzer (Block 658; FIG. 47). The user signals the completion of this operation by pressing the Enter key (Block 660). The analyzer then displays and prints out the results of the tests, and advises the user whether the test results are outside or within the normal range for each test (Block 662; FIG. 48). If the user desires, the analyzer will provide a printout of normal ranges for the species selected.

The analyzer will also provide a profile interpretation, if the user so desires. For example, the analyzer will interpret the test data and display to the user that the results of the profile (i.e., the test results) are likely to occur in certain conditions, for example, hypoparathyroidism, dietary deficiency, age, lactation, or others (Block 664; FIG. 49). The analysis portion of the test is then complete.

Referring back to the step where the user is requested to select the operation of the analyzer (Block 536), he may select the No. 2 listing on the main menu, "Lot Number Selection". If this is selected, the analyzer will display the lot numbers for each of the test slides (Block 666; FIG. 50).

Also displayed on the main menu is a "Service Menu" routine which the user may select by pressing key No. 3 on the keyboard (Block 544). Generally, this is only needed by the analyzer service personnel.

When key No. 3 is pressed, the analyzer will display the service menu (Block 668, FIG. 51). The service menu has listed a number of service routines, including such routines as Set Clock (Block 670), Instrument Calibration (Block 672), Pipette Only Test (Block 674), Pipette Life Test (Block 676), Disk Test Menu (Block 678), Production Support Menu (Block 680), LED Control (Block 682) and Service Diagnostics (Block 684), each of the above items being identified with a particular key on the key pad which the user may press.

For example if the key corresponding to the LED control test routine is pressed (Block 686), the analyzer will display a list of the various lamps and LEDs of the reflectometer portion of the analyzer (Block 688; FIG. 52), where each lamp or LED may be turned on individually to test if it is properly functioning (Block 690).

If the user presses the key corresponding to the pipette-only test routine (Block 692) the analyzer will display instructions to the user to enter the number of spots to updraw for (Block 694; FIG. 53). The analyzer will then multiply the number entered by the user by 10 microliters and will instruct the user to put a new tip on the pipette (Block 696; FIG. 54).

After this has been done, the user will inform the analyzer by pressing the Enter key (Block 696), and the analyzer will display instructions to the user to load the pipette with the sample by placing it below the fluid level of the sample vial and to then press the push button 316 on the head of the pipette 18 (Block 700; FIG. 55). When the button is pressed (Block 702), the analyzer will emit an advisory tone and display that the pipette is being loaded (Block 704; FIG. 42), aspirate a predetermined amount of sample sufficient to conduct the test (Block 706), emit a tone and display instructions to remove the pipette from the sample vial (Block 708; FIG. 43), emit another tone and aspirate a small volume of air (Block 710) and emit a fourth tone (Block 712) and display instructions for wiping the pipette tip (Block 714; FIG. 44), in much the same manner as the analyzer did during a normal operation (see Blocks 604–614).

The analyzer will then display instructions to the user to press the pushbutton 316 on the head of the pipette every time a sample is to be discharged from the pipette tip (Block 716; FIG. 56). In this way, service personnel may determine whether the proper amount of serum sample is being discharged. The analyzer will sense when the pushbutton is pressed (Block 718), and will meter out 10 $\mu l$ of sample (Block 720). It will then count the number of times the push button has been pressed, and when this number equals the number entered originally in this test procedure (Block 722), an alarm will be triggered alerting the user that the test has been completed (Block 724).

For the Set Clock service routine (Block 670), the service personnel depresses the key No. 1 (Block 726). The analyzer will then display a second menu (Block 728; FIG. 57), showing the current date and time and requesting whether the user wishes to change the day of the month, the month, year, hours and minutes by an appropriate selection of a key on the key pad (Block 730).

Returning again to the service menu, if key No. 8 on the key pad is pressed (Block 732), which key corresponds to the service diagnostics operation of the analyzer (Block 684), the analyzer will display a service diagnostics menu (Block 734; FIG. 58), which includes such items as cycle articulated pipette; turn ultra-violet bulbs on; turn ultra-violet bulbs off; view/modify EE prom; dump instrument cal; initialize EE prom and set serial number. Any one of these operations may be selected by the user by his depressing the corresponding key pad number and the analyzer will perform the selected operation (Block 736).

More specifically, the "cycle articulated pipette" routine will continuously cycle the pipette lifter mechanism and display how long each cycle takes; and the "view/modify EE prom" routine will display the contents of an EE prom (which is part of the analyzer's computer memory). The EE prom contains such information as the serial no. of the analyzer, the analyzer settings and calibration data. The contents of the prom are displayable, and the service personnel may view and change the contents.

The "dump instrumentcal" routine will cause the analyzer to display the calibration data. The "initialize EE prom and set serial no." routine will allow the prom to be set up or pre-programmed with initial calibration data and a serial no. This routine is envisioned to be used at the analyzer manufacturing facility.

If the pipette life test routine (Block 676) is chosen by the user pressing key No. 4 (Block 738), the analyzer will instruct the user to mark the current position of the pipette and press any key to begin (Block 740 742; FIG. 59) and to press another key when the user wishes to end the routine (Block 744, 746, FIG. 60). This routine will test the sample metering mechanism of the analyzer, and will cause the metering drive motor 270 to be energized between key presses (Block 744).

If key No. 5 is pressed (Block 748), the analyzer will go into a disk (i.e., turntable) test routine (Block 678) in which a disk test menu will be displayed (Block 750; FIG. 61). Under this routine, the following diagnostic tests regarding the cover and turntable may be performed: set the rotatable turntable "home" position; rotate the turntable continuously in a clockwise direction; rotate the turntable continuously in a counter-clockwise rotation; a disk life test; open the cover; close the cover; operate the ejector assembly at the current location of the turntable; and move the slide turntable a predetermined number of steps. The analyzer will perform any one of these steps when the user presses a corresponding key on the key pad (Block 752).

Returning now to the service menu, the user may select the production support menu and routine (Block 680) by pressing key No. 6 (Block 754). The analyzer will display another production diagnostics menu (Block 756; FIG. 62) in which the user may select one of the following diagnostic operations: read the A/D channels; load slides; R.D. test; eject all slides; table home sense change; key pad change; and cover home sense change. Any one of these operations will be performed by the analyzer when the user presses an appropriate key (Block 758).

Again returning to the service menu when key No. 2 is pressed (Block 760), an instrument calibration routine will be performed (Block 672). The user, through this routine, may calibrate the analyzer and in particular the reflectometer portion of the analyzer. The analyzer will display an instrument calibration menu (Block 762; FIG. 63) in which the user is instructed to press a particular key to perform the following functions: read visible white slides; read visible black slides; read ultra-violet white slides; read ultra-violet black slides; enter visible reflectances; enter ultra-violet reflectances; calculate black and white references; and save references and return. In this routine, the user is instructed to insert a number of reference slides in the turntable, which reference slides are read by the ultra-violet light sources and the LED light sources in order to calibrate such light sources (Block 764).

If the user presses key No. 9 (Block 765) on the service menu, the analyzer will display the main menu. If key No. 3 was pressed before the main menu was displayed (see Block 767), the analyzer will test the mechanical and electrical functions and continue its operation starting at Block 512.

Returning again to the main menu displayed by the analyzer (Block 534; FIG. 36), the user may select the routine ,. "skip analysis operation" (Block 560) by pressing key No. 4 on the key pad (Block 546). The analyzer will perform the steps in the normal operation routine (Blocks 568–626 and 648–656), except that it will not perform the steps associated with the actual analysis of the test slides (Blocks 628–646 and 658–664). The performance of this routine is shogun in the flow chart of FIG. 32 generally by Block 766.

If, on the main menu, the user selects the verbose operation routine (Block 562) by pressing key No. 5 (Block 546), the analyzer will step through the same steps of the normal routine described previously (Blocks 568–664), except that the user is allowed to override bar codes, save the analysis data on a floppy disk, and print out the data readings of each slide. The performance of this routine is shown in the flow chart of FIG. 32 generally by Block 768.

The user may also select a "life test" (Block 554) by pressing key No 6 (Block 550). The life test is the same as the normal routine but it simulates all user interaction and runs tests over and over until either the analyzer is turned off or a failure occurs. The performance of the life test routine is shown in the flow chart generally by Block 770.

A "verbose with sub-prespot test" (Block 566) may be performed by the user by pressing key No. 7 (Block 552) on the main menu. This test is the same as the verbose test (Block 562), but also subtracts the pre-spot slide readings (i.e., before the serum is spotted) from all of the slide readings. The performance of this routine is shown generally by Block 772 in FIG. 32.

THE ELECTRONIC CIRCUITRY OF THE CHEMICAL ANALYZER

FIGS. 64–68 show schematically and in block diagram form the associated electronic and computer circuitry of the blood analyzer of the present invention. The actual values and part numbers of the components used in the electronic circuitry shown in FIGS. 64–68 are for illustrative purposes only, and to facilitate an understanding of the invention. However, alternative components and values for these components may be substituted by one skilled in the art to provide the same or similar results.

Figure 64A:
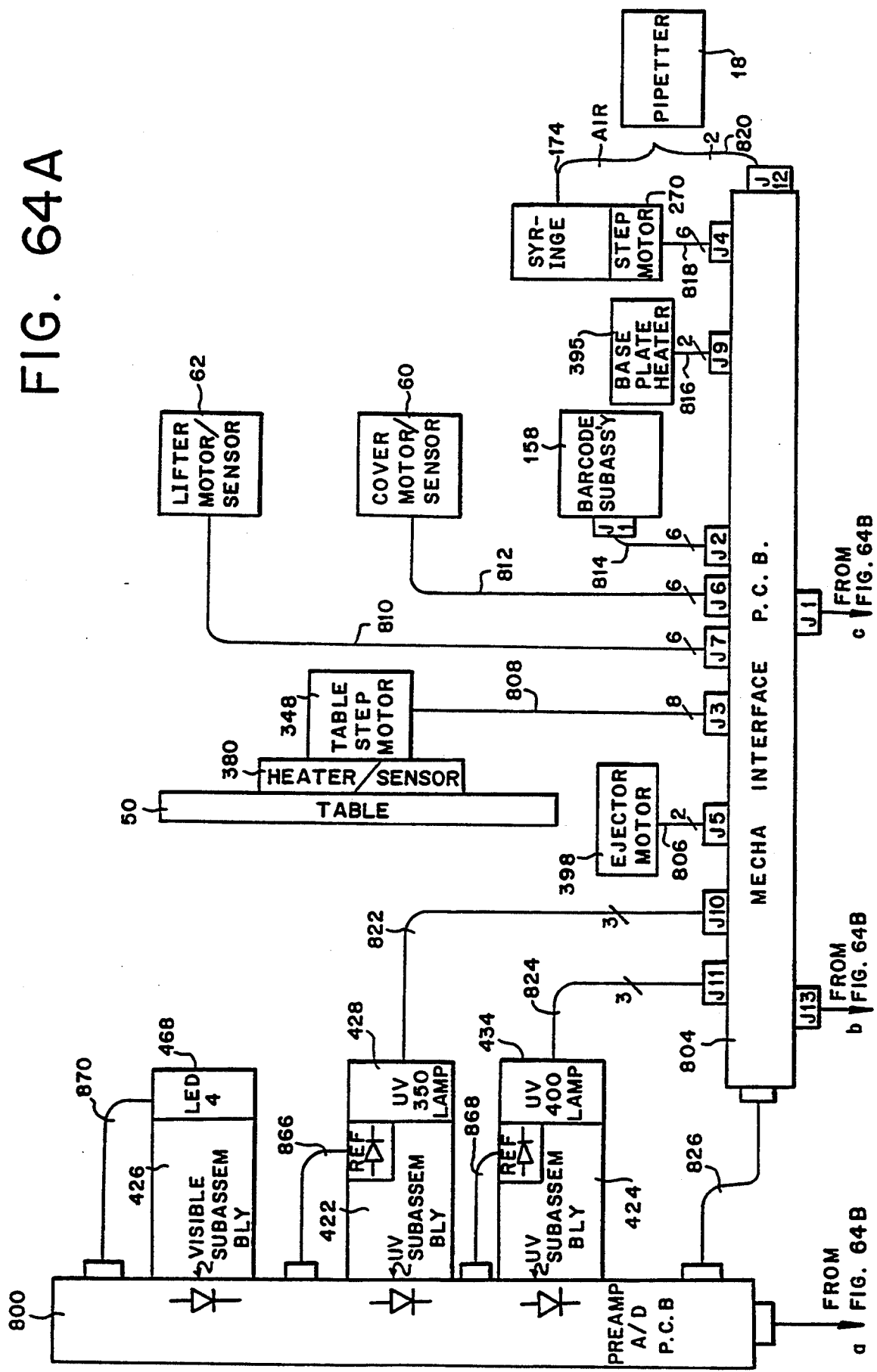

Initially referring to FIG. 64 of the drawings, a block diagram of the subassemblies and major components of the electronic circuitry of the blood analyzer is shown.

There are three major subassemblies used in the preferred form of the blood analyzer: a preamplifier and analog-to-digital subassembly 800 (shown in detail in FIG. 65); a computer interface subassembly 802 (shown in detail in FIG. 66); and a mechanical interface subassembly 804 (shown in detail in FIG. 67).

As shown in FIG. 64 the mechanical interface subassembly 804, as its name implies, serves to interface between the computer interface subassembly 802 and the various drive motors and "home" position optical sensors which are associated with the rotatable turntable 50, the cover 54 and other mechanical components of the blood analyzer.

More specifically, the mechanical interface subassembly 804 is connected by a bus line 806 to the ejector motor 398 which is used for removing slides from the turntable after the analysis operation has been completed. The interface subassembly 804 is also connected to the turntable stepping motor 348, the heater 380 for the turntable and the sensor 378 which is used in controlling the temperature of the turntable, through a bus line 808.

The interface subassembly 804 is also connected to the pipette lifter motor 62 and its associated optical sensor 218 by a bus line 810; the cover drive motor 60 and its associated position sensor 168 through a bus line 812; and the bar code subassembly 158 (shown in greater detail in FIG. 68) which optically scans the bar codes 86 on the top surface of each test slide 71 as they pass below the bridge bracket 58. This subassembly is connected by a bus line 814 to the interface subassembly 804.

Also connected to the mechanical interface subassembly by a bus line 816 is the base plate heater 395, which maintains the temperature of the base plate 48; the DC stepping drive motor 270 for the syringe metering assembly, by a bus line 818; and the pipette assembly, and in particular, the push button switch 316 located at the head of the pipette, by a two conductor bus line 820.

The mechanical interface subassembly 804 is also connected to the two ultraviolet lamps 428, 434 by appropriate bus lines 822, 824, to turn on the ultraviolet lamps under the appropriate conditions; the preamplifier and analog-to-digital subassembly 800 by an appropriate bus line 826; the computer interface subassembly 802 by appropriate bus lines 828; and to the power supply 830 by multiple lines 832.

As shown in FIG. 64, the power plug 834 is connected to the power jack 32, which plugs into the male connector 30 on the back of the analyzer (see FIG. 2). The male connector 30 is connected to the power switch 28 by appropriate lines 836 which power switch is in turn connected by lines to a conventional power supply 830, such as Part No. SR-10A manufactured by Sanyo Corporation. The power supply provides +5 volts and ±12 volts to the associated circuitry of the blood analyzer.

More specifically, the power supply 830 provides power to a fan 838 mounted in the base portion of the analyzer by appropriate lines 840, which fan may be Part No. 6005 L manufactured by Sanwa Corporation; connected by appropriate lines 832 to the mechanical interface subassembly 804; and connected by lines 842 to a printer subassembly 844 and its associated printer 846. The printer 846 is Part No. STP201 manufactured by Seiko Company, and the printer subassembly 844, which interfaces with and drives the printer, is also manufactured by Seiko Company, and may be purchased from Seiko Company when purchasing the Seiko printer.

The power supply 830 is also connected by appropriate lines 848 to the floppy disk drive assembly 36, which may be Part No. FD235HF manufactured by Teac Company, and to the computer 850 of the blood analyzer by multiple power lines 852.

The computer 850 used in the blood analyzer preferably has a 256K memory, and may be Part No. SPC400A manufactured by Sanyo Corporation. The computer 850 is connected to the computer interface subassembly 802 (shown schematically in FIG. 66 of the drawings). The computer 850 is programmed in accordance with the flow chart described previously (see FIG. 32) and the program attached as an appendix.

The computer 850 is also connected to and drives a speaker 518 by appropriate lines 852, which speaker produces at least two tones, one to signal the user that a step has been completed, such as the aspiration of sample liquid into the pipette tip 176, and another tone to indicate that the slide inserter 14 is not in its home position.

As also shown in FIG. 64 of the drawings, the computer interface subassembly 802 is connected by appropriate bus lines 854 to the preamplifier and analog-to-digital converter subassembly 800; to the mechanical interface subassembly 804 by appropriate bus lines 856; also to the printer subassembly 844 by appropriate bus lines 828; to the display 8 of the analyzer by appropriate bus lines 858, which display is preferably a liquid crystal display (LCD) and may be Part No. LCM556 manufactured by Sanyo Corporation; and to a keyboard subassembly 860 by appropriate bus lines 862.

The keyboard subassembly 860 is basically an interconnect printed circuit board with a series of wires and which is mounted on the back of the keyboard 4, and is connected to the keyboard by a bus line 864. The keyboard subassembly 860 also includes a light emitting diode (LED) which is employed as a power on indicator 6. The keyboard 4 is basically a matrix, membrane type keyboard, and is illustrated pictorially in FIG. 1.

FIG. 64 also shows in simplified form the reflectometer portion of the blood analyzer. There are, basically, three subassemblies associated with the reflectometer. The first subassembly 426 produces a visible light spectrum. It incorporates four LEDs 462, as described previously, the light from each of which is shone on and reflected from the test slide 71 which reflected light passes through a lens 466 and onto a photodiode 468. It should be noted that a reference for the light emitted by the LEDs 462 is included in the present invention, this reference being in the form of a light colored glass (not shown) mounted on the underside of the turntable 50. Because LEDs do not drift in wavelength or intensity as much as ultraviolet lamps do, the analyzer does not need a constantly monitoring reference photodiode as is needed with the ultraviolet lamps 428, 434. During a calibration step, the analyzer will rotate the turntable 50 until the LED reference glass is aligned with the optical lens 466 of the LED optical subassembly 426 so that light from the LEDs will be reflected from the reference glass and be detected by the photodiode 468.

One ultraviolet lamp subassembly 422 includes a 350 nM lamp 428, a reference photodiode 457 which may be mounted partially in or over the bore of the block and at least positioned to receive light emitted by lamp 428, an optical lens 442, an optical stop 447 which has a single aperture through its thickness, a filter 431 interposed between the lens and the optical stop, and a sensing photodiode 448 mounted on the pre-amplifier and analog-to-digital converter printed circuit board 420.

The second ultraviolet lamp subassembly 424 similarly includes a 400 nM ultraviolet lamp 434, a lens 450, optical stop 449, filter 440, a reference photodiode 459 mounted in the block 436 in the same manner as reference diode 457 and a sensor photodiode 456, which sensor photodiode is mounted on the pre-amplifier and analog-to-digital converter subassembly board 420.

Because the reference photodiodes 457, 459 for the ultraviolet lamps are positioned near the opening in the mounting blocks 430, 436 of the ultraviolet lamps and not on the pre-amplifier printed circuit board 420, they are connected to the board by appropriate wires 866, 868. Similarly, the LEDs 468 of the visible light subassembly are connected by appropriate wires 870 to the pre-amplifier board 420.

Figure 65A:
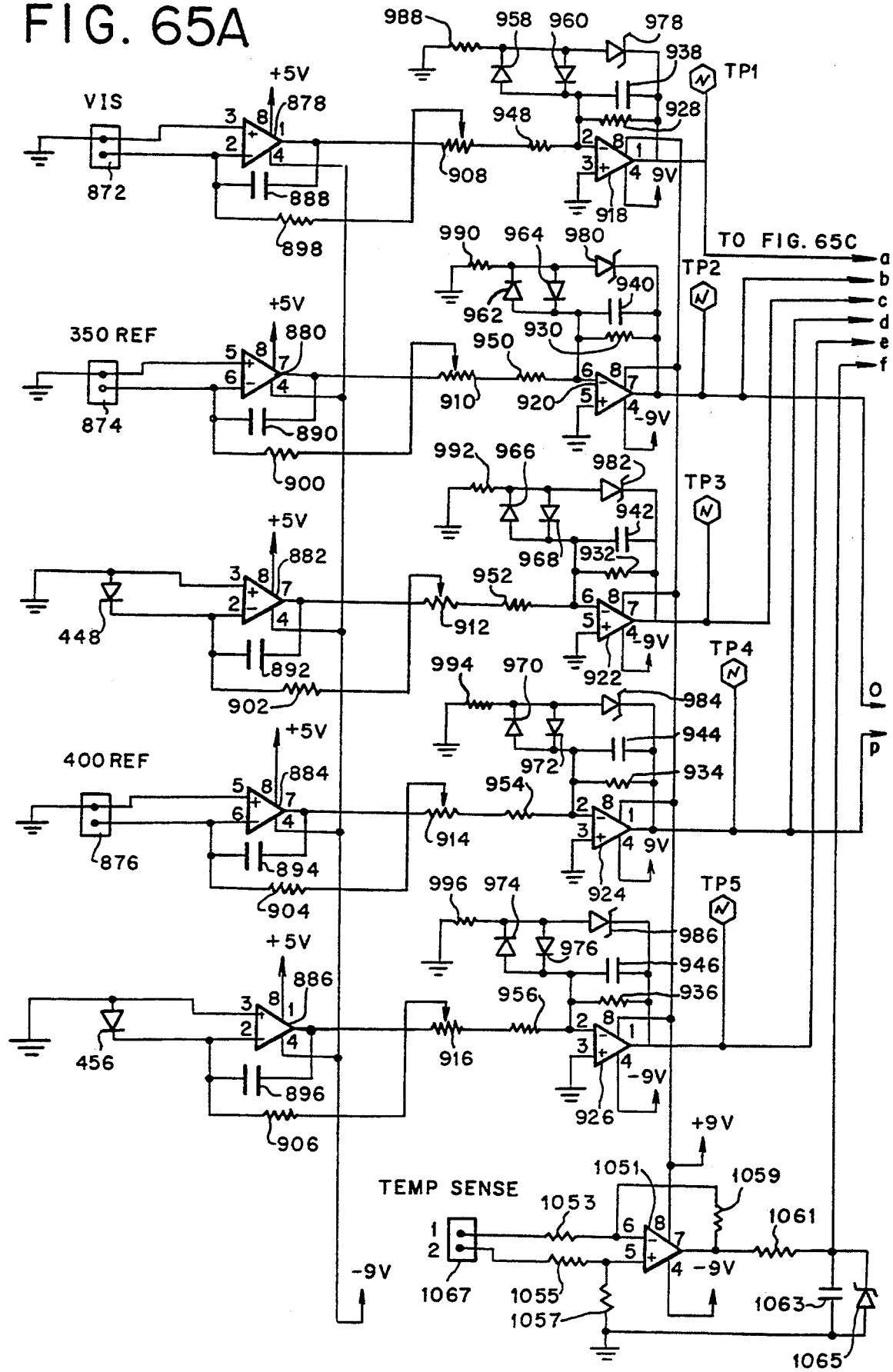
FIG. 65A-C is a schematic diagram of a first portion of the electronic circuitry of the analyzer.
Figure 65B:
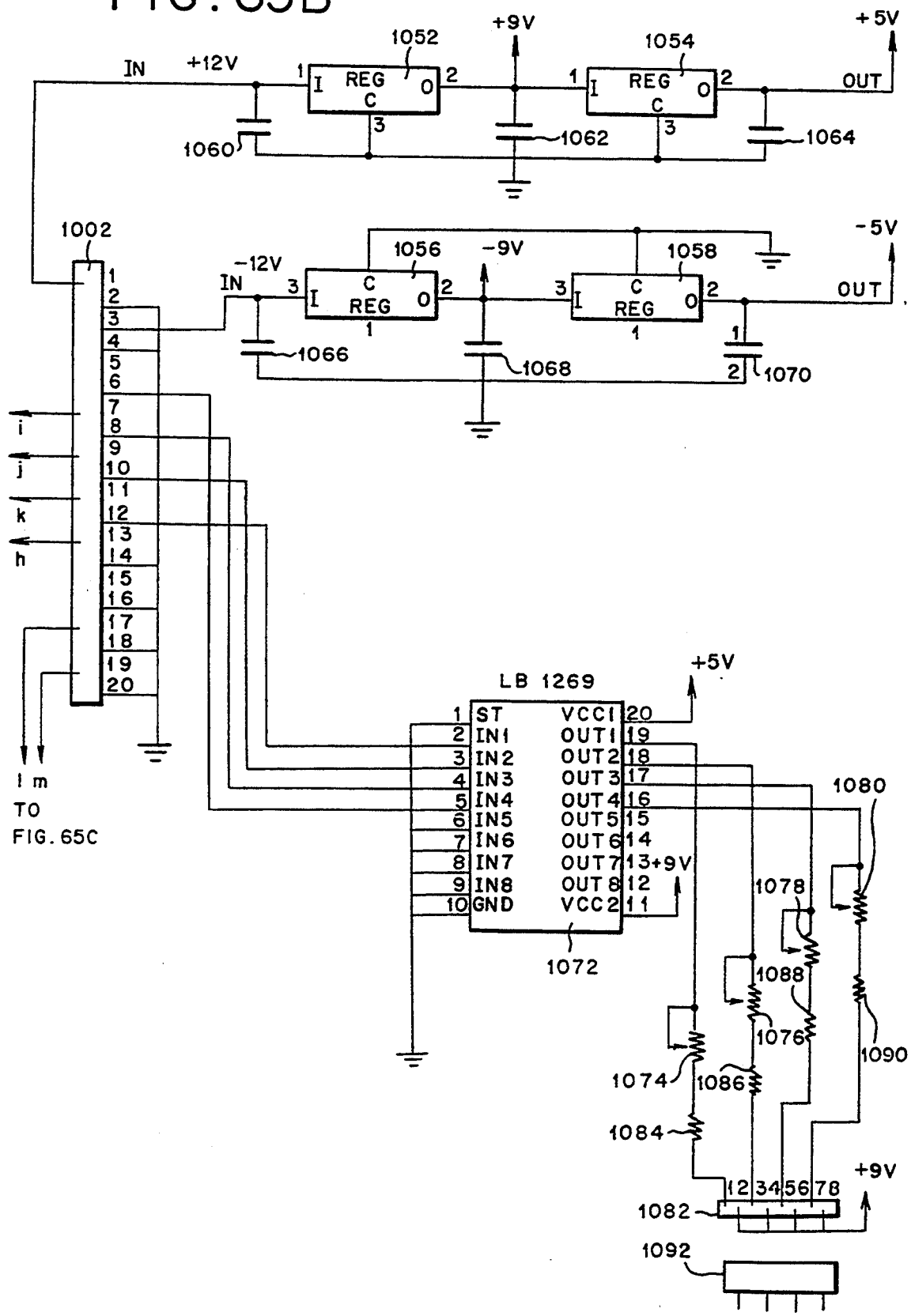
Figure 65C:
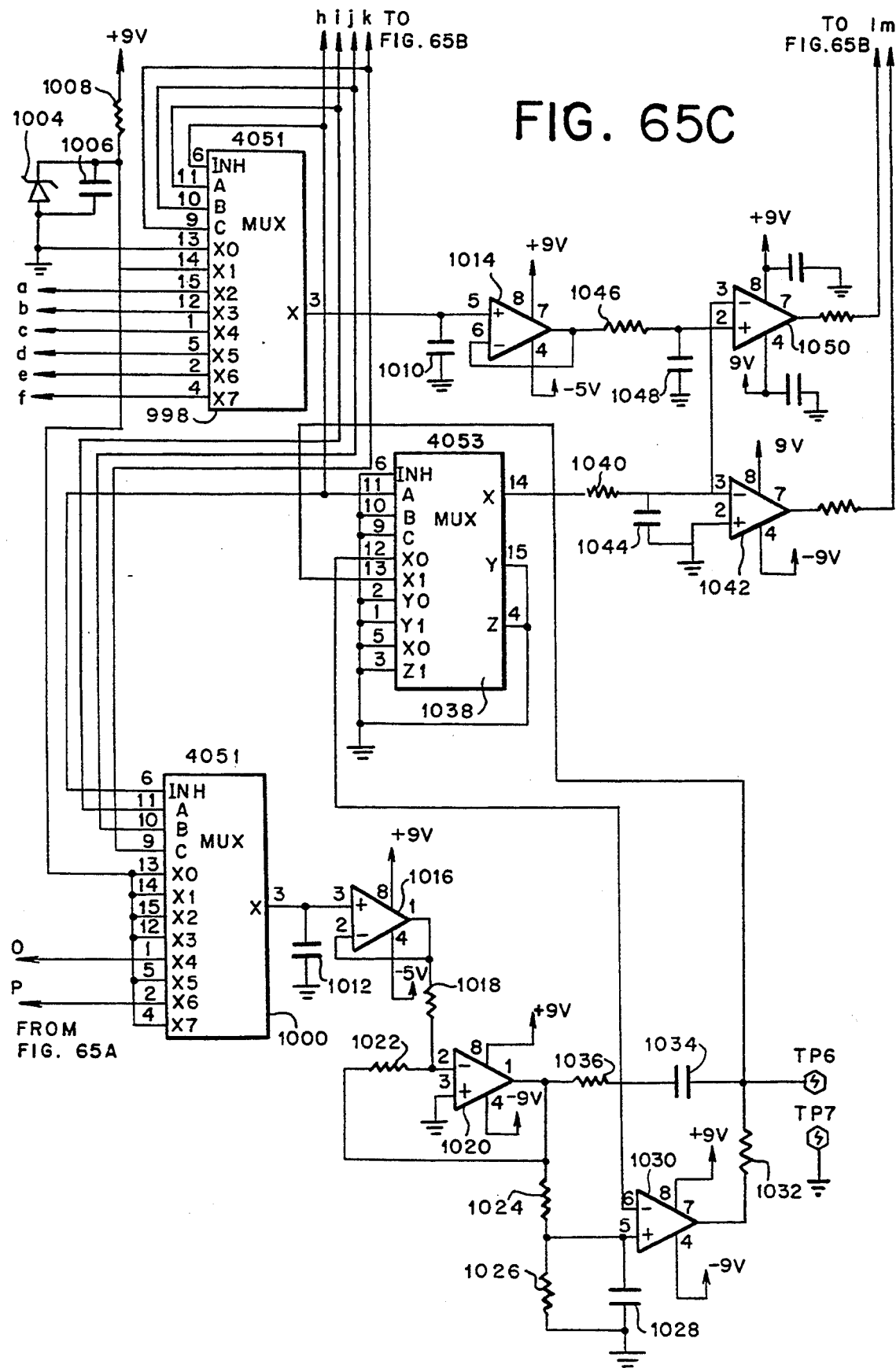

FIG. 65 illustrates the preferred form of the pre-amplifier and analog-to-digital converter subassembly 800 of the blood analyzer.

Three 2-input connectors 872-876 are used to connect the photodiodes 457, 459 468 which are not mounted on the printed, circuit board 420 of the subassembly to the rest of the circuitry on the printed circuit board. One input of each connector is grounded, and the other input is connected to one of the sensing photodiodes 468 for the visible spectrum (i.e., the LED source 426), the reference diode 457 for the 340 nm ultraviolet light source, and the reference diode 459 for the 400 ultraviolet light source. The other side of these photodiodes are connected to ground.

In addition, the two sensing photodiodes 448, 456 for the ultraviolet light sources are mounted on the printed circuit board 420, and have their anodes connected to ground.

Each of the photodiodes either reference diodes or sensing diodes are connected to trans-impedance amplifiers. Each of the trans-impedance amplifiers includes an operational amplifier 878-886, with the non-inverting (+) input connected to ground and the inverting (−) input connected to a corresponding photodiode 468, 457, 448, 459, 456. Each amplifier includes a feedback capacitor 888-896 and a feedback resistor 898-906 connected in parallel. The trans-impedance amplifiers are basically used to convert the current which changes in the photodiodes to a variable voltage, which voltage changes in proportion to the amount of light impinging on the photodiodes.

The output of each trans-impedance amplifier is connected to one end and the wiper arm of a potentiometer 908-916. The potentiometers are used as gain controls to normalize the various photodiode "channels". The third leg of each potentiometer 908-916 is connected to a second amplifier stage consisting of an operational amplifier 918-926 and its associated feedback components, i.e., resistors 928-936 and parallelly connected capacitors 938-946.

The second stage of amplifiers is provided for several purposes. First, in conjunction with the gain adjust control potentiometers 908-916, the amplifiers normalize each of the photodiode "channels" so that the signals presented to the analog-to-digital converter circuitry, which will be explained in greater detail, are each of the same proportion.

Second, it provides a second stage of gain for each of the signals from the photodiodes, through the feedback resistors 928-936 the gain potentiometers 908-916, and input resistors 948-956 connected to the inverting inputs of each of the operational amplifiers 918-926.

Third, each of the second amplifier stages also acts as a clipper circuit through the use of a parallel arrangement of reversed polarity diodes 958-976, zener diodes 978-986 and resistors 988-996 to ground, all of which are connected in the feedback loops of the amplifiers 918-926. This will limit the output voltage of the operational amplifiers which voltage is provided to a next stage of multiplexers to prevent damaging the multiplexers by providing them with signals that are above the absolute maximum voltages specified by the manufacturer of the multiplexers.

The output signals of the second amplifier stages are provided to the inputs of a pair of multiplexers 998, 1000. More specifically, the amplifier stages which amplified the signals from the sensor photodiodes 468, 448, 456 are provided to the first multiplexer 998, and the amplifier stages which amplify the signals from the reference photodiodes 457, 459 are connected to the inputs of the second multiplexer 1000. The channel selecting inputs A-C of the multiplexers are connected to the computer 850 of the analyzer through an output connector 1002 on the pre-amplifier subassembly. Accordingly, the computer 850 will provide the needed code to make the selection as to which of the sensor photodiode signals and reference diode signals are to pass through the multiplexers 998, 1000.

A zener diode 1004 connected in parallel with a capacitor 1006, and being further connected between ground and to a positive voltage through a resistor 1008, is also connected to the second multiplexer 1000. The zener diode circuit provides a 5 volt reference signal which will be used when the photodiode sensing signal corresponding the LED visible light assembly 426 is used.

Connected to the output of each multiplexer 998, 1000 is a capacitor 1010, 1012 to ground, and each capacitor is connected to the non-inverting input of an operational amplifier 1014, 1016, which amplifier acts essentially as a buffer with unity gain. The combination of the capacitor 1010, 1012 with its associated buffer amplifier 1014, 1016 acts as a sample-and-hold circuit so that the output of the amplifiers will correspond to outputs of the multiplexers 998, 1000, but held for the time required to do an analog-to-digital conversion of the signals.

After capacitors 1010, 1012 have charged up to the voltage level of the signals, which have passed through the multiplexers 998, 1000, the multiplexers are inhibited by a signal from the computer 850 provided to the inhibit (INH) inputs so that the output of each multiplexer will appear as an open circuit, which will prevent the sample-and-hold capacitors from discharging.

Because the reflected light multiplexer 998 and the reference multiplexer 1000 are controlled by the computer to allow the respected signals to pass through simultaneously, it is ensured that the reflected light signals and their associated reference signals are received at the same time to charge their respective sample-and-hold capacitors 1010, 1012. This particular configuration will reject noise generated by the ultraviolet lamps 428, 434 by as much as 30 dB.

It should also be noted at this point that the computer 850 will use the multiplexers 998, 1000 when conducting a self test or in order to calibrate the analyzer; in other words, it will control the multiplexers to allow the reference signals to pass through to check what the levels of these signals are and if they have changed from the last calibration.

The output of the buffer amplifier of the reference signal sample-and-hold circuit 1016 is coupled through a input resistor 1018 to the inverting input of an operational amplifier 1020, having a feedback resistor 1022. The operational amplifier 1020 is configured to provide a gain of −1, that is, it merely inverts the signal provided by the reference signal sample-and-hold circuit 1016.

The output of the inverting amplifier 1020 is provided to a resistor divider network comprising resistor 1024 in series with resistor 1026. Resistors 1024 and 1026 are chosen so that the midpoint connection of the two resistors provides a voltage which is equal to −1/5th of the reference signal. Capacitor 1028 is connected across resistor 1026 and the signal at the midpoint connection of resistors 1024 and 1026 is provided to the non-inverting input of an operational amplifier 1030. The operational amplifier 1030 has its output connected to a resistor 1032 which is connected to one side of a capacitor 1034. The other side of the capacitor 1034 is connected to a resistor 1036, whose other side is connected to the output of the inverting operational amplifier 1020, and capacitor 1034 and resistor 1036 are together connected to the inverting input of operational amplifier 1030.

Another multiplexer 1038 is provided in the pre-amplifier and an analog-to-digital converter subassembly 800. The multiplexer 1038 has one of its select lines (input A) connected to the inhibit inputs (INH) of the reflected light signal multiplexer 998 and reference signal multiplexer 1000. Multiplexer 1038 is basically a quad 2-input multiplexer.

One of the inputs (X0) of one pair of inputs (X0, X1) is connected between resistor 1036 and capacitor 1034. The other input (X1) is connected to the output (X) of the multiplexer associated with that pair of inputs. The output (X) is also connected to the other side of capacitor 1034.

When the computer 850 signals to enable multiplexers 998 and 1000, it will also signal multiplexer 1038 to choose the X0-X path, which will effectively short out capacitor 1034. However, a side of capacitor 1034 connected to resistor 1032 will be at −0.2 of the reference signal voltage. Accordingly, capacitor 1034 will charge from this negative voltage level when released by multiplexer 1038.

When the computer sends an opposite signal to the inhibit inputs (INH) of multiplexers 998 and 1000, and to the "A" input of multiplexer 1038, the path between input (X1) and output (X) through the multiplexer is chosen. Capacitor 1034 will now charge positively from the −0.2 reference signal starting point at a constant slope, as current is provided through resistor 1036 to capacitor 1034.

The output (X) of multiplexer 1038 is connected through a series resistor 1040 to the inverting input of a comparator 1042. The non-inverting input of comparator 1042 is connected to ground, and a capacitor 1044 is connected between ground and resistor 1040.

Comparator 1042 is a zero-level comparator. That is, it will compare the rising voltage on charging capacitor 1034 with ground. When the voltage on capacitor 1034 rises above ground, the output of the comparator 1042 will switch states and provide a signal to the computer 850. The signal will be used to start a timer which will be used to determine the voltage of the reflected light signal, as will be explained in greater detail.

The output of the sample-and-hold circuit 1014 for the reflected light signal is connected through a low-pass filter comprising resistor 1046 connected to capacitor 1048 to the non-inverting input of a comparator 1050. The inverting input of comparator 1050 is connected to the inverting input of comparator 1042 so that both comparators 1050 and 1042 receive the same charging signal from capacitor 1034. When the charging signal rises to a level of the reflected light signal on the non-inverting input of comparator 1050, the output of the comparator will switch state and signal the computer that the capacitor 1034 has charged up to the same voltage, or substantially the same voltage, as the reflected light signal.

Figure 66A:
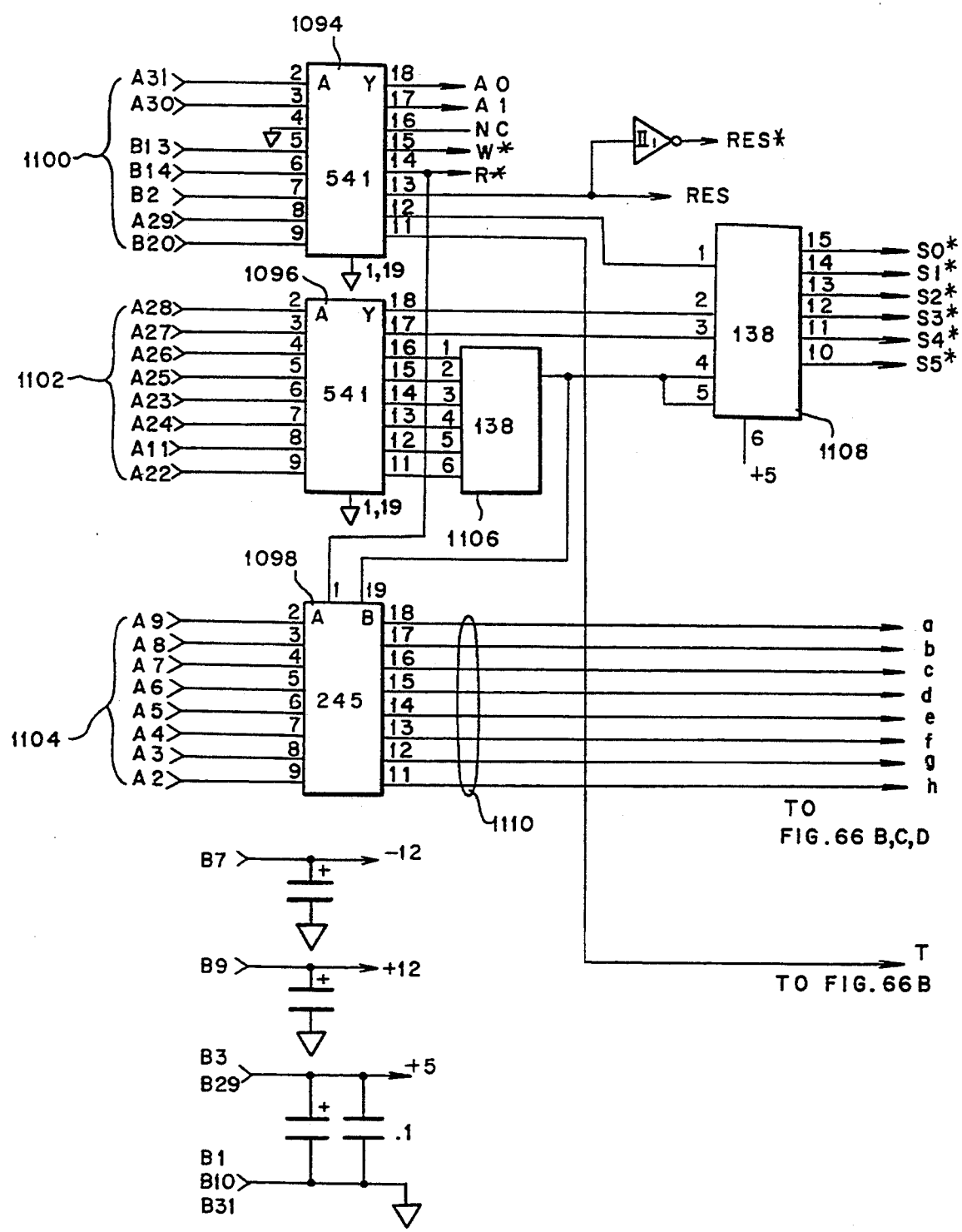
Figure 66C:
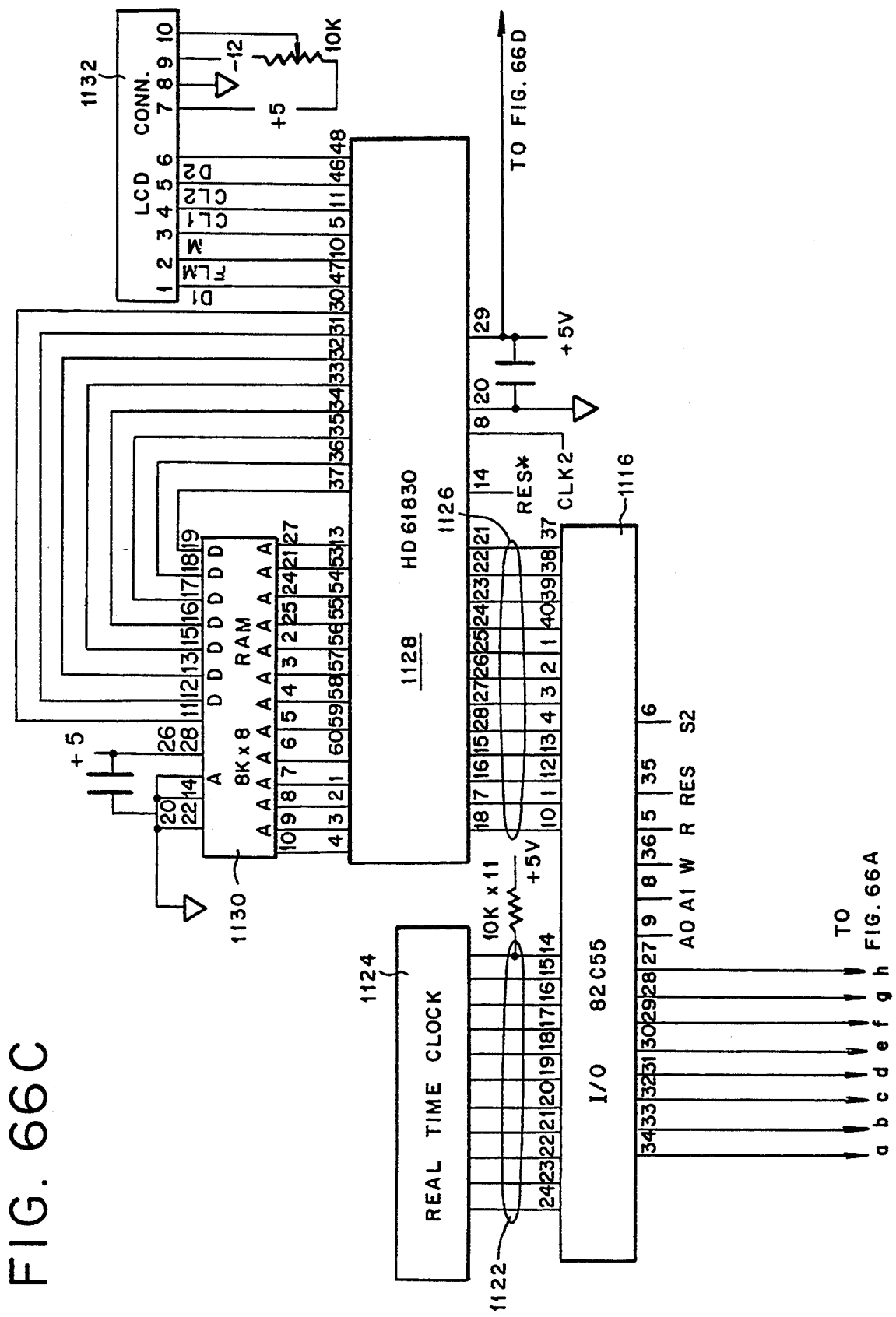
Figure 66D:
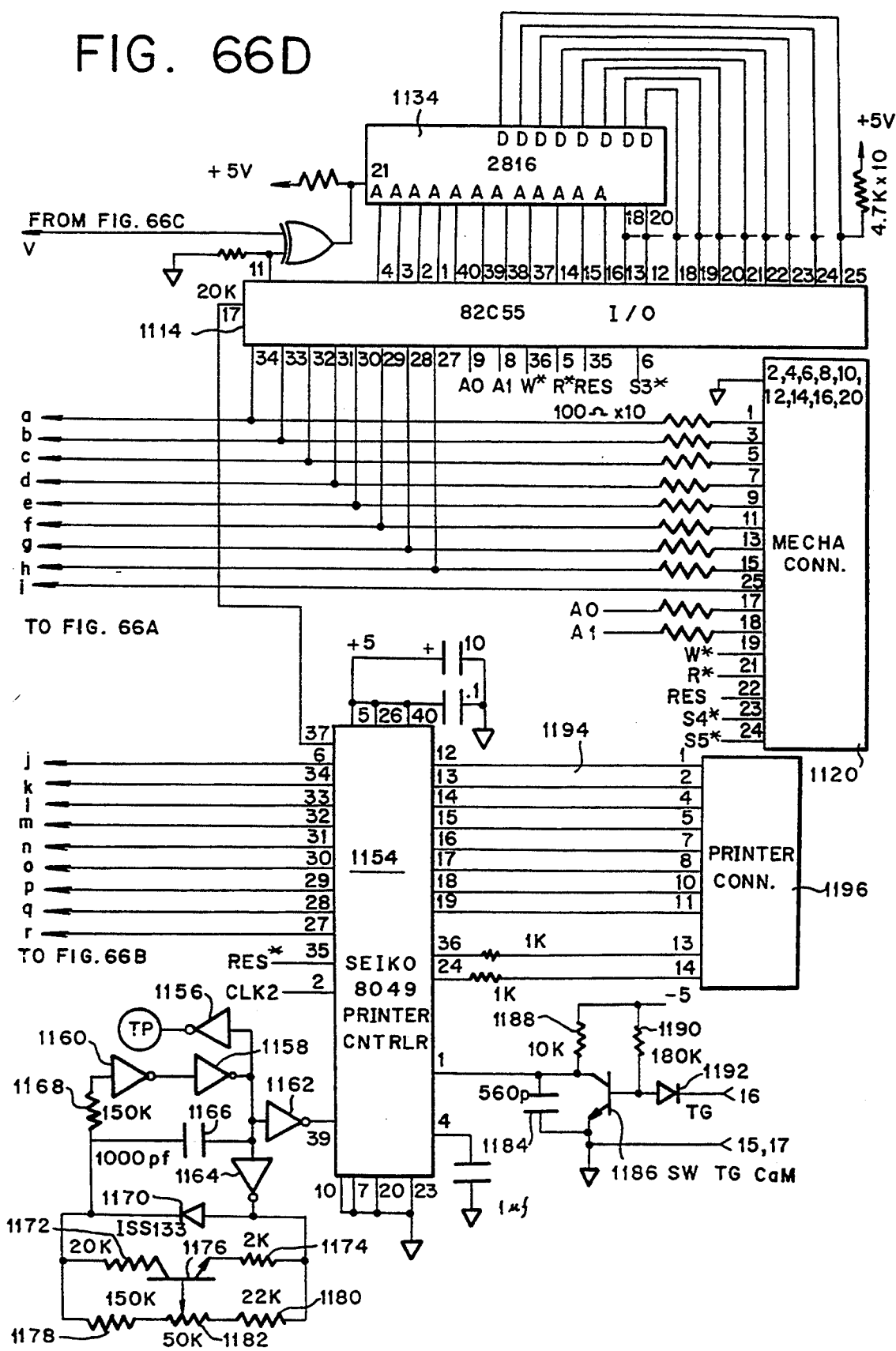
Figure 67A:
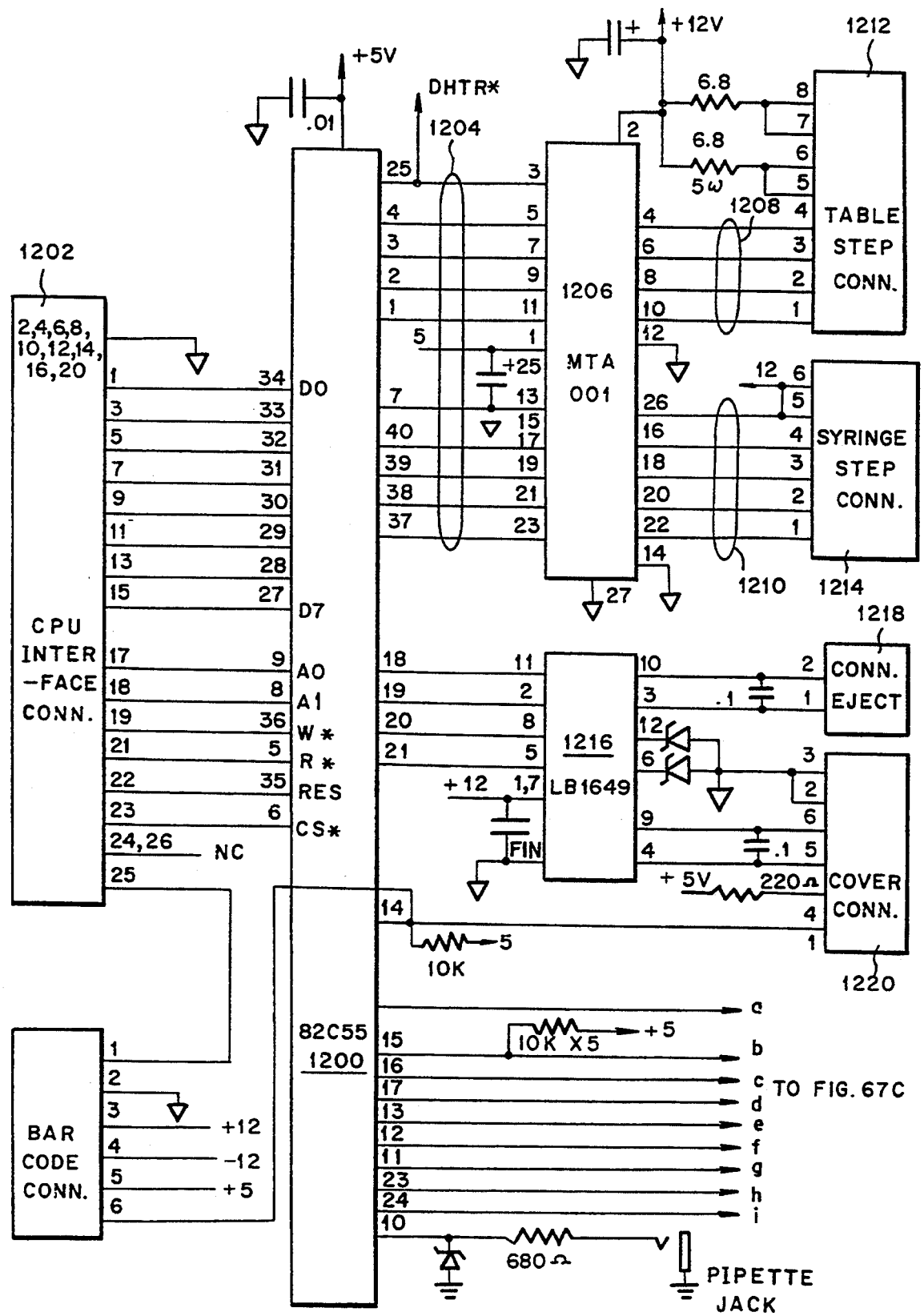
FIG. 67A-D is a schematic diagram of a third portion of the electronic circuitry of the analyzer.
Figure 67B:
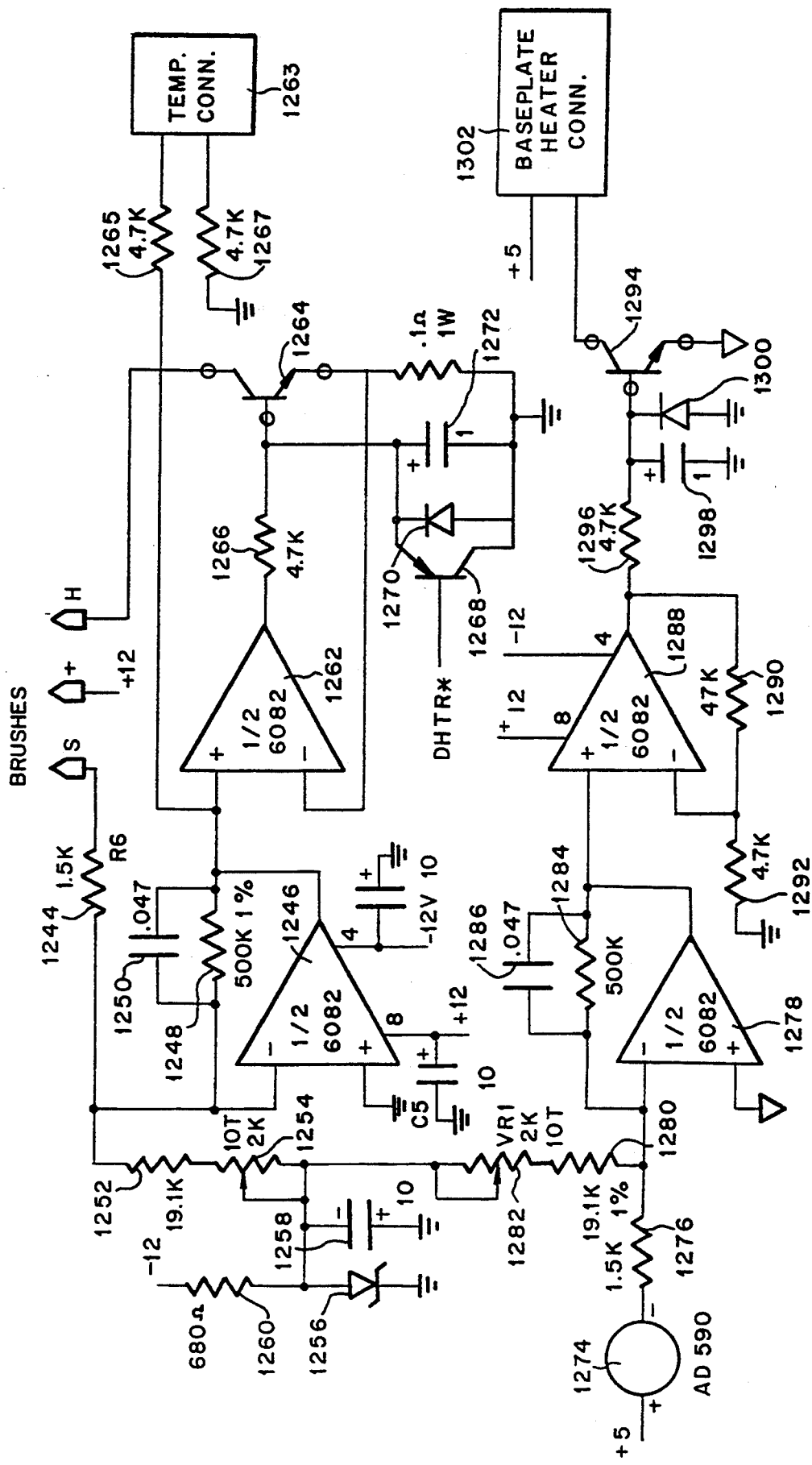
Figure 67C:
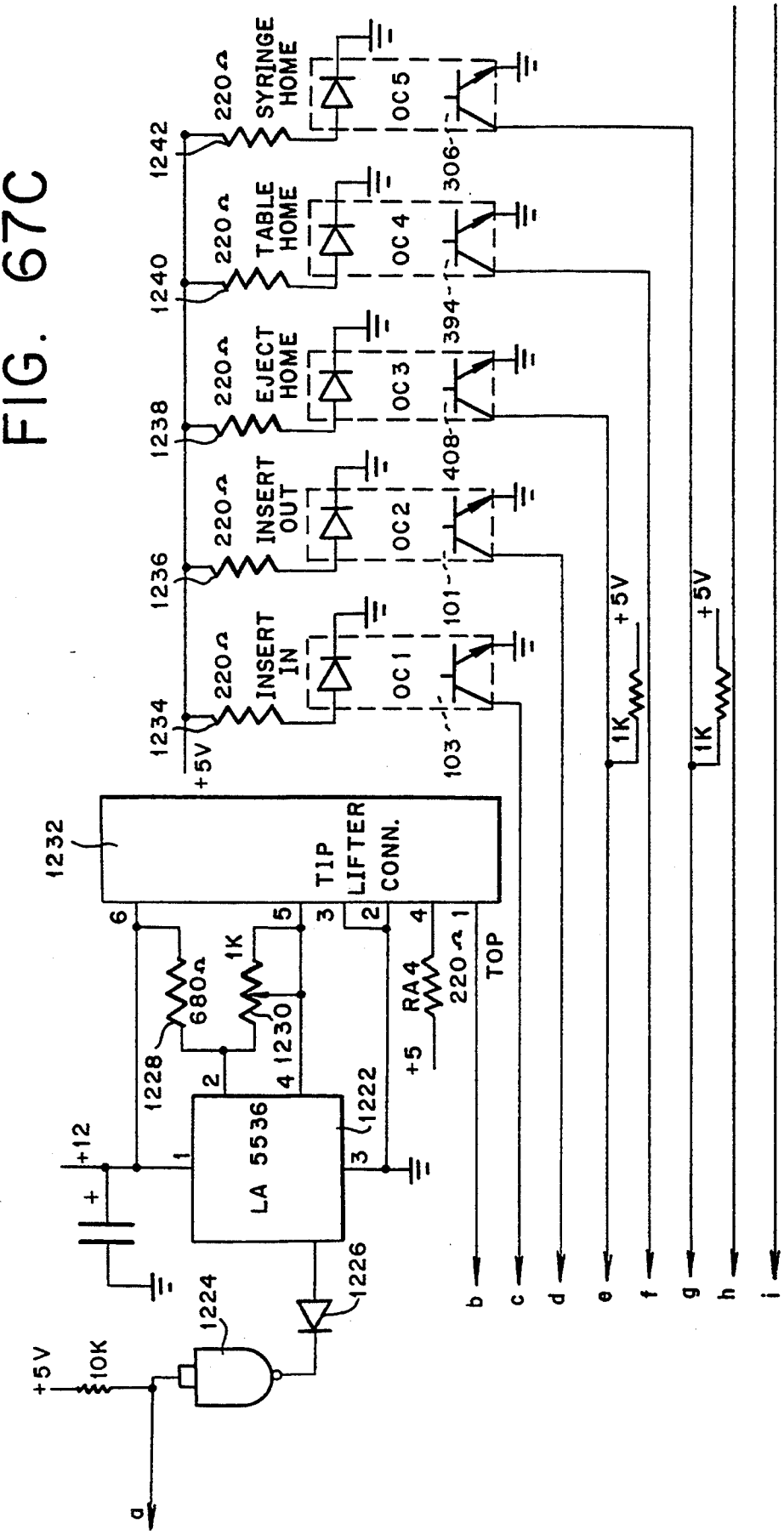
Figure 67D:
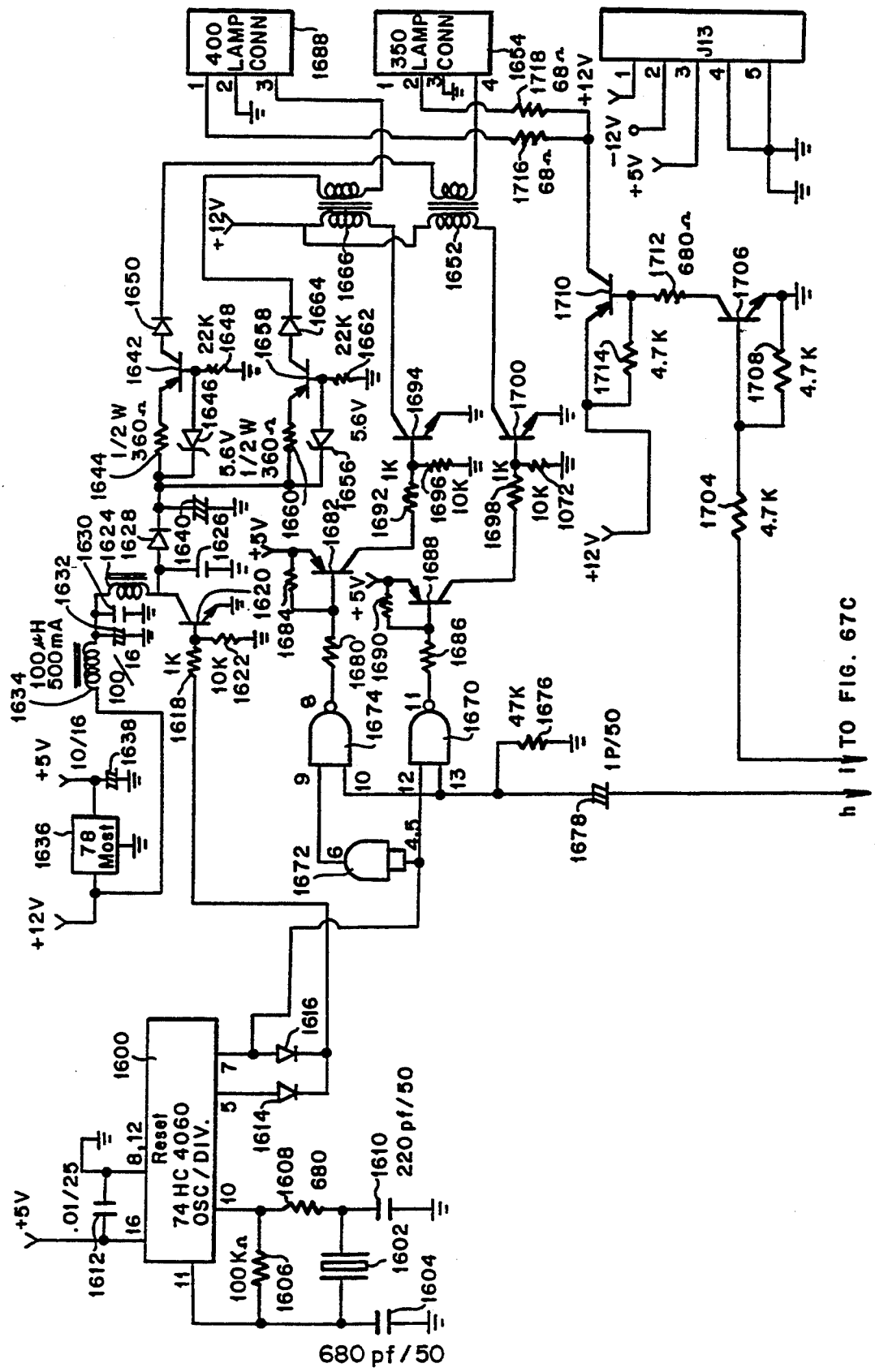

Because the clock, which will be described in relation to the computer interface subassembly 802 shown in FIG. 66, has started running at the zero crossing, the number of pulses generated by the clock may be counted. The clock is inhibited when the voltage on capacitor 1034 has reached the voltage level of the reflected light signal. Accordingly, because the voltage across capacitor 1034 is increasing at a constant rate, one merely has to count the number of pulses generated by the clock between the time of the zero crossing and when the level of the reflected light signal is reached to convert the reference light signal from its in analog form to a digital code.

In certain instances, the reflected light signal may be a negative voltage. Accordingly, the present invention starts the charging ramp for the analog-to-digital conversion from a negative voltage (i.e., −0.2 times the reference signal voltage), which is more negative than the reflected light signal which is expected, so that capacitor 1034 will charge up through the negative reflected light signal to the zero crossing level. In such a situation, comparators 1050 and 1042 will signal circuitry on the computer interface subassembly 802 to start the clock when the ramp voltage has reached the negative reference signal and to stop the clock when the ramp voltage has reached the zero crossing level. The number of pulses may be counted and, by knowing the slope of the charging voltage, the count signal will be indicative of the voltage level of the reflected light signal below ground. Also in such a situation comparator 1050 will change the state of its output first, indicating that the ramp voltage has reached the negative reference voltage level, and then comparator 1042 will change state when the ramp voltage has increased to the voltage level of ground.

One of the advantages of the analog-to-digital converter of the present invention is that it is ratiometric; that is, the output digital code representing the voltage level of the reflected light signal will always be presented in relation to the reference signal associated with the particular light source used in the measurement. Also included is a circuit comprising amplifier 1051, resistors 1053, 1055, 1057, 1059, 1061, capacitor 1063 and zener diode 1065 for amplifying the temperature sense signal from connector 1067 and providing the amplified signal to multiplexer 998.

The pre-amplifier and analog-to-digital converter subassembly 800 also includes a series of voltage regulators 1052-1058 and a series of filter capacitors 1060-1070 connected to the regulators and to ground, the voltage regulators providing ±9 volts and ±5 volts.

The pre-amplifier and analog-to-digital converter subassembly 800 also includes an LED driver 1072. The inputs of the LED driver 1072 are connected to the computer through connector 1002. The computer will energize one of the inputs at a time so that a particular LED 462 for the reflectometer will be energized. Each of the outputs of the LED driver 1072 is provided to an LED brightness control potentiometer 1074–1080 and to an output connector 1082 through series connected, currently limiting resistors 1084–1090. Connector 1082 is connected to a mating connector 1092 which is connected to the LEDs 462 of the reflectometer.

The computer interface subassembly 802 will now be described with reference to FIG. 66 of the drawings. Multiple bus lines 1100–1104 carrying information to and from the computer 850 are connected to a plurality of input/output buffers 1094–1098. The bus lines 1100–1104 carry control signals, address information and data from the computer 850 to the computer interface subassembly 802 and vice versa. The address data from the computer is provided to buffers 1094 and 1096, and the outputs of buffers 1094 and 1096 are provided to address decoders 1106 and 1108. Some of the outputs of the address decoders 1106, 1108 go to various integrated circuits on the computer interface subassembly 802, as illustrated in FIG. 66. Other outputs from the address decoders are provided to the mechanical interface board 804 which is shown in detail in FIG. 67.

Buffer 1098 receives data from the computer 850 and the output of buffer 1098 is connected to an eight line data bus 1110 which is connected to various integrated circuits on the computer interface subassembly. More specifically, the data bus 1110 is connected to programmable input/output circuits 1112–1116, and a counter 1118, and is provided through an appropriate connector 1120 to the mechanical interface subassembly 804.

As mentioned previously, the data bus is connected to integrated circuits 1112 through 1116 Each of these integrated circuits is a programmable input/output device. The programmable input/output devices 1112–1116 will either take data from the data bus 1110 and hold it, or put data onto the data bus from another circuit.

Connected to the programmable input/output device 1116 by another data bus 1122 is a real time clock 1124. The real time clock 1124 is associated with the computer 850 of the analyzer and it provides clock data to device 1116, which will output the clock data onto the data bus 1110.

Also connected by a way of a data bus 1126 is a LCD controller device 1128. LCD controller device 1128 receives data and control signals on the bus line 1126 from input/output device 1116. The LCD controller device 1128 will then address an external random access memory (RAM) 1130 which will act as a look-up table and provide data back to the LCD controller device 1128. Data which is held by the RAM is provided to controller device 1128, which then outputs this data through a connecter 1132 to the LCD display 8 of the blood analyzer.

Programmable input/output device 1114 receives address data from the data bus 1110 and provides address data to an electrically erasable programmable read only memory (EEPROM) 1134, which stores calibration parameters for the blood analyzer. Data from the EEPROM 1134 is provided back to the programmable input/output device 1114, which information may then be transmitted on the databus 1110 to the computer 850 and other associated circuitry.

Data from the computer is also provided from the data bus 1110 to input/output device 1112. Input/output device 1112 will direct data from the databus to the pre-amplifier and analog-to-digital converter subassembly 800 through a connector 1136 which is coupled to connector 1002 on the pre-amplifier subassembly 800.

The data which is provided to the preamplifier subassembly 800 by the computer 850 and through the computer interface subassembly 802 includes data to energize one of the four LEDs 462 of the reflectometer (this data is provided to LED driver 1072 on the pre-amplifier subassembly) and to select which channel of the reflected light signals are to be processed (this data goes to the select inputs A–C of the multiplexers 998 and 1000.

The computer interface subassembly 802 also includes the remaining portion of the analog-to-digital converter not found in the pre-amplifier and analog-to-digital converter subassembly 800. More specifically, the outputs of comparators 1050 and 1042, which are provided to connector 1002 are received on connector 1136 of the computer interface subassembly 802. Each of these output signals is provided to the clock input of a D-type flip flop through a logic inverter 1142, 1144 having hysteresis. The flip flops 1138, 1140 effectively act as noise or "bounce" eliminators, as there may be a certain amount of "ringing" or uncertainty in the output state of the comparators 1050 and 1042. The "D" inputs of the flip flops 1138, 1140 are grounded, the Preset inputs are connected to a high logic level, and the Set inputs are connected together and to a signal designated in FIG. 66 by the term "RUN" which signal is provided through input/output device 1112 from the computer 850.

The Q outputs of the flip flops 1138, 1140 are provided to an exclusive or gate 1146. Gate 1146 is connected to the Enable input of counter 1118 and will be used to control the running of the counter, that is, turning the counter on and off.

A third D-type flip flop 1148 has its Clock input connected to the Q output of the flip flop 1138 provided with the signal from the zero crossing comparator 1042, and has its D input connected to the Q output of the flip flop 1140 which is provided with the signal from comparator 1050. Also, the Set input of flip flop 1148 is connected to the RUN signal line, and its Reset input is held to a high logic level.

Flip flop 1148 is used to determine which comparator 1042 or 1050 changed its state first, which will be reflected on the outputs of the two noise eliminator flip flops 1138, 1140 to which the comparators are indirectly connected. The Q output of flip flop 1148 will be indicative of the polarity of the reflected light signal, that is, whether it is negative or positive and this polarity (i.e., from the Q output) signal is provided to the input/output device 1112 for transmission on the data bus 1110 to the computer 850.

The output of the exclusive or gate 1146 is also connected to the Clock input of a fourth D-type flip flop 1150, having its D input connected to a high logic level, its Set input also connected to a high logic level, and its Reset input connected to the "RUN" signal. The Q output of this fourth flip flop 1150 is an indication that the counter 1118 has been shut off, i.e., that analog-to-digital conversion of the reflected light signal has been completed. This signal from the Q output of flip flop 1150 is provided to the input/output device 1118 for transmission on the data bus 1110 to the computer 850.

A fifth D-type flip flop 1152 is connected to an "Overflow" output on counter 1118, and has its D input connected to ground, its Reset input connected to a high logic level and its Set input connected to the RUN signal. The Q output of the fifth flip flop 1152 provides a counter overflow or "Out of Range" signal, which signal is provided to the input/output device 1112 for transmission on the data bus 1110 to the computer 850.

Counter 1118 is used to provide a count signal which is, effectively, the digital equivalent of the analog voltage level of the unknown reflected light signal. Data from the computer 850 on the data bus 1110 is provided to the counter 1118 so that the counter may be programmed to count at a particular rate or for a particular number of counts.

Input/output device 1112 also receives data from the computer along the data bus 1110 and outputs this data to a printer controller 1154. Device 1154 controls the printer 10 of the analyzer and has associated with it circuitry comprising a number of inverters 1156-1164, a capacitor 1166, a resistor 1168, a diode 1170, resistors 1172 and 1174, a transistor 1176, resistors 1178 and 1180 and a potentiometer 1182. These components cooperate to form an oscillator for driving the printer controller 1154, and potentiometer 1182 is used as a frequency adjustment. The oscillator provides a 16 kHz signal for driving the printer controller 1154.

Printer controller 1154 is also connected to a tachometer circuit comprising a capacitor 1184, a transistor 1186, resistors 1188 and 1190 and a diode 1192. The tachometer circuit provides a signal to the printer 8 to control the position of the printer head. Printer controller 1154 also provides motor drive data on a data bus 1194 to the printer 8 through an appropriate connector 1196.

Input/output device 1112 is also connected through a connector 1198 to the keyboard 4 to receive data from the keyboard. It transmits this data along the data bus 1110 to the computer 850.

The mechanical interface subassembly 804 of the blood analyzer will now be described in detail and in relation to FIG. 67.

Input data from the data bus 1110 of the computer interface subassembly 802 is provided to a programmable input/output interface device 1200 through an appropriate connector 1202. A first set of output data from device 1500 is provided on bus line 1204 to a motor controller device 1206, which in turn provides signals on signal bus 1208, 1210 to the turntable stepping drive motor 348 and the syringe stepping drive motor 270. Through motor controller 1206 the computer can control the rotation of the drive motors 348, 270 for the turntable and the metering device to a high degree of accuracy. The data buses 1208, 1210 which carry this "stepping data" are provided to the turntable assembly and sample metering assembly through appropriate connectors, 1212 and 1214 respectively.

Also connected to the outputs of the input/output device 1200 is a second motor controller 1216. Controller 1216 is a DC motor driver for the drive motors. 398, 60 of the ejector assembly and the cover assembly. The output signals to drive these motors are provided to the ejector and cover assemblies through appropriate connectors 1218 and 1220, respectively. A "HOME" signal is also received from the cover assembly optical sensor 168 and provided to the input/output device 1200 for signaling the computer when the cover 54 is in its home position.

Another motor controller 1222 is connected to input/output device 1200 through a NAND gate 1224, acting as an inverter and through a series connected diode 1226. Motor controller 1222 is actually a motor speed regulator for controlling the speed of the pipette lifter assembly. Motor controller 1222, in association with a resistor 1228 connected to a positive voltage and a potentiometer 1230, allows the speed at which the pipette 18 is raised and lowered to be accurately controlLED. Potentiometer 1230 provides an adjustment for the speed at which the pipette lifter operates. The signals from motor controller 1222 are provided to the lifter assembly by a connector 1232. The optical sensor 218 associated with the pipette lifter provides a "TOP" signal, which indicates that the pipette is in its most raised position, through connector 1232 to the input/output device 1200, which signal is provided by device 1200 to the computer 850.

Also shown in FIG. 67 are the various optical sensors used in the blood analyzer. These include sensor 103, which indicates that the inserter plate 68 is in its most forward position; sensor 101, which indicates that the inserter plate is in its most backward position; sensor 408, which indicates that the ejector arm 404 is in its home position; sensor 394, which indicates that the turntable is in its home position; and sensor 306, which indicates that the syringe of the metering assembly is in its home position. The outputs of the above sensors are provided to the input/output device 1200, which device provides these signals to the computer 850 through the computer interface subassembly 802. It is to be noted that each of the LED light sources of the sensors is connected to a positive voltage through an appropriate resistor 1234–1242.

The brushes 390 which contact the slip rings of the turntable assembly are pictorially illustrated by FIG. 67. One brush, S, receives the signal from the temperature sensor 378 of the turntable assembly. Another brush, marked with a "+" sign, provides a positive voltage to the sensor and to the heater plate 380. The third brush, H, provides a path to sink current from the coils of the heater plate 380.

The signal from the sensor 378 on brush S is provided through a series resistor 1244 to the inverting input of an operational amplifier 1246. Amplifier 1246 has a feedback resistor 1248 which is in parallel with a capacitor 1250. The non-inverting input of amplifier 1246 is connected to ground. The signal from resistor 1244 is also provided through a series resistor 1252 to one end of a potentiometer 1254, the other end and wiper of which are connected to a zener diode 1256, a capacitor 1258 to ground, and a resistor 1260 to a negative voltage.

Potentiometer 1252 is provided to adjust the current output provided to the coils of the heater plate 380. The temperature sensor 378 on the turntable provides a current output signal which is proportional to temperature and which is preferably approximately one microamp of current per degree of temperature. The potentiometer 1254 is preferably a ten turn potentiometer and is adjusted so that when the temperature of the turntable 50 is exactly at 37°, the output of amplifier 1246 will be at 0 volts.

The output of amplifier 1246 is provided to the non-inverting input of a second operational amplifier 1262. The inverting input of amplifier 1262 is connected to the emitter of an NPN power transistor 1264, whose base is connected through a series resistor 1266 to the output of operational amplifier 1262, and to temperature connector 1263 through a resistor 1265. The collector of transistor 1264 is connected to the heater brush H. Connector 1263 is connected to resistor 1267 to ground, and to connector 1067 on preamplifier subassembly 800.

If the temperature of the turntable assembly should decrease, the voltage provided to the non-inverting input of amplifier 1262 will increase. Amplifier 1262 will then turn transistor 1264 on so that it sinks current from the coils of the heater plate of the turntable.

The heater control circuit described above also includes a PNP transistor 1268 having its base connected to the input/output device 1200, its emitter connected to the base of transistor 1264, and its collector connected to ground. Across the emitter and collector of transistor 1268 is a diode 1270 and a capacitor 1272. A signal DHTR * from the computer 850 and provided to the base of transistor 1268 will cause transistor 1268 to turn on, which in turn will bias transistor 1264 off to remove current from the heater plate coils of the turntable 50, thus shutting off the heater.

A second temperature control circuit is also part of the mechanical interface subassembly 804 of the blood analyzer and is used for controlling the temperature of the base plate 48. A positive voltage is provided to a temperature sensor 1274 which is mounted on the base plate 48. The output of sensor 1274 is connected through a series resistor 1276 to the inverting input of an operational amplifier 1278. The inverting input is also connected to a resistor 1280 which is connected to a ten turn potentiometer 1282, whose wiper and opposite side are connected to resistor 1260 and zener diode 1256. Like potentiometer 1254, potentiometer 1282 provides an adjustment to set up a zero voltage level on the output of operational amplifier 1278 when the temperature of the base plate 48 is at 37°.

Amplifier 1278 includes a feedback resistor 1284 connected in parallel with a capacitor 1286, and the non-inverting input of amplifier 1278 is connected to ground. The output of amplifier 1278 is provided to the non-inverting input of a second stage operational amplifier 1288, whose output is connected through a feedback resistor 1290 to the inverting input of the amplifier 1288 and to ground through a resistor 1292. The output of amplifier 1288 is connected to the base of an NPN transistor 1294 through a series resistor 1296, as well as to a capacitor 1298 connected to ground and a diode 1300 connected to ground. The collector of transistor 1294 is connected to the base plate heater 395 mounted on the base plate 48 of the analyzer through an appropriate connector 1302 and the emitter of transistor 1294 is connected to ground.

In the same manner as the temperature control circuit for the turntable 50, the temperature control circuit for the base plate 48 will cause transistor 1294 to turn on whenever the temperature sensed by sensor 1274 decreases. Transistor 1294 will then act as a sink for current passing through the base plate heater 395, and will turn off or go into a low conduction state when the temperature sensed by sensor 1274 increases to the desired value.

Each of the temperature control circuits for the turntable 50 and the base plate 48 described above are linear type circuits, that is, they provide a continual adjustment of approximately 0.2° C. variation over the 37° C. temperature initially set up for operation. Both transistors 1264 and 1294 preferably remain active during operation of the temperature control circuits. The purpose of keeping transistors 1264 and 1294 active is to provide a greater degree of control in the temperature of the turntable 50 and base plate 48, and also to prevent transient noise on the signals of the circuitry which might result if transistors 1264 and 1294 were continually driven into saturation or cut off.

Also shown on the mechanical interface subassembly 804 is the drive circuitry for the fluorescent lamps 428, 434 of the reflectometer. The drive circuitry basically includes a DC power source, as opposed as to an AC drive circuit. It has been found that a DC drive for the ultraviolet lamps will reduce noise, will provide a more consistent current to the fluorescent lamps and will prolong the life of the fluorescent lamps.

FIG. 67 shows a schematic diagram of a preferred form of a power supply circuit for the fluorescent lamp sources 422, 424. The power supply circuit more specifically includes a start up circuit and a constant current drive circuit.

An oscillator/divider circuit 1600, which may be a 14 stage divider, has its XI terminal connected to a 455 KHZ crystal 1602 (although other frequency crystals may be used), to a capacitor 1604 to ground, and to one end of a resistor 1606. The X0 terminal of the oscillator/divider circuit 1600 is connected to the other end of resistor 1606 and to a resistor 1608. The other end of resistor 1608 is connected to the other end of crystal 1602 and to a capacitor 1610 to ground. A filter capacitor 1612 is provided between the Vcc input (Pin 16) on oscillator/divider circuit 1600 and ground, and the "Reset" input is grounded.

The "Q5" output of circuit 1600 is provided to the anode of a diode 1614. Similarly, the output signal on the "Q4" output, which has a frequency of about 30 KHZ, is provided to the anode of another diode 1616. The cathodes of the two diode 1614, 1616 are connected together and are provided to the series base resistor 1618 of an NPN transistor 1620.

By connecting diodes 1614, 1616 together, a time varying signal having a 75% duty cycle is generated and provided to transistor 1620. Transistor 1620 will thus be turned on for 75% of the time, and off for 25%.

The emitter of transistor 1620 is connected to ground, its base is further connected to a resistor 1622 to ground (which acts as a voltage divider network with resistor 1618) and the collector of transistor 1620 is provided to one side of a "flyback" inductor or choke 1624, a capacitor 1626 to ground and the anode of a diode 1628. The other end of flyback choke 1624 is connected to two capacitors 1630, 1632 to ground, and to one end of another choke 1634, whose other end is connected to +12 volts. Capacitors 1630, 1632 function as a noise filter. (The +12V source may be provided to a regulator circuit 1636 to provide a +5 volts source. The +5V output of the regulator circuit 1636 is connected to a filter capacitor 1638 to ground.)

The cathode of diode 1628 is connected to a capacitor 1640 to ground and to two identical constant current transistor circuits. One transistor circuit includes a PNP transistor 1642, having an emitter resistor 1644 connected to diode 1628, a zener diode 1646 connected between the base of transistor 1642 to diode 1628, and a base resistor 1648 connected to ground. The collector of transistor 1642 is connected to the anode of a diode 1650, whose cathode is connected to one end of the secondary winding of a step-up transformer 1652. The other end of the secondary winding of transformer 1652 is provided to a connector 164, which is connected to the 350 nM fluorescent lamp.

The second transistor circuit includes a zener diode 1656, a PNP transistor 1658, a base resistor 1660, and an emitter resistor 1662, all connected together in the same manner as the circuit of transistor 1642. A collector diode 1664 is similarly provided, and its cathode is connected to one end of the secondary winding of a second step-up transformer 1666. The other end of the secondary winding is provided to a connector 1668, which is connected to the 400 nM fluorescent lamp.

The use of the flyback choke circuit in the constant current drives for the fluorescent lamps provides between about 100 and about 150 volts to drive the lamps. Accordingly, this voltage is generated even though only +12 volts is provided to the circuit. One of the reasons for using a constant current drive is that it has been found that the fluorescent lamps generate less noise when driven from a constant current DC source.

As mentioned previously, a start-up circuit for the fluorescent lamps is also provided. The output signal on the "Q4" output of the oscillator/divider circuit 1600 is provided to one input of a 2-input NAND gate 1670 and to the inputs of another NAND gate 1672 functioning as an inverter. The output of gate 1672 is provided to one input of a 2-input NAND gate 1674. The other inputs of gates 1670, 1674 are connected to a resistor 1676 to ground and to a capacitor 1678, whose other side is connected to the Pin 23 of the input/output circuit 1200. A "START" signal is provided by the computer on Pin 23, and is provided to capacitor 1678. Capacitor 1678 in conjunction with resistor 1676, provides a short duration "on" pulse to NAND gates 1670, 1674, enabling them and allowing the approximately 30 KHZ signal from the "Q4" output of circuit 1600 to pass through. The signals on the output of gate 1670 will be a 30 KHZ burst, of a duration proportional to the RC time constant defined by capacitor 1678 and resistor 1676. The signal on the output of gate 1674 will be the same as that of gate 1670, except opposite in state.

The outputs of the NAND gates are connected to two identical transistor drive circuits. More specifically, the output of gate 1674 is provided to a base resistor 1680 of a PNP transistor 1682. Transistor 1682 also has a resistor 1684 connected between its base and emitter, and its emitter is connected to +5 volts. The output of gate 1670 is similarly connected to a base resistor 1686 of a PNP transistor 1688, also having a base-emitter resistor 1690.

The collectors of transistors 1682, 1690 are connected to identical secondary transistor drive circuits. More specifically, transistor 1684 is connected to a series base resistor 1692 of an NPN transistor 1694, which transistor has a resistor 1696 from its base to ground, and has its emitter grounded. Transistor 1688 is connected to a base resistor 1698 of NPN transistor 1700, which also includes a base to ground resistor 1702 and has its emitter grounded.

The collector of transistor 1694 is connected to one end of the primary winding of transformer 1666, and the collector of transistor 1700 is connected to one end of the primary winding of transformer 1652. The other ends of the primary windings of transformers 1652, 1666 are connected to +12 volts.

When the START signal is generated by the computer, the circuit described above will provide a 250 volt AC signal burst to each fluorescent lamp in order to ionize the gases in the lamps. By alternating which of the two transistor drive circuits are on by using gate 1672, any noise generated when starting up the fluorescent lamps by the circuits which generate the 250 volts AC is minimized. Once the lamps have "started" there is no need for this high voltage signal. When gates 1670, 1674 have been disabled (by the short duration pulse on their inputs determined by the values of capacitor 1678 and resistor 1676), their output signals will go to a logic high state. This will turn off transistors 1684, 1688, which in turn will turn off transistors 1694, 1700. The transformers then will no longer provide 250 volts AC to the fluorescent lamps, and the lamps will draw the constant current they need to maintain the ionization of their gases from transistors 1642, 1660.

A power circuit for the filaments of the fluorescent lamps is also provided. When starting up the fluorescent lamps, the computer of the analyzer sends a "FILAMENT ON" signal through input/output circuit 1200. This signal is of short duration and is provided to the base resistor 1704 of an NPN transistor 1706, which also has a base-emitter resistor 1708 and has its emitter grounded.

The collector of transistor 1706 is connected to the base of a PNP transistor 1710 through a series base resistor 1712. Transistor 1710 also includes a base-emitter resistor 1714, and has its emitter connected to +12 volts. The collector of transistor 1710 is connected to two load resistors 1716, 1718, whose other ends are connected to the filaments of the fluorescent lamps through the respective connectors 1668, 1654.

When the fluorescent lamps are to be turned on, the computer will send the "FILAMENT ON" signal, and the signal provided by circuit 1200 to base resistor 1704 will go to a logic high state. This will turn on transistor 1706, which in turn will turn on transistor 1710, whose circuit acts as a current source for the filaments of the fluorescent lamps. The "FILAMENT ON" signal will cause the filaments to be energized for a short duration.

After about a one second delay after the "FILAMENT ON" signal was sent, the computer will send the "START" signal. The "START" signal will cause the power circuit to provide a high voltage (about 250 volts) AC signal to ionize the gases in the lamps. The high voltage is provided for only about 2 seconds. After about 3 seconds after start up, both the filament power circuit (i.e., transistors 1706, 1710) and the high voltage circuit (i.e., transistors 1684, 1690, 1694, 1700) are turned off, leaving only the constant current drive circuits (i.e., transistors 1642, 1660) to power the lamps.

Figure 68:
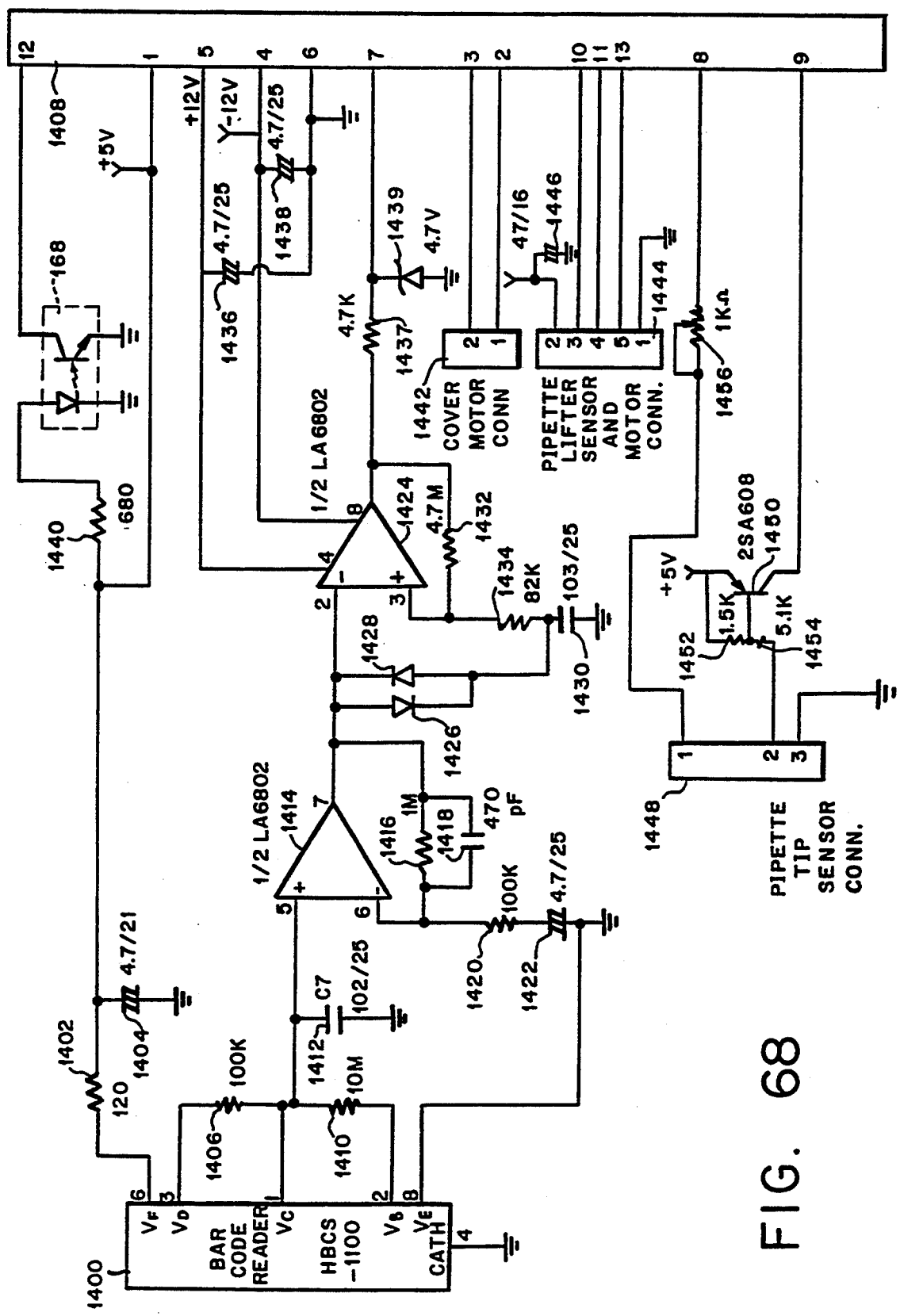
FIG. 68 is a schematic diagram of a fourth portion of the electronic circuitry of the analyzer.

FIG. 68 shows a schematic diagram of a preferred form of the circuitry of the bar code subassembly 158.

A bar code reader 1400, which is preferably Part No. HBCS-1100, manufactured by Hewlett-Packard Company, has its "$V_F$" input connected to a resistor 1402, whose other side is connected to a capacitor 1404 to ground, a resistor 1406, the "$V_D$" input of reader 1400, and to a +5V source through the subassembly's connector 1408. The "$V_C$" output of the reader 1400 is connected to the other side of resistor 1406, another resistor 1410, a capacitor 1412 to ground, and the non-inverting (+) input of an operational amplifier 1414.

The "$V_B$" input of reader 1400 is connected to the other side of resistor 1410, while the "$V_E$" input and "CATH" input are connected to ground.

Resistor 1402 provides a current source for the LED in the reader 1400. Resistor 1406 is the collector load for the phototransistor of the reader 1400. Resistor 1410 provides base bias for the phototransistor.

The signal measuring the reflectance from the bar codes on the top surface of the test slides is provided on the "$V_C$" output of the reader 1400. This signal is provided to amplifier 1414, which is configured to provide a non-inverting gain of 10. More specifically, amplifier 1414 has a 1M ohm feedback resistor 1416 (in parallel with a capacitor 1418) from its output to its inverting (−) input, and an input resistor 1420 of 100K ohms connected from its inverting input to a capacitor 1422 to ground. Operational amplifier 1414 may be ½ of Part No. LA6802, manufactured by Sanyo Corporation.

The output of amplifier 1414 is provided to a peak detector and comparator circuit. More specifically, the output of amplifier 1414 is connected to the inverting (−) input of operational amplifier 1424, which acts as a comparator and can be the other half of Part No. LA6802, the anode of diode 1426 and the cathode of diode 1428. The cathode and anode of diodes 1426 and 1428, respectively, are connected together and to a capacitor 1430 to ground. Capacitor 1430 acts as a peak detector by storing the output signal on amplifier 1414, minus the voltage drop (approximately 0.6 volts) across the diodes 1426, 1428.

The non-inverting (+) input of amplifier 1424 is connected to a feedback resistor 1432, whose other end is connected to the output of amplifier 1424, and to an input resistor 1434, whose other end is connected to the capacitor 1430. +12 volts and −12 volts are provided to amplifiers 1414 and 1424 through the connector 1408, and filter capacitors 1436 and 1438 are provided on the subassembly and connected between the voltage sources and ground.

Diodes 1426, 1428 allow capacitor 1430 to charge to the level of the signal on the output of amplifier 1414, minus 0.6 volts, the drop across the diodes. The signal on capacitor 1430 is compared with the signal on the output of amplifier 1414. The signal on the capacitor 1430 lags the output signal of amplifier 1414. If one is on a positive slope of the time varying output signal of amplifier 1414, the inverting input of comparator 1424 will always be more positive than the comparator's non-inverting input. Under such circumstances, the output of the comparator (amplifier 1424) will be −10 volts.

If the slope of the signal on the output of amplifier 1414 changes by more than 0.6 volts, the comparator will change states, because the voltage on the comparator's non-inverting input will be greater than the voltage on its inverting input. The output will then go to +10 volts. The comparator's change in state occurs in response to the optical bar code printed on the test slide scanned by the reader 1400.

The output of amplifier (comparator) 1424 is provided to a resistor 1437, whose other end is connected to a 4.7 volt zener diode 1439 to ground and to the subassembly's connector 1408. This signal, which is now 0 volts to approximately +5 volts due to the diode 1439, is provided to the computer of the analyzer for processing.

The bar code subassembly 158 further includes the optical sensor 168 for the cover motor's "home" position, and a resistor 1440 connected between sensor 168 and +5 volts to drive the LED of the sensor.

The subassembly further includes a connector 1442 providing a power signal to the cover motor 60; another connector 1444 for connection to the pipette lifter motor 226 and "home" position sensor 266, with a filter capacitor 1446 to ground on the voltage line provided to the pipette lifter assembly; and a third connector 1448 for connection to the pipette tip opto-sensor 175. Because the signal from sensor 175 is of a small magnitude, an amplifier is included on subassembly 158. More specifically, a transistor 1450 configured as a common base amplifier, with a resistor 1452 between its base and its emitter and another resistor 1454 between its base and the phototransistor of sensor 175 through connector 1448, amplifies the signal from sensor 175 and provides the amplified signal to connector 1408. Potentiometer 1456 controls the sensitivity of the sensor by adjusting the current to sensor 175.

It can be seen from the above description that the chemical analyzer of the present invention can simultaneously run twelve tests in a small, low cost, desk top unit. The total time for twelve tests is approximately seven minutes, whereas conventional analyzers may require as much as sixty minutes to complete the same tests.

The design of the cover 54 of the present invention includes individual spring-loaded portions (i.e., E button members 140) which cover the test slides and which are tolerant of considerable variation in slide thickness. Furthermore, the cover is easily removable to allow cleaning of unintentional spills.

The simplified optical head design of the reflectometer portion of the analyzer provides a single visible region E assembly which uses a single photodiode with four LEDs to select the wavelength.

The rotating cover 54 allows slides to be exposed for bar code reading and spotting with serum and covered during the test to control evaporation.

The heater control portion and associated circuitry of the incubator provides +0.1° C. control. Thus, it accurately maintains the temperature of the test slides to within a narrow range, but yet is low cost and simple in construction. It further maintains the temperature irrespective of the voltage drop across the brushes associated with the slip rings.

In a preferred form of the analyzer, small, low cost, high production volume fluorescent lamps 424, 434 with custom phosphors are used in order to provide light in the ultraviolet wavelength region. This delivers a narrow band emission, which reduces the cost of the narrow band, ultraviolet filters 431, 440 and consumes very low power to minimize heating effects. The fluorescent lamps are relatively inexpensive and have a long life (that is, up to 2,000 hours or more). Conventional chemical analyzers use xenon or mercury lamps, which are much more expensive and require much higher power (that is, 50 watts and more). Thus, many conventional analyzers require cooling for their lamps, which is not required in the present invention. Furthermore, such lamps produce wide band emissions, which require costly filtering, and have a shorter useful life (that is, 1,000 hours and less).

For the visible region of the spectrum, the chemical analyzer of the present invention uses low cost LEDs (producing 555–680 nM wavelength emissions) rather than high cost lamps and filters.

The chemical analyzer of the present invention also employs low cost ratiometric analog-to-digital circuitry, which provides high resolution and good short term stability.

The chemical analyzer of the present invention provides real time information to the user as the tests are run by displaying a plot of reflectance verses time so that a knowledgeable user can spot potential blood problems before the test is complete.

The metering assembly of the chemical analyzer of the present invention utilizes a low cost, off the shelf gas chromatograph syringe which provides high accuracy. Also, the articulated vertical motion pipette assembly provides highly accurate drop volumes irrespective of varying slide thicknesses.

The test results are analyzed by the chemical analyzer of the present invention according to species, and out-of-normal bounds are flagged. Additionally, a data base indicates potential problems (i.e., liver, kidney, dehydration, etc.) by examining the results of the test, and these problems are displayed by the analyzer for the user's convenience.

Although illustrative embodiments of the present invention have been described herein with reference to the accompanying drawings, it is to be understood that the invention is not limited to those precise embodiments, and that various other changes and modifications may be effected therein by one skilled in the art without departing from the scope or spirit of the invention.

What is claimed is:

1. A method of compensating for the backlash between a lead screw and a lead screw engaging member of a fluid sample metering device, the lead screw engaging member moving reciprocatingly in the axial direction of the lead screw upon rotation of the lead screw, which method comprises the steps of:

measuring the axial distance the lead screw engaging member moves in a first axial direction to a first position when the lead screw is rotated in a first rotational direction a predetermined number of revolutions;

measuring the axial distance the lead screw engaging member moves in a second axial direction which is opposite to the first axial direction from the first position when the lead screw is rotated the predetermined number of revolutions in a second rotational direction which is opposite to the first rotational direction;

determining the difference in the distances which the lead screw engaging member moved in the opposite first and second axial directions;

storing a value corresponding to the difference in distance in a storage memory;

sensing whenever the lead screw is to change direction of rotation from the first rotational direction to the second-rotational direction; and adding a rotational amount corresponding to the difference value to the number of rotations the lead screw is turned in the second rotational direction to compensate for the backlash between the lead screw and the lead screw engaging member.

* * * * *

UNITED STATES PATENT AND TRADEMARK OFFICE
CERTIFICATE OF CORRECTION

PATENT NO. : 5,336,467
DATED : August 9, 1994
INVENTOR(S) : Heidt

It is certified that error appears in the above-indentified patent and that said Letters Patent is hereby corrected as shown below:

Column 8, line 67, the phrase "test slide so" should read --test slide 71 so--.

Column 12, line 14, the phrase "slots through" should read --slots 52 through--.

Column 12, line 15, the phrase "leaf springs 11" should read --leaf springs 116--.

Column 13, line 7, the phrase "shoulders 38" should read --shoulders 138--.

Column 22, line 28, the phrase "foil 306" should read --foil 308--.

Column 22, line 32, the phrase "sensor 308" should read --sensor 306--.

Column 26, line 67, the phrase "not shown)" should read --(not shown)--.

Column 27, line 5, the phrase "The Slide Elector Mechanism" should read --The Slide Ejector Mechanism--.

Column 32, line 43, the phrase "light impinge on" should read --light sources 422-426 to cause light of a particular wavelength to impinge on--.

UNITED STATES PATENT AND TRADEMARK OFFICE
CERTIFICATE OF CORRECTION

PATENT NO. : 5,336,467
DATED : August 9, 1994
INVENTOR(S) : Heidt

It is certified that error appears in the above-indentified patent and that said Letters Patent is hereby corrected as shown below:

Column 33, line 1, insert as a heading therebefore --<u>The Operation of the Analyzer</u>--.

Column 33, line 63, the expression "37°C. 35 0.2°C" should read --37°C ± .2°C--.

Column 38, line 53, after "back up" insert--.--.

Column 41, line 28, the numerals "740 742" should read --740, 742--.

Column 42, line 16, the phrase "the routine,." should read --the routine--.

Column 42, line 22, the phrase "this routine is shogun" should read --this routine is shown--.

Column 42, line 33, the phrase "(Block 554)" should read --(Block 564)--.

Column 51, line 41, the phrase "device 1500 is" should read --device 1200 is--.

UNITED STATES PATENT AND TRADEMARK OFFICE
CERTIFICATE OF CORRECTION

PATENT NO. : 5,336,467
DATED : August 9, 1994
INVENTOR(S) : Heidt

It is certified that error appears in the above-indentified patent and that said Letters Patent is hereby corrected as shown below:

Column 51, line 54, the phrase "the drive motors. 398," should read --the drive motors 398,--.

Column 54, line 64, the phrase "connector 164" should read --connector 1654--.

Column 58, line 29, the phrase "provides + 0.1°C." should read --provides ± .1°C--.

Signed and Sealed this

Fourth Day of July, 1995

Attest:

BRUCE LEHMAN

Attesting Officer

Commissioner of Patents and Trademarks

UNITED STATES PATENT AND TRADEMARK OFFICE
CERTIFICATE OF CORRECTION

PATENT NO. : 5,336,467
DATED : August 9, 1994
INVENTOR(S) : Heidt

It is certified that error appears in the above-indentified patent and that said Letters Patent is hereby corrected as shown below:

Title page, item [19], the phrase "Heidt et al." should read --Heidt--.
Title page, item [75], the phrase "Thomas Heidt, Long Valley;
Henry Will, Dover;Greydon Rhode, Chester; Armand Plasencia, Hopatcong, all of N.J.; Roger Clampitt, Hemel Hempstead, United Kingdom" should read
--Thomas Heidt, Long valley, N.J.--.

Signed and Sealed this

Twenty-second Day of August, 1995

*Attest:*

BRUCE LEHMAN

*Attesting Officer*          *Commissioner of Patents and Trademarks*